(12) United States Patent
Bielawska et al.

(10) Patent No.: US 8,697,379 B2
(45) Date of Patent: Apr. 15, 2014

(54) LYSOSOMOTROPIC INHIBITORS OF ACID CERAMIDASE

(75) Inventors: Alicja Bielawska, Charleston, SC (US); Aiping Bai, Charleston, SC (US); Zdzislaw M. Szulc, Charleston, SC (US); Yusuf A. Hannun, Sullivan's Island, SC (US); James S. Norris, Mount Pleasant, SC (US); Liu Xiang, Mount Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 116 days.

(21) Appl. No.: 13/127,888

(22) PCT Filed: Nov. 6, 2009

(86) PCT No.: PCT/US2009/063586
§ 371 (c)(1),
(2), (4) Date: Jun. 16, 2011

(87) PCT Pub. No.: WO2010/054223
PCT Pub. Date: May 14, 2010

(65) Prior Publication Data
US 2011/0251197 A1    Oct. 13, 2011

Related U.S. Application Data

(60) Provisional application No. 61/111,852, filed on Nov. 6, 2008.

(51) Int. Cl.
*A61K 31/41* (2006.01)
*A61K 31/44* (2006.01)
*C07C 229/00* (2006.01)
*C07D 211/78* (2006.01)

(52) U.S. Cl.
USPC .............. 435/15; 435/193; 514/548; 560/155

(58) Field of Classification Search
USPC ..................... 435/15, 193; 514/548; 560/155
See application file for complete search history.

(56) References Cited

U.S. PATENT DOCUMENTS

| | | | |
|---|---|---|---|
| 2,515,465 A | 7/1950 | Mozingo et al. | |
| 3,044,936 A * | 7/1962 | Achelis et al. | 514/619 |
| 3,466,292 A | 9/1969 | Paquette et al. | |
| 4,016,287 A | 4/1977 | Eberhardt et al. | |
| 4,151,198 A | 4/1979 | Halmos | |
| 4,283,541 A | 8/1981 | Schroff et al. | |
| 4,474,977 A | 10/1984 | Lambelin et al. | |
| 4,544,670 A | 10/1985 | Studt et al. | |
| 4,622,365 A | 11/1986 | Fujii et al. | |
| 4,859,761 A | 8/1989 | Flury et al. | |
| 4,897,355 A | 1/1990 | Eppstein et al. | |
| 4,937,232 A | 6/1990 | Bell et al. | |
| 5,369,030 A | 11/1994 | Hannun et al. | |
| 5,559,154 A | 9/1996 | Weber et al. | |
| 5,679,350 A | 10/1997 | Jankun et al. | |
| 5,830,916 A | 11/1998 | Hannun et al. | |
| 5,851,782 A | 12/1998 | Hannun et al. | |
| 5,916,911 A | 6/1999 | Shayman et al. | |
| 6,284,798 B1 | 9/2001 | Amtmann et al. | |
| 6,610,835 B1 | 8/2003 | Liotta et al. | |
| 6,696,081 B2 | 2/2004 | Grinstaff et al. | |
| 6,756,504 B2 | 6/2004 | Dagan et al. | |
| 7,172,879 B2 | 2/2007 | Gamble et al. | |
| 8,093,393 B2 | 1/2012 | Bielawska et al. | |
| 8,592,419 B2 | 11/2013 | Bielawska et al. | |
| 2003/0133904 A1 | 7/2003 | Dagan et al. | |
| 2005/0209260 A1 | 9/2005 | Broka et al. | |
| 2008/0045470 A1 * | 2/2008 | Bielawska et al. | 514/44 |
| 2008/0146640 A1 * | 6/2008 | Glinka | 514/397 |
| 2008/0167352 A1 | 7/2008 | Smith et al. | |
| 2008/0268073 A1 | 10/2008 | Sano et al. | |
| 2011/0071099 A1 | 3/2011 | Bielawska et al. | |
| 2012/0035268 A1 | 2/2012 | Szulc et al. | |

FOREIGN PATENT DOCUMENTS

| | | |
|---|---|---|
| GB | 630 712 | 10/1949 |
| GB | 1 487 283 | 9/1977 |
| WO | WO00/27883 | 5/2000 |
| WO | WO01/79152 | 10/2001 |
| WO | WO02/22175 | 3/2002 |
| WO | WO03/005965 | 1/2003 |
| WO | WO2004/074247 | 9/2004 |
| WO | WO2006/050264 | 5/2006 |

(Continued)

OTHER PUBLICATIONS

Kast, et al Suppressing Glioblastoma Stem Cell Function by Aldehyde Dehydrogenase Inhibition with Chloramphenicol or Disulfiram as a New Treatment Adjunct: A Hypothesis, Current Stem Cell Research and Therapy, 2009, vol. 4, pp. 314-317.*
"Ceramide," Wikipedia. <http://en.wikipedia.org/wiki/Ceramide> pp. 1-4 (Accessed on Nov. 4, 2010).
Agrawal et al., "Cell-Cycle kinetics and VSV-G pseudotyped retrovirus-mediated gene transfer in blood-derived CD34+ cells," Experimental Hematology, vol. 24 pp. 738-747 (1996).
Ardail et al., "Subcellular distribution and metabolic fate of exogenous ceramides taken up by HL-60 cells," Biochimica et Biophysica Acta. vol. 1583 pp. 305-310 (2002).

(Continued)

*Primary Examiner* — Susannah Chung
(74) *Attorney, Agent, or Firm* — Jenkins, Wilson, Taylor & Hunt, P.A.

(57) ABSTRACT

The presently disclosed subject matter provides compounds of the formula, formula (Ia): and pharmaceutically acceptable salts thereof, wherein $R_1$, $R_2$, $R_3$, $R_4$, $R_5$, X, Y, and n are as defined herein. Also disclosed are methods for making the compounds of the formula as set forth hereinabove, their use in inhibiting acid ceramidase and ceramidase-related activity, and their use as drugs and prodrugs in the treatment and/or prevention of diseases associated with undesirable ceramidase or sphingosine kinase activity, including, but not limited to, cancer, cancer metastasis, atherosclerosis, stenosis, inflammation, asthma, and atopic dermatitis.

9 Claims, 21 Drawing Sheets

(56) References Cited

FOREIGN PATENT DOCUMENTS

| WO | WO2006/050265 | 5/2006 |
|---|---|---|
| WO | WO2006/138660 | 12/2006 |
| WO | WO2010/054223 | 5/2010 |
| WO | WO2010/078247 | 7/2010 |

OTHER PUBLICATIONS

Ashkenazi, A., and Dixit, V.M., "Apoptosis control by death and decoy receptors," Current Opinion in Cell Biology. vol. 11, pp. 255-260 (1999).

Ashkenazi, A., and Dixit, V.M., "Death Receptors: Signaling and Modulation," Science. vol. 281 pp. 1305-1308 (1998).

Bai et al., "Synthesis and Bioevaluation of ω-Amino Analogs of B13 as Potential Anticancer Agents Targeting Acid Ceramidase," Poster (SERLC, Sep. 11, 2008).

Bai et al., "Synthesis and bioevaluation of ω-N-amino analogs of B13," Bioorganic & Medicinal Chemistry. vol. 17 pp. 1840-1848 (2009).

Bernatowicz et al., "Urethane Protected Derivatives of 1-Guanylpyrazole for the Mild and Efficient Preparation of Guanidines," Tetrahedron Letters. vol. 34, No. 21 pp. 3389-3392 (1993).

Bieberich et al., "N-Acylated Serinol is a Novel Ceramide Mimic Inducing Apoptosis in Neuroblastoma Cells," The Journal of Biological Chemistry. vol. 275, No. 1 pp. 177-181 (2000).

Bieberich et al., "Synthesis and characterization of novel ceramide analogs for induction of apoptosis in human cancer cells," Cancer Letters. vol. 181 pp. 55-64 (2002).

Bielawska et al., "(1S,2R)-D-erythro-2-(N-Myristoylamino)-1-phenyl-1-propanol as an Inhibitor of Ceramidase," The Journal of Biological Chemistry. vol. 271, No. 21 pp. 12646-12654 (1996).

Bielawska et al., "Ceramide-mediated Biology," The Journal of Biological Chemistry. vol. 267, No. 26 pp. 18493-18497 (1992).

Bielawska et al., "Novel analogs of D-e-MAPP and B13. Part 2: Signature effects on bioactive sphingolipids," Bioorganic & Medicinal Chemistry. vol. 16 pp. 1032-1045 (2008).

Bielawska et al., "Selectivity of Ceramide-mediated Biology," The Journal of Biological Chemistry. vol. 268, No. 35 pp. 26226-26232 (1993).

Bielawska et al., "Synthesis of Key Precursors of Radiolabeled Sphingolipids," Methods in Enzymology. vol. 311 pp. 518-535 (1999).

Bielawski et al., "Simultaneous quantitative analysis of bioactive sphingolipids by high-performance liquid chromatography-tandem mass spectrometry," Methods. vol. 39 pp. 82-91 (2006).

Birbes et al., "Selective hydrolysis of a mitochondrial pool of sphingomyelin induces apoptosis," FASEB Journal. vol. 14 pp. 2669-2679 (2001).

Black, W.C., and Percival, M.D., "The Consequences of Lysosomotropism on the Design of Selective Cathepsin K Inhibitors," ChemBioChem. vol. 7 pp. 1525-1535 (2006).

Bose et al., "Ceramide Synthase Mediates Daunorubicin-Induced Apoptosis: An Alternative Mechanism for Generating Death Signals," Cell. vol. 82 pp. 405-414 (1995).

Boya et al., "Mitochondrial membrane permeabilization is a critical step of lysosome-initiated apoptosis induced by hydroxychloroquine," Oncogene. vol. 22 pp. 3927-3936 (2003).

Brown et al., "Mechanism of action of a dominant-negative mutant of c-Jun," Oncogene. vol. 9 pp. 791-799 (1994).

Buchwald et al., "Long-term, continuous intravenous heparin administration implantable infusion pump in ambulatory patients with recurrent venous thrombosis," Surgery. vol. 88, No. 4 pp. 507-516 (1980).

Buttle et al., "CA074 Methyl Ester: A Proinhibitor for Intracellular Cathepsin B," Archives of Biochemistry and Biophysics, vol. 299, No. 2 pp. 377-380 (1992).

Chad et al., "Site-Directed Mutagenesis of UDP-Galactopyranose Mutase Reveals a Critical Role for the Active-Site, Conserved Arginine Residues," Biochemistry. vol. 46 pp. 6723-6732 (2007).

Chalfant et al., "FAS Activation Induced Dephosphorylation of SR Proteins," The Journal of Biological Chemistry. vol. 276, No. 48 pp. 44848-44855 (2001).

Chalfant et al., "The structural requirements for ceramide activation of serine-threonine protein phosphatases," J. Lipid Res. vol. 45 pp. 496-506 (2004).

Charles et al., "Ceramide-Coated Balloon Catheters Limit Neointimal Hyperplasia After Stretch Injury in Carotid Arteries," Circ Res. vol. 87 pp. 282-288 (2000).

Chen et al., "Relationship between the pharmacological action and the chemical constitution and configuration of the optical isomers of ephedrine and related compounds," J. Pharmacol. vol. 36 pp. 363-400 (1929) [Abstract].

Cherioux, F., and Audebert, P., "New Star-Shaped Molecules with Extended Electronic Delocalization," Chem. Mater. vol. 10 pp. 1984-1989 (1998).

Clement, "In-vitro-Untersuchungen zur mikrosomalen N-Oxidation einiger Guanidine," Arch. Pharm. (Weinheim). vol. 319 pp. 961-968 (1986) [Abstract].

Cremesti et al., "Ceramide Enables Fas to Cap and Kill," The Journal of Biological Chemistry. vol. 276, No. 26 pp. 23954-23961 (2001).

Dagan et al., "Synthetic, non-natural sphingolipid analogs inhibit the biosynthesis of cellular sphingolipids, elevate ceramide and induce apoptotic cell death," Biochimica et Biophysica Acta. vol. 1633, No. 3 pp. 161-169 (2003).

Dahm et al., "Mitochondrially targeted ceramide LCL-30 inhibits colorectal cancer in mice," British Journal of Cancer. vol. 98 pp. 98-105 (2008).

Database Beilstein Beilstein Institute for Organic Chemistry, Frankfurt-Main, DE; 1932, Database Accession No. BRN: 3854595 & Slotta, Justus Liebigs Annalen der Chemie. vol. 497 pp. 171-178 (1932).

Database Beilstein Beilstein Institute for Organic Chemistry, Frankfurt-Main, DE; 1993, Database Accession No. BRN: 3684371 & Abderhalden, Schweitzer: Fermentforschung. vol. 13 pp. 128-133 (1933) [Abstract].

Database Beilstein Beilstein Institute for Organic Chemistry, Frankfurt-Main, DE; 1949, Database Accession No. BRN: 3814715 & Cornforth, Chem. Penicillin. pp. 688 and 798 (1949) [Abstract].

Database Beilstein Beilstein Institute for Organic Chemistry, Frankfurt-Mian, DE; 1958, Database Accession No. BRN: 3805955 & Kratzl, Berger: Monatshefte fuer Chemie. vol. 89 pp. 160-164 (1958) [Abstract].

Database Beilstein Beilstein Institute for Organic Chemistry, Frankfurt-Main, DE; 1966, Database Accession No. BRN: 4138625 & Ciusa, Barbiroli: Annali di Chimica. vol. 56 pp. 3-6 (1966) [Abstract].

Database Beilstein Beilstein Institute for Organic Chemistry, Frankfurt-Main, DE; 1982, Database Accession No. BRN: 4628299 & Katritzky et al., Journal of Heterocyclic Chemistry. vol. 19 pp. 741-745 (1982).

Davis et al., "Mitochondrial and Plasma Membrane Potentials Cause Unusual Accumulation and Retention of Rhodamine 123 by Human Breast Adenocarcinoma-derived MCF-7 Cells," The Journal of Biological Chemistry. vol. 260, No. 25 pp. 13844-13850 (1985).

Di Paola et al., "Ceramide Interaction with the Respiratory Chain of Heart Mitochondria," Biochemistry. vol. 39 pp. 6660-6668 (2000).

Dindo et al., "Cationic long-chain ceramide LCL-30 induces cell death by mitochondrial targeting in SW403 cells," Molecular Cancer Therapeutics. vol. 5, No. 6 pp. 1520-1529 (2006).

El Bawab et al., "Biochemical Characterization of the Reverse Activity of Rat Brain Ceramidase," The Journal of Biological Chemistry. vol. 276, No. 20 pp. 16758-16766 (2001).

El Bawab et al., "Purification and Characterization of a Membrane-bound Nonlysosomal Ceramidase from Rat Brain," The Journal of Biological Chemistry. vol. 274, No. 39 pp. 27946-27955 (1999).

El Bawab et al., "Substrate specificity of rat brain ceramidase," J. Lipid Res. vol. 43 pp. 141-148 (2002).

Elojeimy et al., "Role of Acid Ceramidase in Resistance to FasL: Therapeutic Approaches Based on Acid Ceramidase Inhibitors and FasL Gene Therapy," Molecular Therapy. vol. 15, No. 7 pp. 1259-1263 (2007).

(56) References Cited

OTHER PUBLICATIONS

Emerson, "Syntheses with Styrene Oxide," J. Am. Chem. Soc. vol. 67 pp. 516-518 (1945).
English et al., "Sphigosine 1-phosphate released from platelets during clotting accounts for the potent endothelial cell chemotactic activity of blood serum and provides a novel link between hemostasis and angiogenesis," FASEB Journal. vol. 14 pp. 2255-2265 (2000).
Extended European Search Report corresponding to European Patent Application No. 05 820 909.9-2101 dated Jul. 3, 2009.
Extended European Search Report corresponding to European Patent Application No. 05 821 150.9-1211 dated Feb. 10, 2011.
Extended European Search Report corresponding to European Patent Application No. 09 825 496.4-2123 dated Mar. 7, 2012.
Extended European Search Report corresponding to European Patent Application No. 09 837 076.0-1211 dated Dec. 14, 2011.
Fantin et al., "A novel mitochondriotoxic small molecule that selectively inhibits tumor cell growth," Cancer Cell. vol. 2 pp. 29-42 (2002).
Felgner et al., "Lipofection: A highly efficient, lipid-mediated DNA-transfection procedure," PNAS. vol. 84 pp. 7413-7417 (1987).
Feng, C., and Wilson, S.D., "Some derivatives of ephedrine," Zhongguo Shenglixue Zazhi. vol. 4 pp. 231-246 (1930) [Abstract].
French et al., "Antitumor Activity of Sphingosine Kinase Inhibitors," The Journal of Pharmacology and Experimental Therapeutics. vol. 318, No. 2 pp. 596-603 (2006).
French et al., "Discovery and Evaluation of Inhibitors of Human Sphingosine Kinase," Cancer Research. vol. 63 pp. 5962-5969 (2003).
Fujii, A., and Cook, E.S., "Probiotics. Antistaphylococcal and Antifibrinolytic Activities of ω-Guanidino Acids and ω-Guanidinoacyl-L-histidines," Journal of Medicinal Chemistry. vol. 16, No. 12 pp. 1409-1411 (1973).
García-Ruiz et al., "Direct Effect of Ceramide on the Mitochondrial Electron Transport Chain Leads to Generation of Reactive Oxygen Species," The Journal of Biological Chemistry. vol. 272, No. 17 pp. 11369-11377 (1997).
Garner et al., "A Stereodivergent Synthesis of D-erthyro-Sphingosine and D-threo-Sphingosine from L-Serine," J. Org. Chem. vol. 53, No. 18 pp. 4395-4398 (1988).
Ghafourifar et al., "Ceramide Induces Cytochrome c Release from Isolated Mitochondria," The Journal of Biological Chemistry. vol. 274, No. 10 pp. 6080-6084 (1999).
Ghosh et al., "Probing the function(s) of active-site arginine residue in *Leishmania donovani* adenosine kinase," Biochem. J. vol. 298 pp. 295-301 (1994).
Goodman et al., "Recombinant Adeno-Associated Virus-Mediated Gene Transfer Into Hematopoietic Progenitor Cells," Blood. vol. 84, No. 5 pp. 1492-1500 (1994).
Grether-Beck et al., "Mitochondrial Cytochrome c Release Mediates Ceramide-induced Activator Protein 2 Activation and Gene Expression," The Journal of Biological Chemistry. vol. 278, No. 48 pp. 47498-47507 (2003).
Gu et al., "Induction of p53-regulated genes in lung cancer cells: implications of the mechanism for adenoviral p53-mediated apoptosis," Oncogene. vol. 23 pp. 1300-1307 (2004).
Hakogi et al., "Synthesis of Fluorescence-Labeled Sphingosine and Sphingosine 1-Phosphate; Effective Tools for Sphingosin and Sphingosine 1-Phosphate Behaviour," Bioorganic & Medicinal Chemistry Letters. vol. 13 pp. 661-664 (2003).
Hann, B., and Balmain, A., "Building 'validated' mouse for models of human cancer," Current Opinion in Cell Biology. vol. 13 pp. 778-784.
Hannun, "Functions of ceramide in coordinating cellular responses to stress," Science. vol. 274, No. 5294 pp. 1855-1859 (1996).
Hannun, Y.A., and Luberto, C., "Ceramide in the eukaryotic stress response," Trends in Cell Biology, vol. 10 pp. 73-80 (2000).
Hansen et al., "Re-examination and further development of a precise and rapid dye method for measuring cell growth/cell kill," Journal of immunological Methods. vol. 119 pp. 203-210 (1989).

Hayter et al., "TNFα-induced glutathione depletion lies downstream of cPLA2 in L929 cells," FEBS Letters. vol. 507 pp. 151-156 (2000).
He et al., "Purification and Characterization of Recombinant, Human Acid Ceramidase," The Journal of Biological Chemistry. vol. 278, No. 35 pp. 32978-32986 (2003).
Hla, "Signaling and biological actions of sphingosine 1-phosphate," Pharmacological Research. vol. 47 pp. 401-407 (2003).
Holman et al., "Lysosomotropic acid ceramidase inhibitor in prostate cancer cells," Cancer Chemother. Pharmacol. vol. 61 pp. 231-242 (2008).
Howard et al., "Intracerebral drug delivery in rats with lesion induced memory deficits," J. Neurosurg. vol. 71 pp. 105-112 (1989).
Huwiler, A., and Zangemeister-Wittke, U., "Targetting the conversion of a ceramide to sphingosine 1-phosphate as a novel strategy for cancer therapy," Oncology Hematol. vol. 63 pp. 150-159 (2007).
Hyer et al., "Downregulation of c-FLIP Sensitizes DU145 Prostate Cancer Cells to Fas-Mediated Apoptosis," Cancer Biology & Therapy. vol. 1, No. 4 pp. 401-406 (2002).
Hyer et al., "Quantification and characterization of the bystander effect in prostate cancer cells following adenovirus-mediated FasL expression," Cancer Gene Therapy. vol. 10 pp. 330-339 (2003).
Inaba et al., "Evaluation of Antitumor Activity in a Human Breast Tumor/Nude Mouse Model With a Special Emphasis on Treatment Dose," Cancer. vol. 64 pp. 1577-1582 (1989).
Interview Summary corresponding to U.S. Appl. No. 11/666,518 dated Nov. 26, 2010.
Interview Summary corresponding to U.S. Appl. No. 11/666,518 dated May 2, 2011.
Interview Summary corresponding to U.S. Appl. No. 11/666,519 dated Jun. 15, 2010.
Johnson et al., "Role of Human Sphingosine-1-phosphate Phosphatase 1 in the regulation of Intra- and Extracellular Sphingosine-1-phosphate Levels and Cell Viability," The Journal of Biological Chemistry. vol. 278, No. 36 pp. 34541-34547 (2003).
Jones et al., "Ceramide Induces Caspase-Independent Apoptosis in Rat Hepatocytes Sensitized by Inhibition of RNA Synthesis," Hepatology. vol. 30 pp. 215-222 (1999).
Jones-Bolin et al., "The effects of the oral, pan-VEGF-R kinase inhibitor CEP-7055 and chemotherapy in orthotopic models of glioblastoma and colon carcinoma in mice," Molecular Cancer Therapeutics. vol. 4, No. 7 pp. 1744-1753 (2006).
Jursic, "An Enantiomeric Discrimination in Aqueous Mixed Chiral Micelles Through Hydrogen Bonding," Tetrahedron Letters. vol. 34, No. 6 pp. 963-966 (1993).
Kamo et al., "Membrane Potential of Mitochondrial Measured with an Electrode Sensitive to Tetraphenyl Phosphonium and Relationship between Proton Electrochemical Potential and Phosphorylation Potential in Steady State," J. Membrane Biology. vol. 49 pp. 105-121 (1979).
Karahatay et al., "Clinical relevance of ceramide metabolism in the pathogenesis of human head and neck squamous cell carcinoma (HNSCC): Attenuation of C18-ceramide in HNSCC tumors correlates with lymphovascular invasion and nodal metastasis," Cancer the Letters. vol. 256 pp. 101-111 (2007).
Kaufmann, A.M., and Krise, J.P., "Lysosomal Sequestration of Amine-Containing Drugs: Analysis and Therapeutic Implications," Journal of Pharmaceutical Sciences. vol. 96, No. 4 pp. 729-746 (2007).
Kim et al., "Synthesis and evaluation of sphingoid analogs as inhibitors of sphingosine kinases," Bioorganic & Medicinal Chemistry. vol. 13 pp. 3475-3485 (2005).
Klymchenko et al., "Ultrasensitive two-color fluorescence probes for dipole potential in phospholipid membranes," PNAS. vol. 100, No. 20 pp. 11219-11224 (2003).
Koch et al., "Molecular Cloning and Characterization of a Full-length Complementary DNA Encoding Human Acid Ceramidase," The Journal of Biological Chemistry. vol. 271, No. 51 pp. 33110-33115 (1996).
Kornfeld, "The Biogenesis of Lyosomes," Annu. Rev. Cell Biol. vol. 5 pp. 483-525 (1989).
Koybasi et al., "Defects in Cell Growth Regulation by C18:0-Ceramide and Longevity Assurance Gene 1 in Human Head and

(56) References Cited

OTHER PUBLICATIONS

Neck Squamous Cell Carcinomas," The Journal of Biological Chemistry. vol. 279, No. 43 pp. 44311-44319 (2004).
Langer, "New methods of drug delivery," Science. vol. 249, No. 4976 pp. 1527-1533 (1990).
Larsen et al., "Synthesis and Biological Activity of Analogues of the Antidiabetic/Antiobesity Agent 3-Guanidinopropionic Acid: Discovery of a Novel Aminoguanidinoacetic Acid Antidiabetic Agent," Journal of Medicinal Chemistry. vol. 44, No. 8 pp. 1217-1230 (2001).
Lazewska et al., "Piperidine-containing histamine $H_3$-receptor antagonists of the carbamate series: variation of the spacer length," Pharmazie. vol. 56, No. 12 pp. 927-932 (2001).
Lee et al., "Sphingosine-1-Phosphate as a Ligand for the G Protein-Coupled Receptor EDG-1," Science. vol. 279 pp. 1552-1555 (1998).
Levy et al., "Inhibition of calcification of bioprosthetic heart valves by local controlled-release diphosphonate," Science. vol. 228 p. 190 (1985).
Libby et al., "A Cascade Model for Restenosis: A Special Case of Atherosclerosis Progression," Circulation. vol. 86, No. 6, Suppl. III pp. III47-III52 (1992).
Lim et al., "Synthesis and Cytotoxicity of New 3-Alkyl-1-(1-methyl-2-phenylethyl)ureas Related to Ceramide," Archives of Pharmacal Research. vol. 26, No. 4 pp. 270-274 (2003).
Liu et al., "Acid ceramidase inhibition: a novel target for cancer therapy," Frontiers in Bioscience. vol. 13 po. 2293-2298 (2008).
Liu et al., "Glutathione Regulation of Neutral in Tumor Necrosis Factor-α-induced Cell Death," THe Journal of Biological Chemistry. vol. 273, No. 18 pp. 11313-11320 (1998).
Lowe et al., "Prostate-specific expression of Bax delivered by an adenoviral vector induces apoptosis in LNCaP prostate cancer," Gene Therapy. vol. 8 pp. 1363-1371 (2001).
Lutz et al., "Antimalarials. α-phenyl-β-dialkylamino alcohols," Journal of Organic Chemistry. vol. 12 pp. 617-703 (1947).
Macchia et al., "Design, Synthesis, and Characterization of the Antitumor Activity of Novel Ceramide Analogues," J. Med. Chem. vol. 44 pp. 3994-4000 (2001).
Maceyka et al., "Sphingosine kinase, sphingosine-1-phosphate, and apoptosis," Biochemica et Biohysica Acta. vol. 1585 pp. 193-201 (2002).
Mahboob, S., and Dhar, M.L., "Studies in Potential Amoebicides: Part II—Synthesis of Some Polymethylene Diamines," Journal of Scientific & Industrial Research. vol. 14B pp. 1-6 (1955).
Makino et al., "Comparative study between daily and 5-days-a-week administration of oral 5-fluorouracil chemotherapy in mice: determining the superior regimen," Cancer Chemother. Pharmacol. vol. 48 pp. 370-374 (2001).
Mao et al., "Cloning and Characterization of a Novel Human Alkaline Ceramidase," The Journal of Biological Chemistry. vol. 276, No. 28 pp. 36577-35688 (2001).
Mathias et al., "Signal transduction of stress via ceramide," Biochem. J. vol. 335 pp. 465-480 (1998).
Maedama et al., "FLICE is activated by association with the CD95 death-inducing signaling complex (DISC)," The EMBO Journal. vol. 16, No. 10 pp. 2794-2804 (1997).
Miller, A.D., and Buttimore, C., "Redesign of Retrovirus Recombination Packaging Cell Lines to Avoid Leading to Helper Virus Production," Molecular and Cellular Biology. vol. 6, No. 8 pp. 2895-2902 (1986).
Mimeault, "New advances on structural and biological functions of ceramide in apoptotic/necrotic cell death and cancer," FEBS Letters. vol. 530 pp. 9-16 (2002).
Mitani et al., "Transduction of Human Bone Marrow by Adenoviral Vector," Human Gene Therapy. vol. 5 pp. 941-948 (1994).
Miyashita, T., and Reed, J.C., "Tumor Supressor p53 Is a Direct Transcriptional Activator of the Human bax Gene," Cell. vol. 80 pp. 293-299 (1995).
Modica-Napolitano, J.S., and Aprile, J.R., "Delocalized lipophilic cations selectively target the mitochondria of carcinoma cells," Advanced Drug Delivery Reviews. vol. 49 pp. 63-70 (2001).

Muzio et al., "FLICE Induced Apoptosis in a Cell-Free System," The Journal of Biological Chemistry. vol. 272, No. 5 pp. 2952-2956 (1997).
Nakano, K., and Vousden, K.H., "PUMA, a Novel Proapoptotic Gene, Is Induced by p53," Molecular Cell. vol. 7 pp. 683-694 (2001).
Naldini et al., "In Vivo Gene Delivery and Stable Transduction of Nondividing Cells by a Lentiviral Vector," Science. vol. 272 pp. 263-267 (1996).
Nechushtan et al., "Bax and Bak Coalesce into Novel Mitochondria-associated Clusters during Apoptosis," The Journal of Cell Biology. vol. 153, No. 6 pp. 1265-1276 (2001).
Ninkar et al., "A Stereoselective Synthesis of Sphingosine, A Protein Kinase C Inhibitor," Tetrahedron Letters. vol. 29, No. 25 pp. 3037-3040 (1988).
Notice of Allowance corresponding to U.S. Appl. No. 11/666,518 dated Aug. 9, 2011.
Notification Concerning Transmittal of International Preliminary Report on Patentability (Chapter I of the Patent Cooperation Treaty) corresponding to International Patent Application No. PCT/US2005/039271 dated May 10, 2007.
Notification Concerning Transmittal of International Preliminary Report on Patentability (Chapter I of the Patent Cooperation Treaty) corresponding to International Patent Application No. PCT/US2005/039272 dated May 10, 2007.
Notification Concerning Transmittal of International Preliminary Report on Patentability (Chapter I of the Patent Cooperation Treaty) corresponding to International Patent Application No. PCT/US2009/063586 dated May 19, 2011.
Notification Concerning Transmittal of International Preliminary Report on Patentability (Chapter I of the Patent Cooperation Treaty) corresponding to International Patent Application No. PCT/US2009/069583 dated Jul. 14, 2011.
Notification of Transmittal of the International Search Report and Written Opinion of the International Searching Authority, or the Declaration corresponding to International Patent Application No. PCT/US2005/039271 dated Mar. 23, 2006.
Notification of Transmittal of the International Search Report and Written Opinion of the International Searching Authority, or the Declaration corresponding to International Patent Application No. PCT/US2005/039272 dated Jan. 30, 2007.
Notification of Transmittal of the International Search Report and Written Opinion of the International Searching Authority, or the Declaration corresponding to International Patent Application No. PCT/US2009/063586 dated Mar. 5, 2010.
Notification of Transmittal of the International Search Report and the Written Opinion of the International Searching Authority, or the Declaration corresponding to International Patent Application No. PCT/US2009/069583 dated Mar. 22, 2010.
Novgorodov et al., "Activation of sphingosine-1-phosphate receptor S1P5 inhibits oligodendrocyte progenitor migration," The FASEB Journal. vol. 21 pp. 1503-1514 (2007).
Novgorodov et al., "Positively Charged Ceramide Is a Potent Inducer of Mitochondrial Permeabilization," Journal of Biological Chemistry. vol. 280, No. 16 pp. 16096-16105 (2005).
Nussbaumer et al., "One-step labelling of sphingolipids via a scrambling cross-metathesis reaction," Chem. Commun. vol. 40 pp. 5086-5087 (2005).
Obeid et al. "Programmed cell death induced by ceramide," Science. vol. 259, No. 5102 pp. 1769-1771 (1993).
Official Action corresponding to Canadian Patent Application No. 2,585,645 dated Mar. 13, 2012.
Official Action corresponding to European Patent Application No. 05 820 909.9-2101 dated Oct. 2, 2009.
Official Action corresponding to European Patent Application No. 05 820 909.9-2101 dated Sep. 27, 2011.
Official Action corresponding to European Patent Application No. 05 821 150.9-1211 dated Mar. 28, 2012.
Official Action corresponding to U.S. Appl. No. 11/666,518 dated Aug. 5, 2010.
Official Action corresponding to U.S. Appl. No. 11/666,518 dated Jan. 6, 2011.
Official Action corresponding to U.S. Appl. No. 11/666,519 dated Feb. 3, 2010.

(56) References Cited

OTHER PUBLICATIONS

Official Action corresponding to U.S. Appl. No. 11/666,519 dated Jul. 14, 2010.
Official Action corresponding to U.S. Appl. No. 11/666,519 dated Feb. 25, 2011.
Ogretmen, B., and Hannun, Y.A., "Biologically Active Sphingolipids in Cancer Pathogenesis and Treatment," Nature. vol. 4 pp. 604-616 (2004).
Ogretmen et al., "Role of Ceramide in Mediating the Inhibition of Telomerase Activity in A549 Human Lung Adenocarcinoma Cells," The Journal of Biological Chemistry. vol. 276, No. 27 pp. 24901-24910 (2001).
Onda et al., "Molecular Recognition of Nucleotides by the Guanidinium Unit at the Surface of Aqueous Micelles and Bilayers. A Comparison of Microscopic and Macroscopic Interfaces," J. Am. Chem. Soc. vol. 118 pp. 8524-8530 (1996).
Orlinick, J.R., and Chao, M.V., "TNF-Related Ligands and Their Receptors," Cell. Signal. vol. 10, No. 8 pp. 543-551 (1998).
Papucci et al., "Coenzyme $Q_{10}$ Prevents Apoptosis by Inhibiting Mitochondrial Depolarization Independently of Its Free Radical Scavenging Property," The Journal of Biological Chemistry. vol. 278, No. 30 pp. 28220-28228 (2003).
Pastan et al., "A retrovirus carrying an MDR1 cDNA confers multidrug reisistance and polarized expression of P-glycoprotein in MDCK cells," PNAS. vol. 85 pp. 4486-4490 (1988).
Paugh et al., "A selective sphingosine kinase 1 inhibitor integrates multiple molecular therapeutic targets in human leukemia," Blood. vol. 112, No. 4 pp. 1382-1391 (2008).
Perry, D.K., and Hannun, Y.A., "The role of ceramide in signaling," Biochimica et Biophysica Acta. vol. 1436 pp. 233-243 (1998).
Pettus et al., "The sphingosine kinase 1/sphingosine-1-phosphate pathway mediates COX-2 induction and PGE2 production in response to TNF-α," FASEB Journal. vol. 17 pp. 1411-1421 (2003).
Radin, "Designing Anticancer Drugs Via the Achilles Heel: Ceramide, Allylic Ketones, and Mitochondria," Bioorganic & Medicinal Chemistry. vol. 11 pp. 2123-2142 (2003).
Raisova et al., "Bcl-2 overexpression prevents apoptosis induced by ceramidase inhibitora in malignant melanoma and HaCaT keratinocytes," FEBS Letters. vol. 516 pp. 47-52 (2002).
Raisova et al., "Resistance to CD95/Fas-induced and ceramide-mediated apoptosis of human melanoma cells is caused by a defective mitochondrial cytochrome c release," FEBS Letters. vol. 473 pp. 27-32 (2000).
Rao et al., "$^{31}$P NMR Studies of the Arginine Kinase Reaction," The Journal of Biological Chemistry. vol. 251, No. 22 pp. 6981-6986 (1976).
Rautio et al., "Prodrugs: design and clinical applications," Nature Reviews. vol. 7 pp. 255-270 (2008).
Rebbaa et al., "Doxorubicin-induced apoptosis in caspase-8-deficient neuroblastoma cells in mediated through direct action on mitochondria," Cancer Chemother. Pharmacol. vol. 48 pp. 423-428 (2001).
Robbins and Angell, "Basic Pathology," 2nd Edition, W.B. Saunders Co.: Philadelphia. pp. 68-78 and 112-113 (1976).
Roberg et al., "Lysosomal Release of Cathepsin D Precedes Relocation of Cytochrome C and loss Mitochondrial Transmembrane Potential During Apoptosis Induced by Oxidative Stress," Free Radical Biology & Medicine. vol. 27, Nos. 11-12 pp. 1228-1237 (1999).
Rosania et al., "Combinatorial Approach to Organelle-Targeted Fluorescent Library Based on the Styryl Scaffold," Journal of the American Chemical Society. vol. 125 pp. 1130-1131 (2003).
Rossi et al., "Inhibition of growth and telomerase activity by novel cationic ceramide analogs with high solubility in human head and neck squamous cell carcinoma cells," Otolaryngology—Head and Neck Surgery. vol. 132, No. 1 pp. 55-62 (2005).
Rubinchik et al., "A Complex Adenovirus Vector That Delivers FASL-GFP with Combined Prostate-Specific and Tetracycline-Regulated Expression," Molecular Therapy. vol. 4, No. 5 pp. 416-426 (2001).

Sage et al., "Inhibition of Endothelial Cell Proliferation by SPARC Is Mediated Through a $Ca^{2+}$-Binding EF-Hand Sequence," Journal of Cellular Biochemistry. vol. 57 pp. 127-140 (1995).
Samsel et al., "The Ceramide Analog, B13, Induces Apoptosis in Prostate Cancer Cell Lines and Inhibits Tumor Growth in Prostate Cancer Xenografts," The Prostate. vol. 58 pp. 382-393 (2004).
Scaffidi et al., "Two CD95 (APO-1/Fas) signaling pathways," The EMBO Journal. vol. 17, No. 6 pp. 1675-1687 (1998).
Schotte et al., "Non-specific effects of methyl ketone peptide inhibitors of caspases," FEBS Letters. vol. 442 pp. 117-121 (1999).
Schulze-Osthoff et al., "Apoptosis signaling by death receptors," Eur. J. Biochem. vol. 254 pp. 439-459 (1998).
Schwandner et al., "TNF Receptor Death Domain-associated Proteins TRADD and FADD Signal Activation of Acid Sphingomyelinase," The Journal of Biological Chemistry. vol. 273, No. 10 pp. 5916-5922 (1998).
Schwarzenberger et al., "Targeted Gene Transfer to Human Hematopoietic Progenitor Cell Lines Through the c-kit Receptor," Blood. vol. 87, No. 2 pp. 472-478 (1996).
Seebach et al., "Lithiation and electrophilic substitution at alpha-methylene groups of ntirosamines. Reactivity umpolung of secondary amines," Chemische Berichte. vol. 110, No. 5 pp. 1852-1865 (1977) [Abstract].
Seelan et al., "Human Acid Ceramidase is Overexpressed but not Mutated in Prostate Cancer," Genes, Chromosomes & Cancer. vol. 29 pp. 137-146 (2000).
Selzner et al., "Induction of Apoptopic Cell Death and Prevention of Tumor Growth by Ceramide Analogues in Metastatic Human Colon Cancer," Cancer Research. vol. 61 pp. 1233-1240 (2001).
Senchenkov et al., "Targeting Ceramide Metabolism—a strategy for Overcoming Drug Resistance," J. Natl. Cancer Inst. vol. 93 pp. 347-357 (2001).
Senkal et al., "Potent Antitumor Activity of a Novel Cationic Pyridinium-Ceramide Alone or in Combination with Gemcitabine against Human Head and Neck Squamous Cell Carcinomas in Vitro and in Vivo," The Journal of Pharmacology and Experimental Therapeutics. vol. 317, No. 3 pp. 1188-1199 (2006).
Separovic et al., "C16-Ceramide Analog Combined with Pc 4 Photodynamic Therapy Evokes Enhanced Total Ceramide Accumulation, Promotion of DEVDase Activiation in the Absence of Apoptosis, and Augmented Overall Cell Killing," Journal of Lipids. pp. 1-9 (2011).
Shapiro et al., "Hypoglycemic Agents. III.1-3 N1-Alkyl- and Aralkylbiguanides," Journal of the American Chemical Society. vol. 81 pp. 3728-3736 (1958).
Shi et al., "Complex Functions of Mutant p53 Alleles From Prostate Cancer," The Prostate. vol. 51 pp. 59-72 (2002).
Siskind et al., "Ceramide Channels Increase the Permeability of the Mitochondrial Outer Membrane to Small Proteins," The Journal of Biological Chemistry. vol. 277, No. 30 pp. 26796-26803 (2002).
Sobel, R.E., and Sadar, M.D., "Cell Lines Used in Prostate Cancer Research: A Compendium of Old and New Lines—Part 1," The Journal of Urology. vol. 173 pp. 342-359 (2005).
Song et al., "Kinetics and Mechanisms of Activation of α-Amino Acid Ester Prodrugs of Camptothecins," J. Med. Chem. vol. 49 pp. 4344-4355 (2006).
Speer, J.H., and Hill, A.J., "Some Nucleus Alkyl Derivatives of Phenethylamine," The Journal of Organic Chemistry. vol. 2, No. 2 pp. 139-147 (1937)
Sullards, M.C., and Merrill, Jr., A.H., "Analysis of Sphingosine 1-Phosphate, Ceramides, and Other Bioactive Sphingolipids by High-Performance Liquid Chromatography-Tandem Mass Spectrometry," Sci. STKE. vol. 67 pp. 1-11 (2001).
Sundararaj et al., "Rapid Shortening of Telomere Length in Response to Ceramide Involves the Inhibition of Telomere Binding Activity of Nuclear Glyceraldehyde-3-phosphate Dehydrogenase," The Journal of Biological Chemistry. vol. 279, No. 7 pp. 6152-6162 (2004).
Szalai et al., "Apoptosis driven by IP3-linked mitochondrial calcium signals," The EMBO Journal. vol. 18, No. 22 pp. 6349-6361 (1999).
Szulc et al., "Novel analogs of D-ef-MAPP and B13. Part 1: Synthesis and evaluation as potential anticancer agents," Bioorganic & Medicinal Chemistry. vol. 16 pp. 1015-1031 (2008).

(56) References Cited

OTHER PUBLICATIONS

Szulc et al., "Tailoring structure-function and targeting properties of ceramides by site-specific cationization," Bioorganic & Medicinal Chemistry. vol 14 pp. 7083-7104 (2006).
Taha et al., "A house divided: ceramide, sphingosine, and sphingsine-1-phosphate in programmed cell death," Biochim. Biophys. Acta. vol. 1758, No. 12 pp. 2027-2036 (2006).
Takahashi et al., "Human Fas ligand: gene structure, chromosomal location and species specificity," International Immunology. vol. 6, No. 10 pp. 1567-1574 (1994).
Takeya et al., "Synergistic effect of sphingosine 1-phosphate on thrombin-induced tisue factor expression in endothelial cells," Blood. vol. 102 pp. 1693-1700 (2003).
Tepper et al., "CD95/Fas-induced Ceramide Formation Proceeds with Slow Kinetics and Is Not Blocked by Caspase-3/CPP32 Inhibition," The Journal of Biological Chemistry. vol. 272, No. 39 pp. 24308-24312 (1997).
Tepper et al., "Role for ceramide as an endogenous mediator of Fas-induced cytotoxicity," PNAS. vol. 92 pp. 8443-8447 (1995).
Thornberry, N.A., and Lazebnik, Y., "Caspasese: Enemies Within," Science. vol. 281 pp. 1312-1316 (1998).
Tolsma et al., "Peptides Derived from Two Seperate Domains of the Matrix Protein Thrombospondin-1 Have Anti-Angiogenic Activity," The Journal of Cell Biology. vol. 122 No. 2 pp. 497-511 (1993).
Trnka, T.M., and Grubbs, R.H., "The Developement of L2X2Ru=CHR Olefin Metathesis Catalysts: An Organometallic Success Story," Acc. Chem. Res. vol. 34 pp. 18-29 (2001).
Ueoka et al., "Isokinetic Discriminiation of Artificial Membrane Systems in the Enantioselective Hydrolysis," Tetrahedron Letters. vol. 25, No. 13 pp. 1363-1366 (1984).
Usta et al., "Structural Requirements of Ceramide and Sphingosine Based Inhibitors of Mitochondrial Ceramidase," Biochemistry. vol. 40 pp. 9657-9668 (2001).
van Moorsel et al., "Scheduling of Gemcitabine and Cisplatin in Lewis Lung Tumour Bearing Mice," European Journal of Cancer. vol. 35, No. 5 pp. 808-814 (1999).
Veerman et al., "Antitumor activity of prolonged as compared with bolus administration of 2',2'-difluorodeoxycytidine in vivo against murine colon tumors," Pharmacol. pp. 335-342 (1996).
Vig et al., "Amino Acid Ester Prodrugs of Floxuridine: Synthesis and Effects of Structure, Stereochemistry, and Site of Esterification on the Rate of Hydrolysis," Pharmaceutical Research. vol. 20, No. 9 pp. 1381-1388 (2003).
Volk, C.A., and Köck, M., "Viscosamine: The First Naturally Occurring Trimeric 3-Alkyl Pyridinium Alkaloid," Organic Letters. vol. 5, No. 20 pp. 3567-3569 (2003).
von Haefen et al., "Ceramide induces mitochondrial activation and apoptosis via a Bax-dependent pathway in human carcinoma cells," Oncogne. vol. 21 pp. 4009-4019 (2002).
Wagenknecht et al., "C2-ceramide signaling in glioma cells: synergistic enhancement of CD95-mediated, caspase-dependent apoptosis," Cell Death and Differentiation. vol. 8 pp. 595-602 (2001).
Watterson et al., "Pleiotropic actions of sphingosine-1-phosphate," Progress in Lipid Research. vol. 42 pp. 344-357 (2003).
Weissman, "Themes and Variations on Ubiquitylation," Nature Reviews Molecular Cell Biology. vol. 2 pp. 169-178 (2001).
Wyllie et al., "Cell Death: The Significance of Apoptosis," International Review of Cytology. vol. 68 pp. 251-306 (1980).
Yamaguchi et al., "Copper(II) Reagent-Promoted Degradation of N,N'-dialkyldiazenedicarboxamides," Bulletin of the Chemical Society of Japan. vol. 75, No. 2 pp. 329-333 (2002).
Yamanaka et al., "Engraftment of Tonsillar Mononuclear Cells in Human Skin/SCIS Mouse Chimera—Validation of a Nove Xenogeneic Transplantation Model for Autoimmune Diseases—," Microbiol. Immunol. vol. 45, No. 7 pp. 507-514 (2001).
Yatomi et al., "Sphingosine-1-Phosphate: A Platelet-Activating Sphingolipid Released Form Agonist-Stimulated Human Platelets," Blood. vol. 86, No. 1 pp. 193-202 (1995).
Zeidan et al., "Acid Ceramidase but Not Acid Sphingomyelinase Is Required for Tumor Necrosis Factor-α-induced PGE2 Production," The Journal of Biological Chemistry. vol. 281, No. 34 pp. 24695-24703 (2006).
Official Action corresponding to Chinese Patent Application No. 200980154007.6 dated Mar. 13, 2013.
Official Action corresponding to U.S. Appl. No. 11/666,519 dated Mar. 25, 2013,
Official Action corresponding to U.S. Appl. No. 13/142,421 dated Apr. 30, 2013.
Communication under Rule 71(3) EPC corresponding to European Patent Application No. 05 820 909.9-2101 dated Nov. 2, 2012.
Notice of Allowance corresponding to Canadian Patent Application No. 2,585,775 dated Feb. 2, 2013.
Official Action corresponding to Canadian Patent Application No. 2,585,645 dated Jan. 16, 2013.
Official Action corresponding to Canadian Patent Application No. 2,585,775 dated Apr. 16, 2012.
Official Action corresponding to U.S. Appl. No. 11/666,519 dated Sep. 6, 2012.
Oggenfuss et al., "Transport of Ions through Neutral Carrier Membranes," Analytical Chemistry Symposia Series. vol. 8 pp. 73-86 (1981) [Abstract].
Communication under Rule 71(3) EPC corresponding to European Patent Application No. 05 820 909.9-2101 dated Jul. 16, 2013.
Notice of Allowance corresponding to U.S. Appl. No. 11/666,519 dated Jul. 10, 2013.
Communication under Rule 71(3) EPC corresponding to European Patent Application No. 05 820 909.9—1452 dated Jan. 16, 2014.
Official Action corresponding to Canadian Patent Application No. 2,585,645 dated Dec. 6, 2013.
Official Action corresponding to Chinese Patent Application No. 200980154007.6 dated Dec. 2, 2013.
Official Action corresponding to European Patent Application No. 09 825 496.4—1464 dated Nov. 11, 2013.

* cited by examiner

LYSOSOMOTROPIC INHIBITORS OF ACID CERAMIDASE

CROSS REFERENCE TO RELATED APPLICATION

This application claims the benefit of U.S. Provisional Patent Application Ser. No. 61/111,852, filed Nov. 6, 2008, the disclosure of which is incorporated herein by reference in its entirety.

GOVERNMENT INTEREST

This presently disclosed subject matter was made with U.S. Government support under Grant No. P01 CA097132 awarded by the National Institutes of Health and the National Cancer Institute. Thus, the U.S. Government has certain rights in the presently disclosed subject matter.

TECHNICAL FIELD

The presently disclosed subject matter relates to amphiphilic lysosomotropic acid ceramidase inhibitors. In some embodiments, the inhibitors do not induce permanent lysosomal destabilization or proteolytic degradation of acid ceramidase. The inhibitors include N-(ω-aminoacyl)aminophenylalcohols as well as aminoester prodrugs of N-acylaminophenyl alcohols. The inhibitors can be used to treat and/or prevent diseases related to undesirable ceramidase and ceramidase-related activities, including cancer and other proliferative diseases.

BACKGROUND

The stimulus-controlled pathways of sphingolipid metabolism provide a rich network of bioactive molecules with pivotal roles in the regulation of diverse cell functions. Sphingolipid metabolites, namely ceramide (Cer) and sphingosine 1-phosphate (S1P), are increasingly being recognized for their role as signaling molecules involved in regulation of survival, proliferation and cell death. In particular, the cellular balance between Cer and S1P seems to play a role in a cell's decision to either undergo apoptosis or proliferate, two events which are implicated in tumor development and growth. Whereas Cer possesses pro-apoptotic capacity in many cell types, S1P acts as a counter player able to induce cell proliferation and protect cells from undergoing apoptosis. Therefore, tipping the balance in favor of Cer production, i.e., by inhibiting ceramidase (CDase) or sphingosine kinase (SK) activities has potential to support its pro-apoptotic action and represents a promising rational approach to effective cancer therapy. See Ogretmen and Hannun, *Nat. Rev. Cancer*, 4, 604-616 (2004); and Huwiler and Zanaemeister-Wittke, *Oncology Hematol.*, 63, 150-159 (2007).

Acid ceramidase (ACDase or AC), a lysosomal enzyme, catabolizes Cer into sphingosine (Sph), a substrate for SK, and free fatty acids at an optimal pH of approximately 4.5, distinguishing it from other CDases. Sph released by the action of ACDase can serve as a substrate for SK to form S1P or as a substrate for ceramide synthases to resynthesize new Cers. See Bielawska et al., *Bioorg. Med. Chem.*, 16, 1032-1045 (2008). ACDase represents a new target for cancer therapy because of its role in regulating the Cer-Sph-S1P inter-metabolism. Levels of ACDase have been shown to be elevated in many tumor cell lines. See Elojeimy et al., *Mol. Ther.*, 15, 1259-1263 (2007). Inhibition of ACDase activity leads to elevation of intracellular $C_{16}$-, $C_{14}$-, and $C_{18}$-Cers, decrease of Sph and S1P, and stimulation of apoptotic cell death. See Bielawska et al., *Bioorg. Med. Chem.*, 16, 1032-1045 (2008). Thus, ACDase has become a target in cancer therapy, and its inhibitors act as chemotherapeutic agents on several types of cancers. See Liu et al., *Front. Biosci.*, 13, 2293-2298 (2008); and Szulc et al., *Bioorg. Med. Chem.*, 16, 1015-1031 (2008).

Accordingly, there is an ongoing need for novel ACDase inhibitors, ideally having one or more of the following properties: easily delivered to cells, accumulate preferentially in the lysosomal compartment where ACDase is present, and do not cause permanent damage to the lysosomal compartment.

SUMMARY

The presently disclosed subject matter provides, in some embodiments, a compound for inhibiting acid ceramidase wherein the inhibiting can be free of permanent lysosomal destabilization and/or proteolytic degradation of the acid ceramidase, wherein the compound has a structure of Formula (Ia):

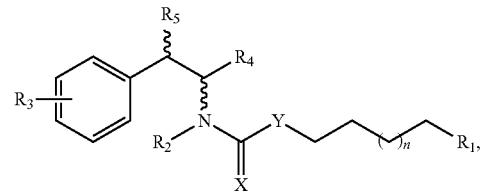

wherein:

n is an integer from 0 to 13;

$R_1$ is selected from the group comprising $NH_2$, $NHR_6$, $NR_6R_7$, and N-heterocycle;

$R_2$ is selected from the group comprising H and alkyl;

$R_3$ is selected from the group comprising H, OH, $NO_2$, $NH_2$ and $NHR_9$;

$R_4$ is selected from the group comprising H, $CH_3$, $CH_2OH$, and $CH_2O$—$C(=O)$—$CH(R_8)NR_6R_7$;

$R_5$ is selected from the group comprising H, OH, =O, and $OC(=O)CH(R_8)NR_6R_7$ each $R_6$, $R_7$, and $R_8$ is independently selected from the group comprising H, alkyl, aralkyl, and aryl;

$R_9$ is $C(=O)$—$(CH_2)_mR_{10}$, wherein m is an integer from 5 to 10;

$R_{10}$ is H, alkyl, cycloalkyl, or heterocycle;

X is selected from the group comprising O, NH, and S; and

Y is $CH_2$ or NH;

or a pharmaceutically acceptable salt thereof.

In some embodiments, X is O. In some embodiments, Y is $CH_2$. In some embodiments, $R_2$ is H. In some embodiments, $R_3$ is $NO_2$. In some embodiments, $R_4$ is $CH_2OH$. In some embodiments, $R_5$ is OH. In some embodiments, n is 7. In some embodiments, $R_1$ is $NHR_6$ wherein $R_6$ is alkyl. In some embodiments, $R_1$ is $NR_6R_7$ wherein $R_6$ and $R_7$ are each alkyl. In some embodiments, $R_1$ is N-heterocycle selected from the group comprising:

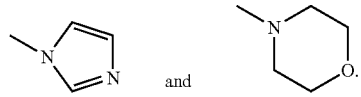

In some embodiments, the compound is selected from the group comprising: (1R,2R)-2-[N-(12'-{1''-imidazol}-dodecanoyl)-amino]-1-(4''-nitrophenyl)-1,3-propandiol (LCL433); (1R,2R)-2-[N-(12'-{1''-morpholine}-dodecanoyl)-amino]-1-(4''-nitrophenyl)-1,3-propandiol (LCL449); (1R,2R)-2-[N-(12'-amino-dodecanoyl)-amino]-1-(4''-nitrophenyl)-1,3-propandiol (LCL463); (1R,2R)-2-[N-(12'-N,N-dimethylamino-dodecanoyl)-amino]-1-(4''-nitrophenyl)-1,3-propandiol (LCL464); (1R,2R)-2-[N-(6'-{N-octylamino}-hexanoyl)-amino]-1-(4''-nitrophenyl)-1,3-propandiol (LCL488); and (1R,2R)-2-[N-{12'-N-methylamino}-dodecanoyl)-amino]-1-(4''-nitrophenyl)-1,3-propandiol (LCL506). In some embodiments, the compound is (1R,2R)-2-[N-(12'-N,N-dimethylamino-dodecanoyl)-amino]-1-(4''-nitrophenyl)-1,3-propandiol (LCL464).

In some embodiments, the presently disclosed subject matter provides a pharmaceutical composition comprising: (a) a compound of Formula (Ia) and (b) a pharmaceutically acceptable carrier.

In some embodiments, the presently disclosed subject matter provides a compound of Formula (Ib):

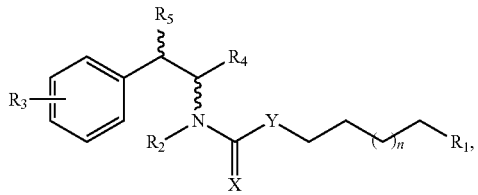

wherein:
n is an integer from 0 to 13;
$R_1$ is selected from the group comprising H, OH, SH, $NH_2$, Cl, Br, I, C(=O)OH, C(=O)$NH_2$, NH(C=NH)$NH_2$, $NHR_6$, $NR_6R_7$, $^+N(R_6)_3$ and N-heterocycle;
$R_2$ is selected from the group comprising H and alkyl;
$R_3$ is selected from the group comprising H, OH, $NO_2$, $NH_2$ and $NHR_9$;
$R_4$ is selected from the group comprising H, $CH_3$, $CH_2OH$, and $CH_2O$—C(=O)—CH($R_8$)$NR_6R_7$;
$R_5$ is selected from the group comprising H, OH, =O, and OC(=O)CH($R_8$)$NR_6R_7$
each $R_6$, $R_7$, and $R_8$ is independently selected from the group comprising H, alkyl, aralkyl, and aryl;
$R_9$ is C(=O)—(CH_2)_mR_{10}$, wherein m is an integer from 5 to 10;
$R_{10}$ is H, alkyl, cycloalkyl, or heterocycle;
X is selected from the group comprising O, NH, and S;
Y is $CH_2$ or NH; and
wherein at least one of $R_4$ and $R_5$ comprises an ester moiety;
or a pharmaceutically acceptable salt thereof.

In some embodiments, $R_4$ is $CH_2O$—C(=O)—CH($R_8$)$NR_6R_7$. In some embodiments, $R_8$ is H and $R_6$ and $R_7$ are each alkyl.

In some embodiments, $R_5$ is OC(=O)CH($R_8$)$NR_6R_7$. In some embodiments, $R_8$ is H, and $R_6$ and $R_7$ are each alkyl.

In some embodiments, $R_4$ is $CH_2O$—C(=O)—CH($R_8$)$NR_6R_7$ and $R_5$ is OC(=O)—CH($R_8$)$NR_6R_7$. In some embodiments, n is 5. In some embodiments, $R_1$ is n-butyl. In some embodiments, $R_3$ is $NO_2$.

In some embodiments, the compound is selected from

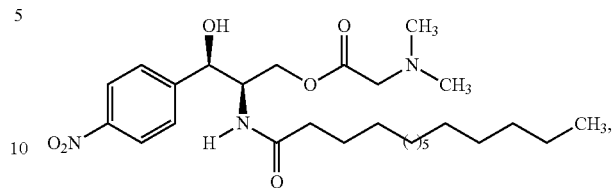

(LCL522)

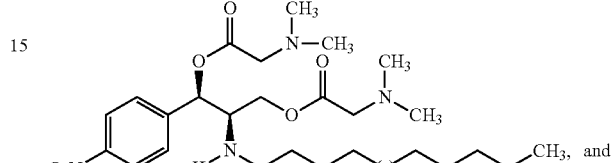

(LCL521)

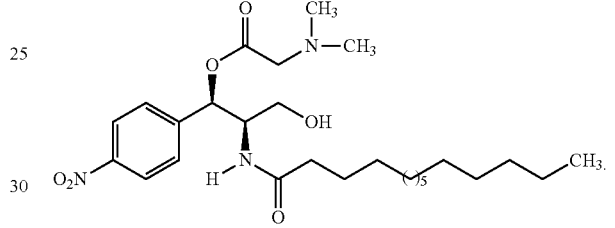

(LCL581)

In some embodiments, the presently disclosed subject matter provides a pharmaceutical composition comprising: (a) a compound of Formula (Ib) and (b) a pharmaceutically acceptable carrier.

In some embodiments, the presently disclosed subject matter provides a method of inhibiting acid ceramidase, the method comprising contacting a sample comprising acid ceramidase with an effective amount of a compound of Formula (Ia):

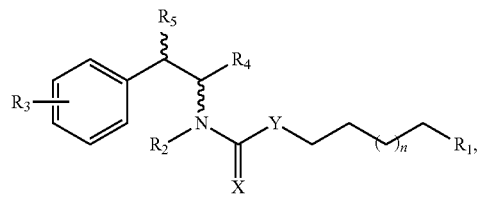

wherein:
n is an integer from 0 to 13;
$R_1$ is selected from the group comprising $NH_2$, $NHR_6$, $NR_6R_7$, and N-heterocycle;
$R_2$ is selected from the group comprising H and alkyl;
$R_3$ is selected from the group comprising H, OH, $NO_2$, $NH_2$ and $NHR_9$;
$R_4$ is selected from the group comprising H, $CH_3$, $CH_2OH$, and $CH_2O$—C(=O)—CH($R_8$)$NR_6R_7$;
$R_5$ is selected from the group comprising H, OH, =O, and OC(=O)CH($R_8$)$NR_6R_7$
each $R_6$, $R_7$, and $R_8$ is independently selected from the group comprising H, alkyl, aralkyl, and aryl;
$R_9$ is C(=O)—$(CH_2)_mR_{10}$, wherein m is an integer from 5 to 10;
$R_{10}$ is H, alkyl, cycloalkyl, or heterocycle;

X is selected from the group comprising O, NH, and S; and

Y is CH$_2$ or NH;

or a pharmaceutically acceptable salt thereof; wherein the inhibiting is free of permanent lysosomal destabilization and/or proteolytic degradation of the acid ceramidase. In some embodiments, the sample is an in vitro cell sample or an in vivo cell sample.

In some embodiments, the presently disclosed subject matter provides a method of treating or preventing a disease or disorder associated with undesirable ceramidase or sphingosine kinase activity in a subject, the method comprising administering to the subject an effective amount of a compound of Formula (Ia):

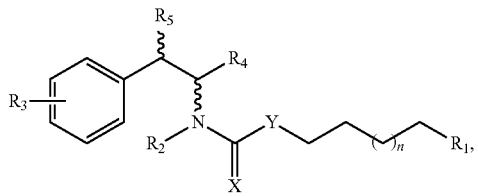

wherein:

n is an integer from 0 to 13;

R$_1$ is selected from the group comprising NH$_2$, NHR$_6$, NR$_6$R$_7$, and N-heterocycle;

R$_2$ is selected from the group comprising H and alkyl;

R$_3$ is selected from the group comprising H, OH, NO$_2$, NH$_2$ and NHR$_9$;

R$_4$ is selected from the group comprising H, CH$_3$, CH$_2$OH, and CH$_2$O—C(=O)—CH(R$_8$)NR$_6$R$_7$;

R$_5$ is selected from the group comprising H, OH, =O, and OC(=O)CH(R$_8$)NR$_6$R$_7$ each R$_6$, R$_7$, and R$_8$ is independently selected from the group comprising H, alkyl, aralkyl, and aryl;

R$_9$ is C(=O)—(CH$_2$)$_m$R$_{10}$, wherein m is an integer from 5 to 10;

R$_{10}$ is H, alkyl, cycloalkyl, or heterocycle;

X is selected from the group comprising O, NH, and S; and

Y is CH$_2$ or NH;

or a pharmaceutically acceptable salt thereof; wherein said compound inhibits acid ceramidase without or substantially without permanent lysosomal destabilization and/or proteolytic degradation of the acid ceramidase.

In some embodiments, the disease or disorder is selected from the group comprising cancer, cancer metastasis, atherosclerosis, stenosis, inflammation, asthma, atopic dermatitis and other proliferative diseases. In some embodiments, the subject is a mammalian subject. In some embodiments, the compound of Formula (Ia) is administered to the subject in a pharmaceutical formulation comprising the compound of Formula (Ia) and a pharmaceutically acceptable carrier.

In some embodiments, the presently disclosed subject matter provides a method of treating cancer, the method comprising administering to a subject in need of treatment thereof an effective amount of a compound of Formula (Ia):

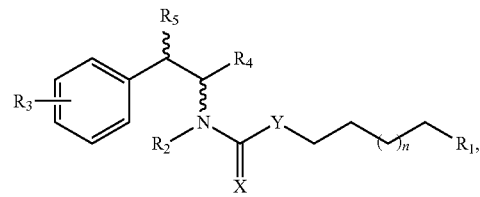

wherein:

n is an integer from 0 to 13;

R$_1$ is selected from the group comprising NH$_2$, NHR$_6$, NR$_6$R$_7$, and N-heterocycle;

R$_2$ is selected from the group comprising H and alkyl;

R$_3$ is selected from the group comprising H, OH, NO$_2$, NH$_2$ and NHR$_9$;

R$_4$ is selected from the group comprising H, CH$_3$, CH$_2$OH, and CH$_2$O—C(=O)—CH(R$_8$(NR$_6$R$_7$;

R$_5$ is selected from the group comprising H, OH, =O, and OC(=O)CH(R$_8$)NR$_6$R$_7$ each R$_6$, R$_7$, and R$_8$ is independently selected from the group comprising H, alkyl, aralkyl, and aryl;

R$_9$ is C(=O)—(CH$_2$)$_m$R$_{10}$, wherein m is an integer from 5 to 10;

R$_{10}$ is H, alkyl, cycloalkyl, or heterocycle;

X is selected from the group comprising O, NH, and S; and

Y is CH$_2$ or NH;

or a pharmaceutically acceptable salt thereof.

In some embodiments, the cancer is selected from the group comprising breast cancer, prostate cancer, melanoma, alveolar cancer, and head and neck cancer. In some embodiments, the subject is a mammalian subject. In some embodiments, the compound of Formula (Ia) is administered in a pharmaceutical formulation comprising the compound of Formula (Ia) and a pharmaceutically acceptable carrier.

In some embodiments, X is O. In some embodiments, Y is CH$_2$. In some embodiments, R$_2$ is H. In some embodiments, R$_3$ is NO$_2$. In some embodiments, R$_4$ is CH$_2$OH. In some embodiments, R$_5$ is OH. In some embodiments, n is 7.

In some embodiments, R$_1$ is NHR$_6$ wherein R$_6$ is alkyl. In some embodiments, R$_1$ is NR$_6$R$_7$ wherein R$_6$ and R$_7$ are each alkyl. In some embodiments, R$_1$ is N-heterocycle selected from the group comprising:

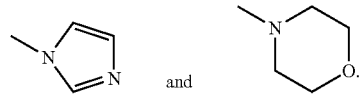

In some embodiments, the compound is selected from the group comprising: (1R,2R)-2-[N-(12'-{1"-imidazol}-dodecanoyl)-amino]-1-(4"-nitrophenyl)-1,3-propandiol (LCL433); (1R,2R)-2-[N-(12'-{1"-morpholine}-dodecanoyl)-amino]-1-(4"-nitrophenyl)-1,3-propandiol (LCL449); (1R,2R)-2-[N-(12'-amino-dodecanoyl)-amino]-1-(4"-nitrophenyl)-1,3-propandiol (LCL463); (1R,2R)-2-[N-(12'-N,N-dimethylamino-dodecanoyl)-amino]-1-(4"-nitrophenyl)-1,3-propandiol (LCL464); (1R,2R)-2-[N-(6'-{N-octylamino}-hexanoyl)-amino]-1-(4"-nitrophenyl)-1,3-propandiol (LCL488); and (1R,2R)-2-[N-{12'-N-methylamino}-dodecanoyl)-amino]-1-(4"-nitrophenyl)-1,3-propandiol (LCL506). In some embodiments, the compound is (1R,2R)-2-[N-(12'-N,N-dimethylamino-dodecanoyl)-amino]-1-(4"-nitrophenyl)-1,3-propandiol (LCL464).

In some embodiments, the presently disclosed subject matter provides a method of inhibiting acid ceramidase, the method comprising contacting a sample comprising acid ceramidase with an effective amount of an ester prodrug of an acid ceramidase inhibitor, under conditions wherein the prodrug is hydrolyzed to provide the inhibitor, the prodrug having a structure of Formula (Ib):

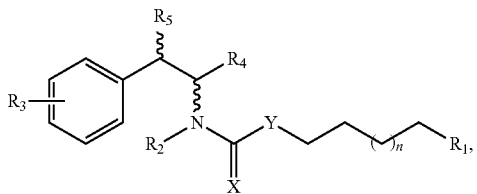

wherein:
n is an integer from 0 to 13;
$R_1$ is selected from the group comprising H, OH, SH, $NH_2$, Cl, Br, I, C(=O)OH, C(=O)$NH_2$, NH(C=NH)$NH_2$, $NHR_6$, $NR_6R_7$, $^+N(R_6)_3$ and N-heterocycle;
$R_2$ is selected from the group comprising H and alkyl;
$R_3$ is selected from the group comprising H, OH, $NO_2$, $NH_2$ and $NHR_9$;
$R_4$ is selected from the group comprising H, $CH_3$, $CH_2OH$, and $CH_2O$—C(=O)—CH($R_8$)$NR_6R_7$;
$R_5$ is selected from the group comprising H, OH, =O, and OC(=O)CH($R_8$)$NR_6R_7$
each $R_6$, $R_7$, and $R_8$ is independently selected from the group comprising H, alkyl, aralkyl, and aryl;
$R_9$ is C(=O)—$(CH_2)_m R_{10}$, wherein m is an integer from 5 to 10;
$R_{10}$ is H, alkyl, cycloalkyl, or heterocycle;
X is selected from the group comprising O, NH, and S;
Y is $CH_2$ or NH; and
wherein at least one of $R_4$ and $R_5$ comprises an ester moiety;
or a pharmaceutically acceptable salt thereof.

In some embodiments, the sample is an in vitro cell sample or an in vivo cell sample.

In some embodiments, the presently disclosed subject matter provides a method of treating or preventing a disease or disorder associated with undesirable ceramidase or sphingosine kinase activity in a subject, the method comprising administering to the subject an effective amount of a compound of Formula (Ib):

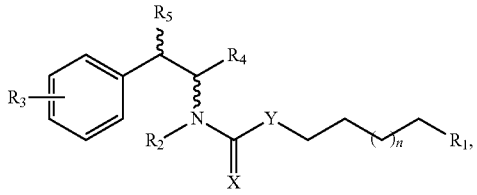

wherein:
n is an integer from 0 to 13;
$R_1$ is selected from the group comprising H, OH, SH, $NH_2$, Cl, Br, I, C(=O)OH, C(=O)$NH_2$, NH(C=NH)$NH_2$, $NHR_6$, $NR_6R_7$, $^+N(R_6)_3$ and N-heterocycle;
$R_2$ is selected from the group comprising H and alkyl;
$R_3$ is selected from the group comprising H, OH, $NO_2$, $NH_2$ and $NHR_9$;
$R_4$ is selected from the group comprising H, $CH_3$, $CH_2OH$, and $CH_2O$—C(=O)—CH($R_8$)$NR_6R_7$;
$R_5$ is selected from the group comprising H, OH, =O, and OC(=O)CH($R_8$)$NR_6R_7$
each $R_6$, $R_7$, and $R_8$ is independently selected from the group comprising H, alkyl, aralkyl, and aryl;
$R_9$ is C(=O)—$(CH_2)_m R_{10}$, wherein m is an integer from 5 to 10;
$R_{10}$ is H, alkyl, cycloalkyl, or heterocycle;
X is selected from the group comprising O, NH, and S;
Y is $CH_2$ or NH; and
wherein at least one of $R_4$ and $R_5$ comprises an ester moiety;
or a pharmaceutically acceptable salt thereof.

In some embodiments, the disease or disorder is selected from the group comprising cancer, cancer metastasis, atherosclerosis, stenosis, inflammation, asthma, atopic dermatitis and other proliferative diseases. In some embodiments, the subject is a mammalian subject. In some embodiments, the compound of Formula (Ib) is administered to the subject in a pharmaceutical formulation comprising the compound of Formula (Ib) and a pharmaceutically acceptable carrier.

In some embodiments, the presently disclosed subject matter provides a method of treating cancer, the method comprising administering to a subject in need of treatment thereof an effective amount of a compound of Formula (Ib):

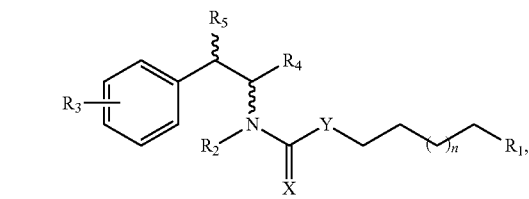

wherein:
n is an integer from 0 to 13;
$R_1$ is selected from the group comprising H, OH, SH, $NH_2$, Cl, Br, I, C(=O)OH, C(=O)$NH_2$, NH(C=NH)$NH_2$, $NHR_6$, $NR_6R_7$, $^+N(R_6)_3$ and N-heterocycle;
$R_2$ is selected from the group comprising H and alkyl;
$R_3$ is selected from the group comprising H, OH, $NO_2$, $NH_2$ and $NHR_9$;
$R_4$ is selected from the group comprising H, $CH_3$, $CH_2OH$, and $CH_2O$—C(=O)—CH($R_8$)$NR_6R_7$;
$R_5$ is selected from the group comprising H, OH, =O, and OC(=O)CH($R_8$)$NR_6R_7$
each $R_6$, $R_7$, and $R_8$ is independently selected from the group comprising H, alkyl, aralkyl, and aryl;
$R_9$ is C(=O)—$(CH_2)_m R_{10}$, wherein m is an integer from 5 to 10;
$R_{10}$ is H, alkyl, cycloalkyl, or heterocycle;
X is selected from the group comprising O, NH, and S;
Y is $CH_2$ or NH; and
wherein at least one of $R_4$ and $R_5$ comprises an ester moiety;
or a pharmaceutically acceptable salt thereof.

In some embodiments, the subject is a mammalian subject. In some embodiments, the compound of Formula (Ib) is administered in a pharmaceutical formulation comprising the compound of Formula (Ib) and a pharmaceutically acceptable carrier.

In some embodiments, $R_4$ is $CH_2O$—C(=O)—CH($R_8$)$NR_6R_7$. In some embodiments, $R_8$ is H and $R_6$ and $R_7$ are each alkyl.

In some embodiments, $R_5$ is $OC(=O)CH(R_8)NR_6R_7$. In some embodiments, $R_8$ is H, and $R_6$ and $R_7$ are each alkyl.

In some embodiments, $R_4$ is $CH_2O—C(=O)—CH(R_8)NR_6R_7$ and $R_5$ is $OC(=O)—CH(R_8)NR_6R_7$.

In some embodiments, n is 5. In some embodiments, $R_1$ is n-butyl. In some embodiments, $R_3$ is $NO_2$.

In some embodiments, the compound is selected from:

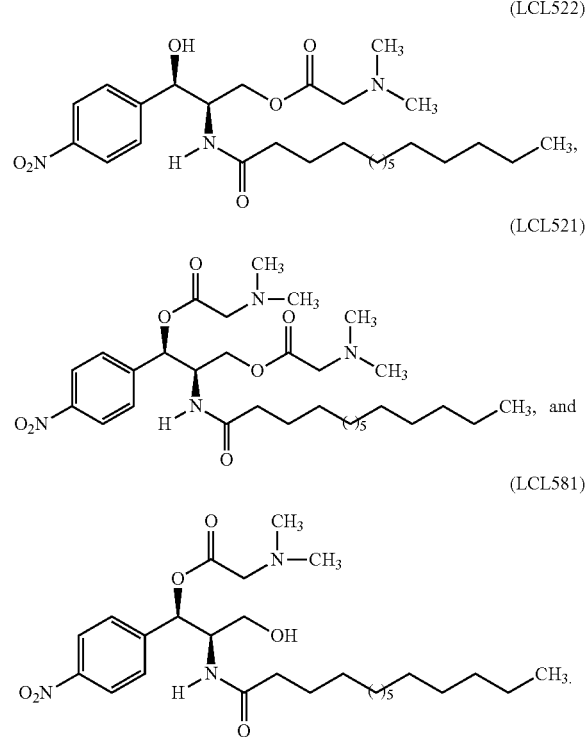

It is an object of the presently disclosed subject matter to provide lysosomotropic ACDase inhibitors and related prodrugs for use in treating or preventing diseases and disorders related to undesirable ceramidase, ceramidase-related (such as ceramidase reverse activity, ceramide/dhceramide synthases and acyl-transferases), and/or sphingosine kinase activity, including cancer and other proliferative diseases.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

DETAILED DESCRIPTION

Figure 1:
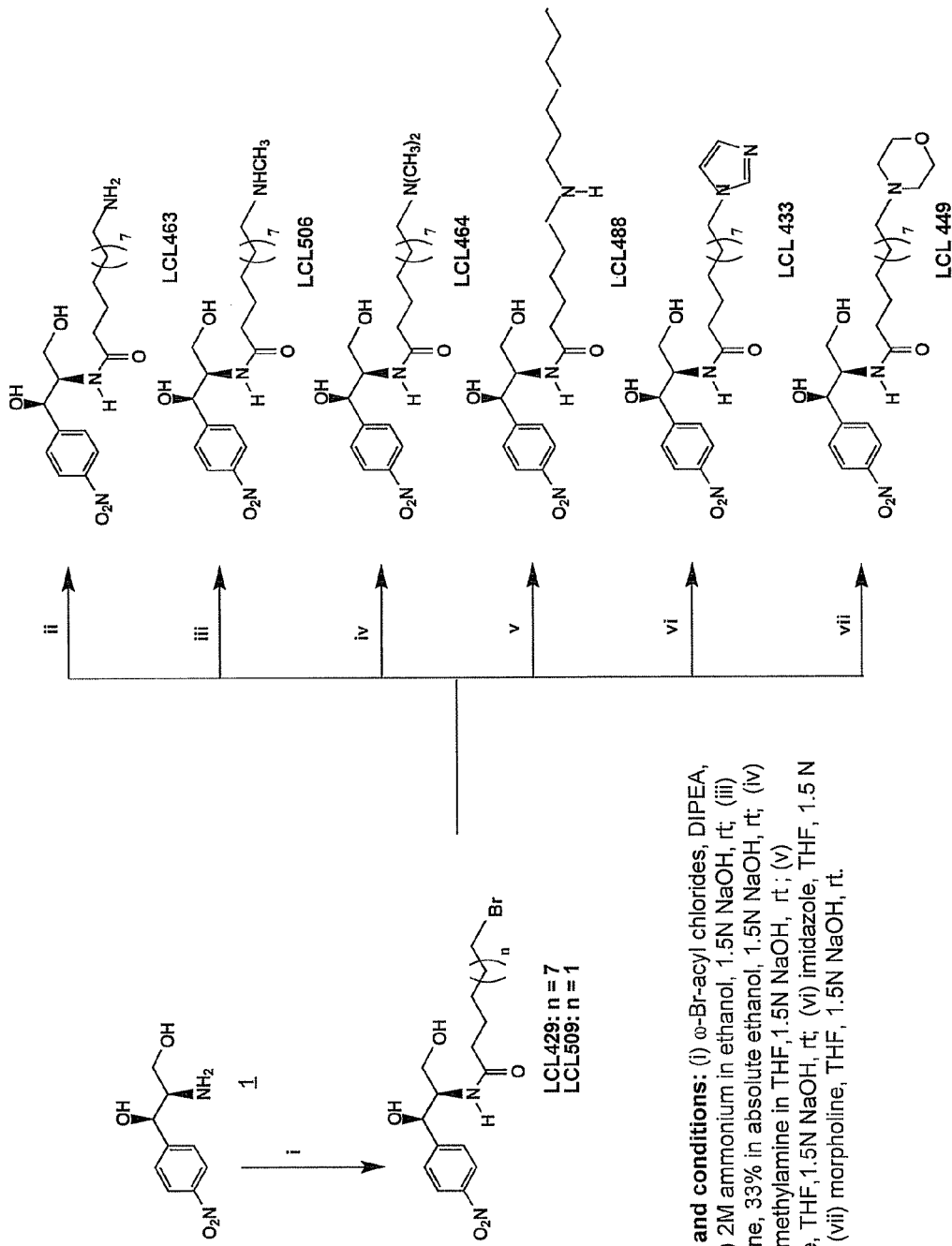
FIG. 1 is a schematic drawing showing the synthesis of Class E compounds (LCL463, LCL506, LCL464, LCL488, LCL433, and LCL449) that include ω-aminoacyl groups.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

All references cited herein, including all patents, patent applications, database entries, and journal articles, are incorporated herein by reference in their entireties and for all purposes to the same extent as if each individual patent, patent application, database entry, or journal article was specifically and individually indicated to be incorporated by reference in its entirety for all purposes.

I. Lysomotropic Acid Ceramidase Inhibitors

Ceramides are known to regulate anti-proliferative responses, such as apoptosis, growth arrest, differentiation, and senescence in various human cancer cell lines. Many important biological targets and events related to ceramide actions in cells have been identified, namely, activation of phosphatases, kinases, and caspases; inhibition of the telomerase enzyme complex; induction of the transmembrane signaling pathways and release of cytochrome c from mitochondria. Among the shortcomings of the use of ceramides as perspective anticancer agents are very low water solubility, low cellular uptake, uncontrolled delivery, release, and intracellular targeting. Ceramidase is an enzyme which hydrolyzes ceramide and decreases its level in cells. Inhibition of ceramidase increases the level of endogenous ceramide and inhibitors of this enzyme are exploited as candidates for drug discovery.

The family of ceramidases includes acid, neutral, and alkaline species See Koch et al., *J. Bio. Chem.*, 271, 33110-33115 (1996); E I Bawab et al., *J. Bio. Chem.*, 274, 27948-27955 (1999); and Mao et al., *J. Bio. Chem.*, 276, 26577-26588 (2001). Human acid ceramidase maps to 8p22, which is frequently altered in prostate cancer (PCa). This enzyme catalyses the hydrolysis of ceramide to sphingosine and free fatty acids, the overall effect of which is downregulation of ceramide signaling (i.e., decreased apoptosis) and increased pools of sphingosine, which can be phosphorylated by sphingosine kinase to generate S1P. S1P interacts with the endothelial differentiation gene family (Edg/S1P receptors) to promote endothelial cell migration and angiogenesis. Thus, a cell (e.g., a tumor cell) that over-expresses ceramidase can generate an anti-apoptotic phenotype and a potential increase in angiogenesis in its microenvironment.

The PCa cell lines DU145, PC3, and LNCaP all show elevated levels of ceramidase mRNA by Northern blotting. Prostate tumors, obtained from radical prostatectomies, demonstrated that 4.1.6% had increased levels of acid ceramidase mRNA, 55.5% had no change, and 2.7% had a decrease in acid ceramidase mRNA when analyzed for acid ceramidase expression by a competitive PCR approach. Thus, a significant fraction of tumors in prostate cancer have the potential to assume an anti-apoptotic phenotype.

In most cancer cells, including PCa cells, ceramide causes activation of caspases, DNA fragmentation, and other characteristics and hallmarks of apoptosis, induction of the stress-activated protein kinases (SAPK/JNK), inhibition of phospholipase D, dephosphorylation and inactivation of protein kinase C (PKC), enhanced release of mitochondrial reactive oxygen species, release of cytochrome c, and activation of PP1, which dephosphorylates SR proteins leading to a more pro-apoptotic phenotype.

Mechanistically, a coordinated picture of cell growth regulation involving ceramide and other key regulators of cell cycle progression and apoptosis is emerging. Thus, the formation of ceramide in response to TNF and other, but not all, inducers requires activation of upstream caspases (e.g., caspase 8), which are inhibited by YVAD and by Crm A. However, inhibitors of downstream caspases fail to prevent ceramide formation and yet ceramide activates downstream caspases (e.g., caspase 3) but not upstream caspases. Moreover, the ability of ceramide to induce apoptosis is blocked by inhibitors of the executioner caspases but not effector caspases placing ceramide formation between the two sets of enzymes. Also, studies with Bcl-2 show that Bcl-2 is downstream of ceramide in the same pathway. Thus, ceramide regulates phosphorylation of Bcl-2 and the action of ceramide on cell death is inhibited by Bcl-2 over expression.

In all these actions, short chain ceramides ($C_2$-$C_8$) can exhibit a level of potency consistent with levels of endogenous ceramides (i.e., long-chain ceramides, $C_{16}$-$C_{24}$). The action of ceramide analogs can exhibit significant specificity. For, example, the closely related neutral lipid, diacylglycerol (DAG), not only does not mimic the action of ceramide, but more often antagonizes it. Dihydroceramide, which is the metabolic precursor to ceramide and differs from it only in that it lacks the 4-5 trans double bond, exhibits no activity in cellular studies, although it shows similar levels of uptake. See Bielawska et al., *J. Bio. Chem.*, 268, 26226-26232 (1993); and Bielawska et al., *J. Bio. Chem.*, 267, 18493-18497 (1992).

In contrast, short chain ceramides can be poor effectors of other key actions associated with TNF and other inducers of ceramide formation. Notably, ceramide is not active in inducing NF-κB, a transcription factor that plays a role in the inflammatory and anti-apoptotic function of TNF. Also, ceramide is a poor activator of erk members of the MAP kinase family, especially when compared with sphingosine and sphingosine-1-phosphate. This restricted action of short chain ceramides to a subset of biochemical targets in cytokine responses provides further impetus to the emerging hypothesis of a more specific function for ceramide in the regulation of apoptosis in cancer.

Multiple lines of evidence point to a role for ceramide in mediating Fas-induced apoptosis. First, ceramide generation has been demonstrated to be an integral part of Fas-induced apoptosis. See Cremesti et al., *J. Bio. Chem.*, 276, 23954-23961 (2001). Second, Fas activation has been shown to activate acid sphingomyelinase (ASmase), which was demonstrated to be involved in propagation of Fas-generated apoptotic signaling. See Raisova et al., *FEBS Lett.*, 473, 27-32 (2000). Third, Fas-induced ceramide formation acts in conjunction with caspase activation and is not a consequence of apoptosis. See Tepper et al., J. Bio. Chem., 272, 24308-24312 (1997). Fourth, Fas-resistant cells demonstrate insignificant changes in ceramide levels yet have normal receptor expression and intact downstream signaling. See Tepper et al., *Proc. Natl. Acad. Sci., USA*, 92, 8443-8447 (1995). Fifth, a role for *de novo* ceramide synthesis has also been established in Fas-induced apoptosis (see Chalfant et al., J. Bio. Chem., 276, 44848-44855 (2001)) suggesting two possible "pools" of ceramide can affect Fas signal transduction. Sixth, acid sphingomyelinase null hepatocytes are insensitive to J02-induced capping but are sensitized with a 25 nM dose of $C_{16}$-ceramide.

Although not necessarily directly causative for prostate cancer development, acid ceramidase elevation in 41% of human tumors (60% of Gleeson grade 7 and only 38% of grade 6 tumors) would suggest that its expression provides a selective advantage for tumor growth. The mechanism is likely manifested in two ways. First, reduced levels of ceramide have an anti-apoptotic effect and downregulation of apoptosis is clearly a hallmark of some cancer, including the prostate. Second, S1P production, via increased sphingosine kinase, has an angiogenic and growth effect as well as promoting endothelial cell migration in the prostate.

The presently disclosed subject matter relates in some embodiments to amphiphilic, lysosomotropic ACDase inhibitors and related prodrugs for targeting cellular ACDase. In some embodiments, the presently disclosed subject matter relates to compounds of Formula (I):

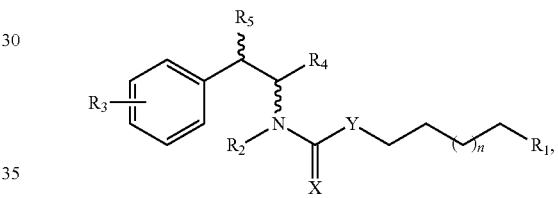

wherein:

n is an integer from 0 to 13;

$R_1$ is selected from the group comprising H, OH, SH, $NH_2$, Cl, Br, I, C(=O)OH, C(=O)$NH_2$, NH(C=NH)$NH_2$, $NHR_6$, $NR_6R_7$, $^+N(R_6)_3$ and N-heterocycle;

$R_2$ is selected from the group comprising H and alkyl;

$R_3$ is selected from the group comprising H, OH, $NO_2$, $NH_2$ and $NHR_9$;

$R_4$ is selected from the group comprising H, $CH_3$, $CH_2OH$, and $CH_2O$—C(=O)—CH($R_8$)$NR_6R_7$;

$R_5$ is selected from the group comprising H, OH, =O, and OC(=O)CH($R_8$)$NR_6R_7$ each $R_6$, $R_7$, and $R_8$ is independently selected from the group comprising H, alkyl, aralkyl, and aryl;

$R_9$ is C(=O)—$(CH_2)_m R_{10}$, wherein m is an integer from 5 to 10;

$R_{10}$ is H, alkyl, cycloalkyl, or heterocycle;

X is selected from the group comprising O, NH, and S;

Y is $CH_2$ or NH; and wherein at least one of $R_4$ and $R_5$ comprises an ester moiety or wherein $R_1$ is selected from the group consisting of $NH_2$, $NHR_6$, $NR_6R_7$, and N-heterocycle.

Thus, the presently disclosed subject matter relates to compounds (also referred to herein as Class E compounds) that include 2-N-(ω-amino-acyl)-amino-phenyl alcohols, as well as compounds that are prodrugs of B13 (and analogs thereof). The structure of B13 is shown below in Scheme 1.

Scheme 1. Structure of B13.

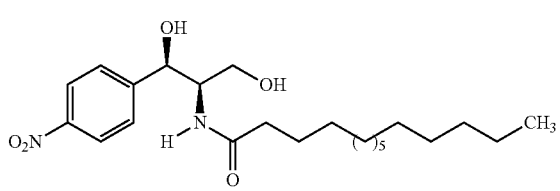

In some embodiments, the compounds of Formula (I) can combine an amide group or other N-acyl group, to provide molecular recognition of the compound by ACDase, and an amino function, for selective targeting of the lysosomal compartment. The compounds can include varied hydrocarbon chains in their N-acyl or modified N-acyl (e.g., urea, thiourea, thioamide, etc.) chains, varying functionality of the amino groups (e.g., primary amine, secondary amine, tertiary amine or N-heterocycle) incorporated into those N-acyl-parts, different amino acid moieties attached to the oxygen atoms of the hydroxyl groups, and methylene phosphate groups attached to the amino groups (including amino and/or hydroxyl group substituents of the phenyl ring). The compounds can include any stereochemistry.

The compounds can also including amino acid ester prodrugs that, in some embodiments, can act as lysosomotropic prodrugs which can be easily delivered to cells to accumulate preferentially in lysosomes, and are expected to release free inhibitors into the lysosomes. See Vig et al., *Pharm. Res.,* 20, 1381-1388 (2003); Rautio et al., *Nat. Rev. Drug Discov.,* 7, 255-270 (2008); Song et al., *J. Med. Chem.,* 49, 4344-4355 (2006); Black and Percival, *Chembiochem,* 7, 1525-1535 (2006); Jones-Bolin et al., *Mol. Cancer Ther.,* 5, 1744-1753 (2006); and Kaufmann and Krise, *J. Pharmaceutical. Sci.,* 96, 729-746 (2007). For example, the prodrugs of B13 can include one or more aminoester groups formed by esterification of a free hydroxyl group of B13.

The presently disclosed compounds can be used for inducing cellular differentiation, inducing apoptosis, and altering cell growth and cell phenotype. These compounds can also be used in treating diseases characterized by hyperproliferation or migration of cells, including the treatment of cancers and other proliferative diseases. The presently disclosed subject matter provides in some embodiments the combining of structural elements of B13 with an amino function for targeting lysosomes to provide potent lysosomal inhibitors of ACDase without causing any significant lysosomal dysfunction or degradation of the ACDase.

Exemplary Class E compounds that include a ω-aminoacyl group and their synthesis are shown in FIG. 1. Class E compounds, such as LCL464, i.e., (1R,2R)-2-(12'-N,N-dimethyldodecanoylamino)-1-(4'-nitrophenyl)-1,3-propandiol, appear to affect the flux between endogenous Cer, Sph, and S1P causing an early (e.g., within two hour) and specific increase of endogenous $C_{14}$-Cer and a decrease in Sph consistent with the inhibition of ACDase. Extended treatments, especially at higher concentrations, cause a specific increase of $C_{18}$-Cer. These two Cers ($C_{14}$-Cer and $C_{18}$-Cer) have previously been shown to act as pro-apoptoticagents. See Bielawska et al., *Bioorg. Med. Chem.,* 16, 1032-1045 (2008); and Karahatav et al., *Cancer Lett.,* 256, 101-111 (2007). Thus, the activities of the presently disclosed compounds suggest that LCL464, or its close relatives, can act as chemotherapeutic agents affecting ACDase.

Figure 14A:
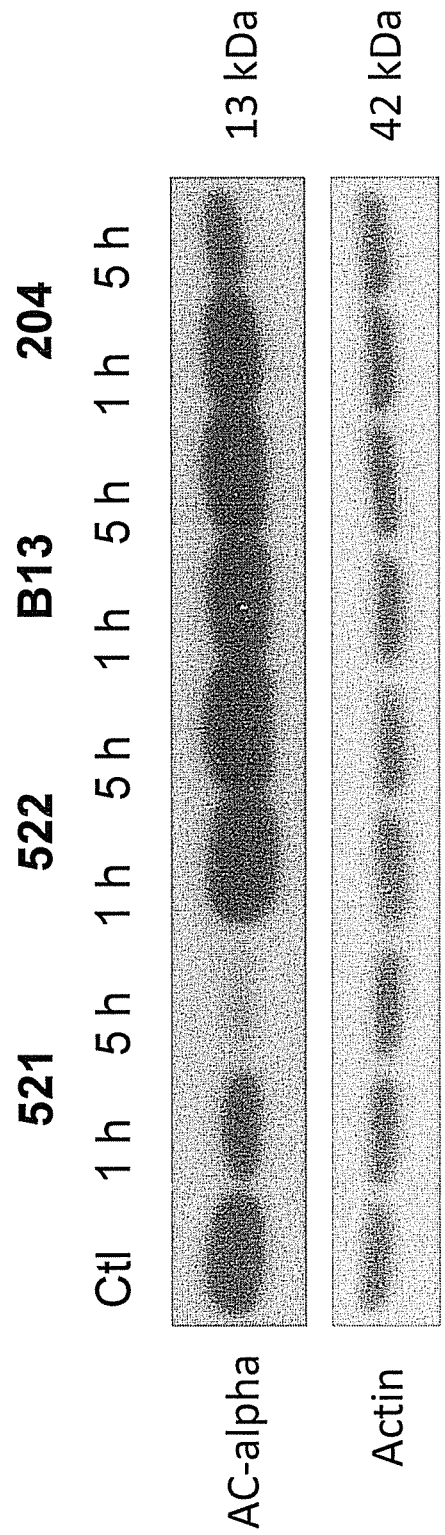
FIG. 14A is a pair of micrographs of Western blot analysis showing the effects of 1 hour and 5 hour treatment with Class E prodrugs LCL521 and LCL522 on acid ceramidase (AC) stability as determined by staining for AC in cell lysates. Results for (1R,2R)-2-N-(tetradecanoylamino)-1-(4'-nitrophenyl)-1,3-propandiol (B13) and (1R,2R)-2-N-(tetradecylamino)-1-(4'-nitrophenyl)-1,3-propandiol (LCL204) are shown for comparison. Actin staining results are also shown (bottom micrograph). The control lane represents the effects of adding vehicle only.
Figure 14B:
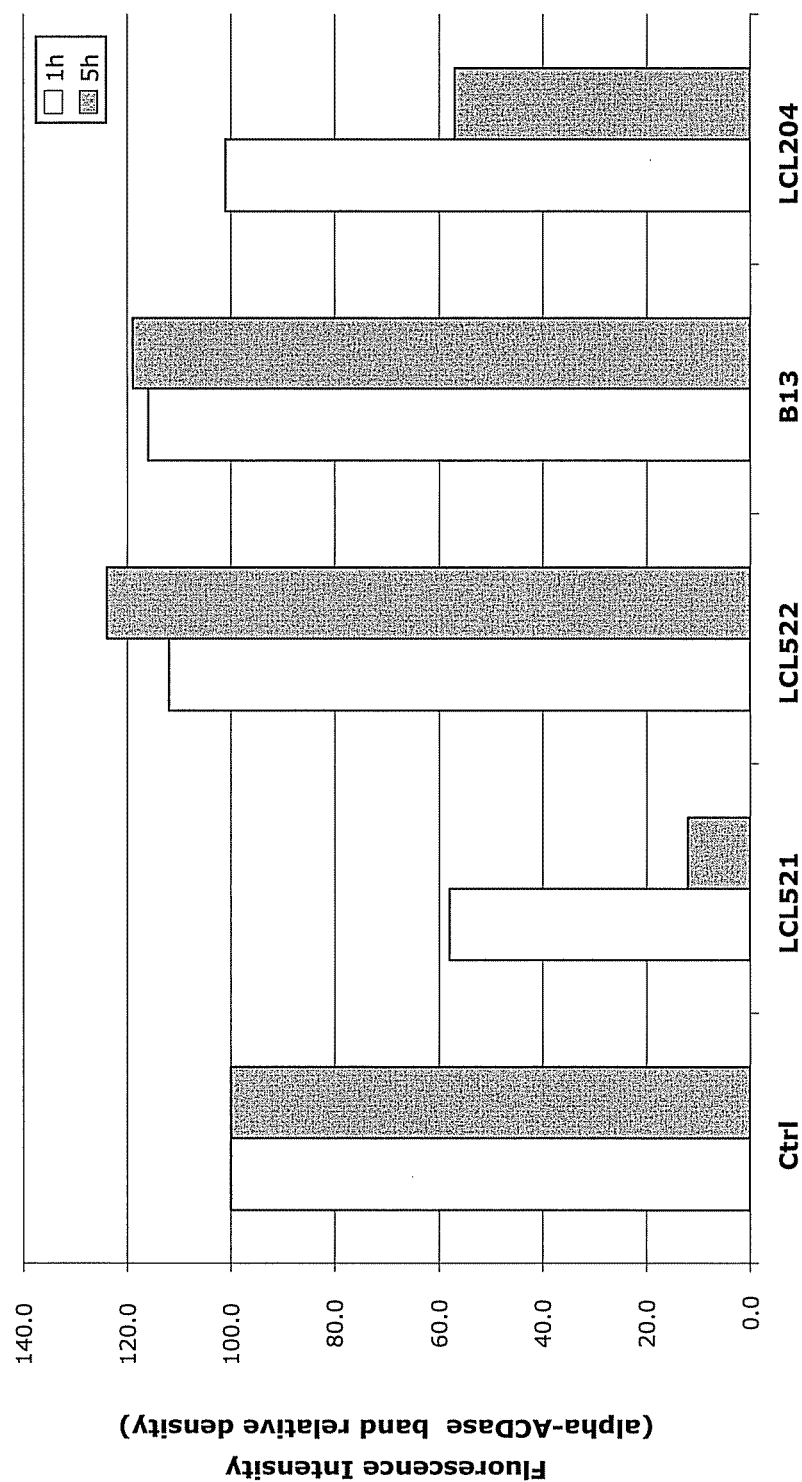
FIG. 14B is a bar graph showing the quantified results of the Western blots described for FIG. 14A. Results are expressed as fluorescence intensity relative to the control. Data for the 1 hour treatments are shown in the open bars and data for the 5 hour treatments are shown in the shaded bars.
Figure 15:
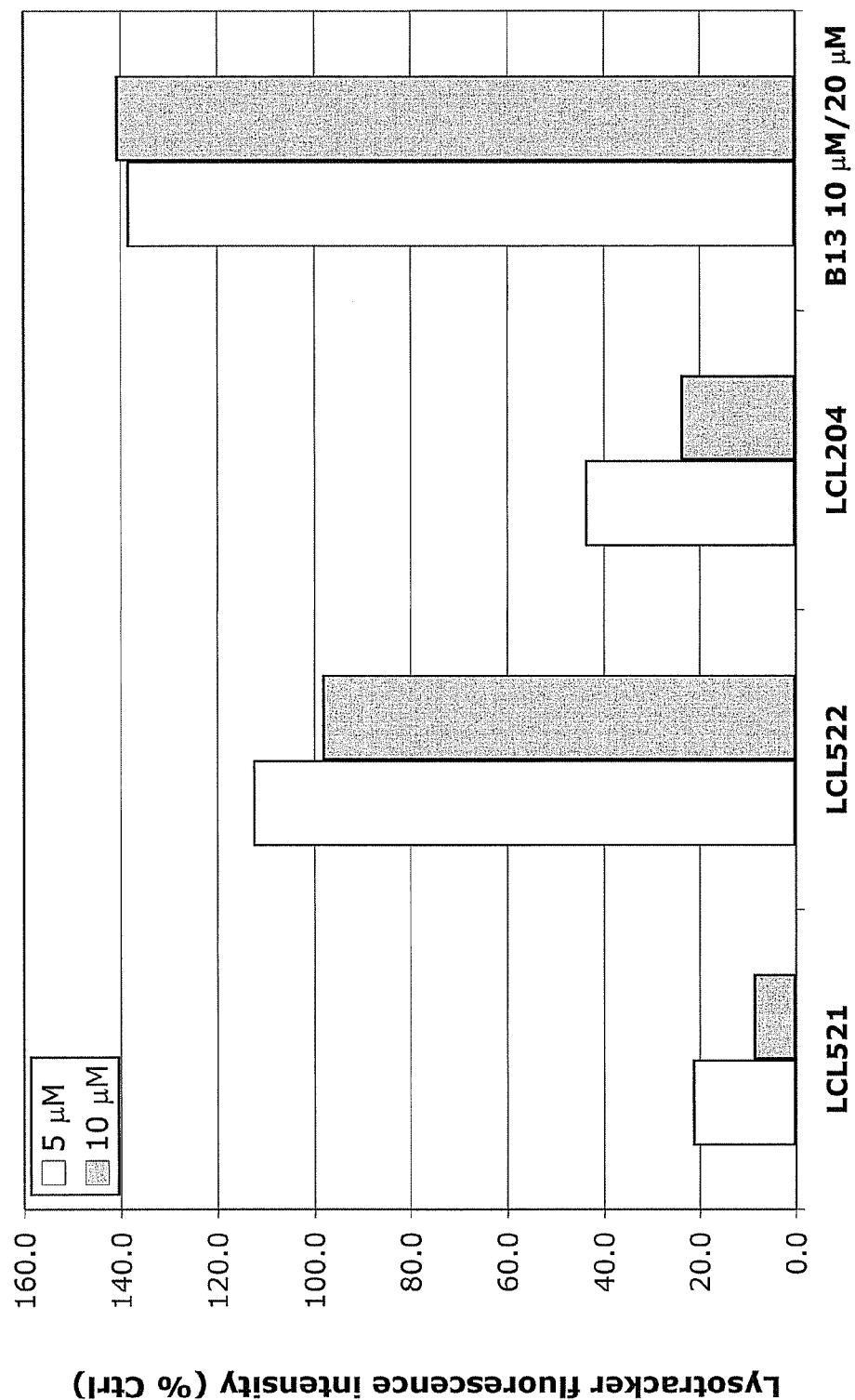
FIG. 15 is a bar graph showing the effect of 5 μM (open bars) or 10 μM (shaded bars) Class E prodrug (LCL521 or LCL522) on lysosomes after 1 hour. Lysosomal stability was measured using LYSOTRACKER™ Red dye (Molecular Probes, Eugene, Oreg. United States of America) fluorescence. Results for (1R,2R)-2-N-(tetradecanoylamino)-1-(4'-nitrophenyl)-1,3-propandiol (B13) and (1R,2R)-2-N-(tetradecylamino)-1-(4'-nitrophenyl)-1,3-propandiol (LCL204) are shown for comparison. For B13 the open bar represents the results of treatment with 10 μM compound and the shaded bar represents treatment with 20 μM compound.
Figure 16:
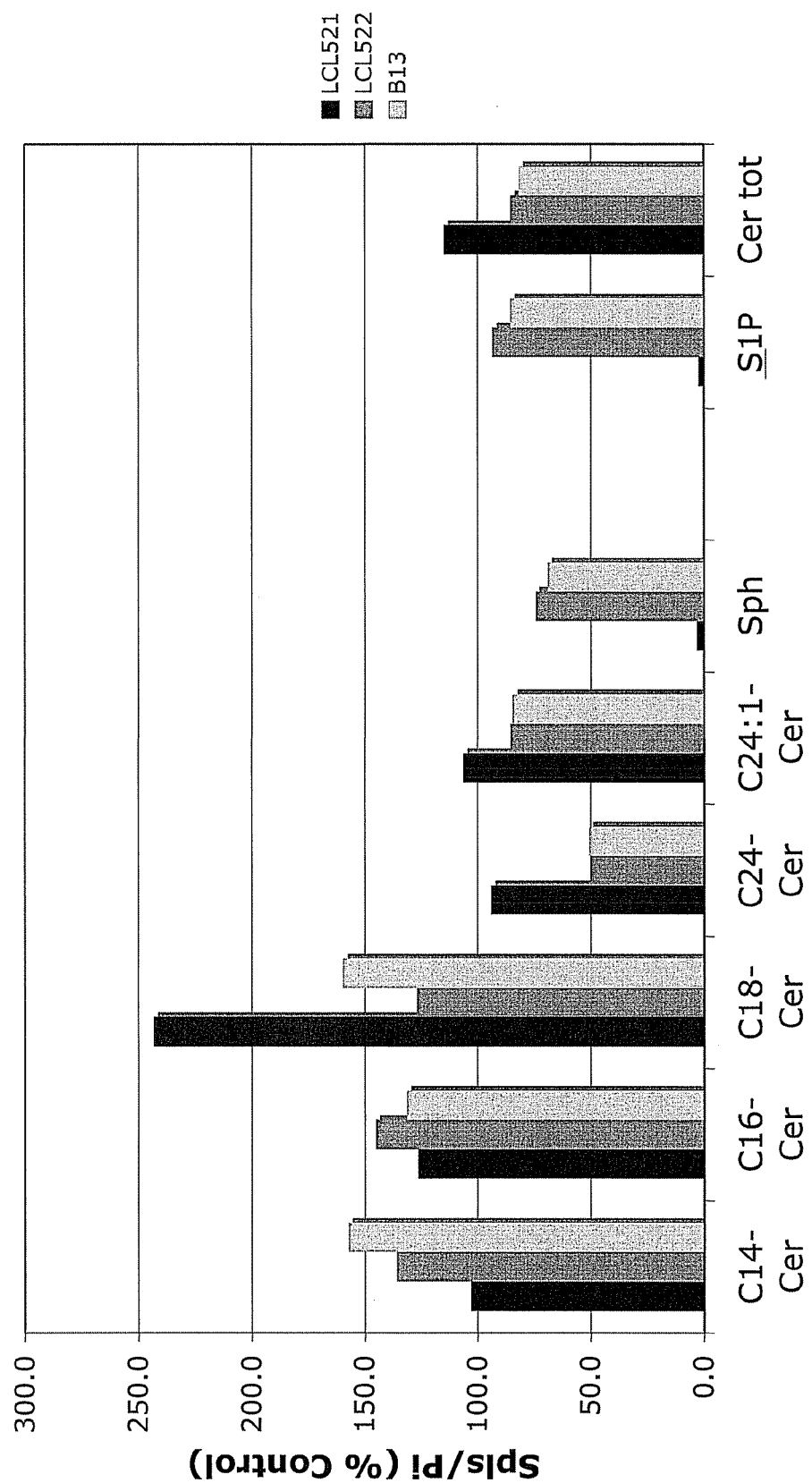
FIG. 16 is a bar graph showing the effect of 10 μM LCL521 (darkly shaded bars), LCL522 (medium shaded bars) or (1R,2R)-2-N-(tetradecanoylamino)-1-(4'-nitrophenyl)-1,3-propandiol (B13; lightly shaded bars) on the levels of cellular sphingolipids (C14-, C16-, C18-, C24-, C24:1-ceramides ($C_n$-Cer), sphingosine (Sph), sphingosine-1-phosphate (S1P) and total ceramides (Cer tot) in MCF-7 cells after 5 hours FIG. 17 is a graph showing the early inhibitory effect of LCL521 on cellular sphingosine (Sph; darkly shaded circles) and shingosine-1-phosphate (S1P, open circles). The time dependent levels of ceramides (C14-Cer, darkly shaded diamonds; C16-Cer, darkly shaded squares; C18-Cer, darkly shaded triangles; C24-Cer, lightly shaded squares; C24:1-Cer, "*"s; and total ceramines (Cer tot), open squares) are also shown. Treatment with LCL521 provides a time dependent increase in pro-apoptotic C18- and C16-Cers.
Figure 17:
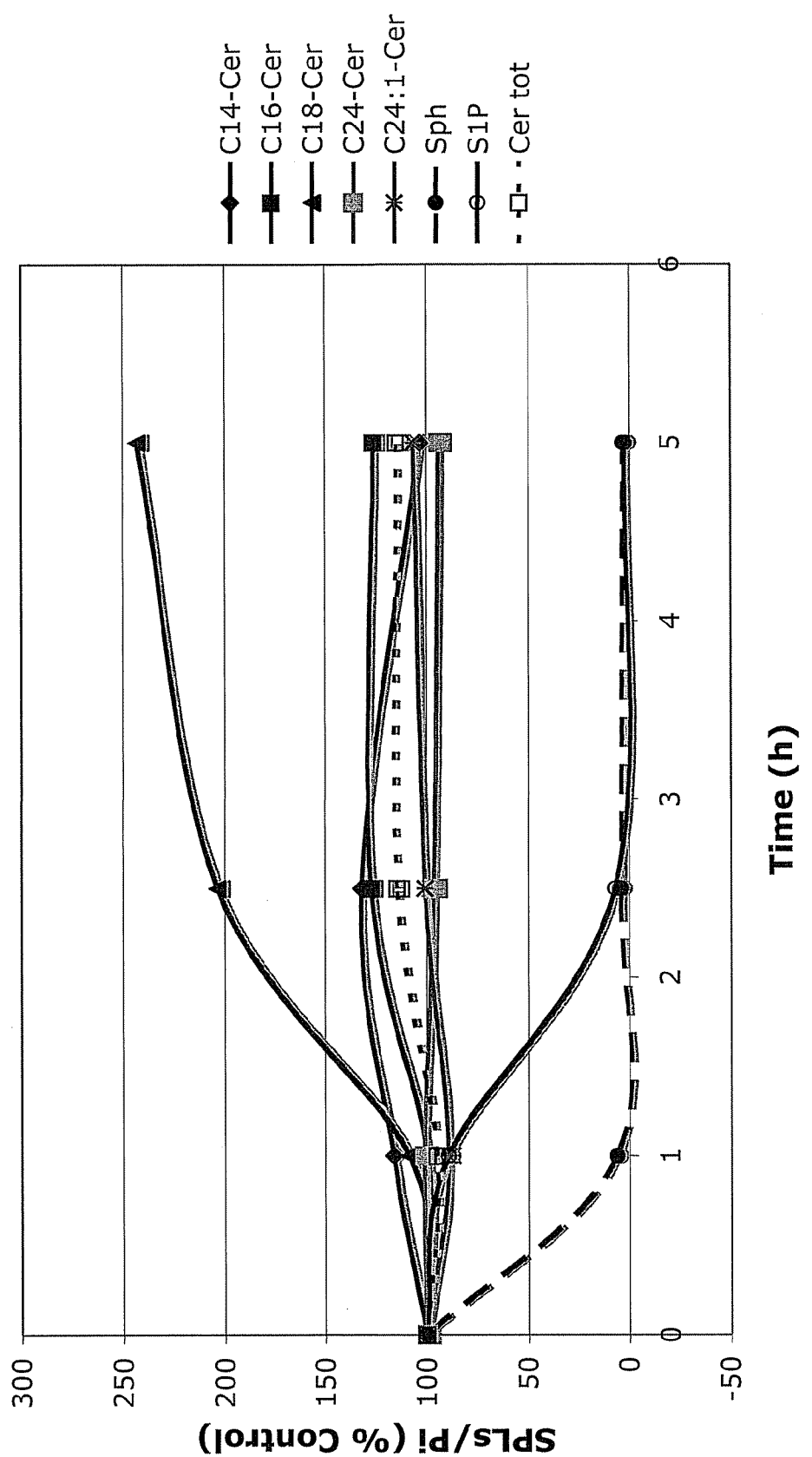

In addition, results with the prodrugs, such as LCL521, i.e., 1,3-O-bis-dimethylglycine-B13 hydrochloride, and LCL522 i.e., 1-O-dimethylglycine-B13 hydrochloride (see FIG. 2), show increased inhibitory effect on MCF-7 cells. The $IC_{50/24h}$ values (i.e., the 50% inhibitory concentrations after 24 hours) of LCL521 and LCL522 were about 8.9 µM and 6.5 µM, respectively, as compared to 60.0 µM for B13. See Example 7, below. See also, FIG. 12. LCL521 inhibits ACDase in vitro (see FIG. 13) and in cells causing a decrease of the alpha-subunit of the active form of the enzyme. See FIGS. 14A and 14B. LCL521 can also be delivered to the lysosomes. See FIG. 15. LCL521 is effective in decreasing the cellular level of Sph and S1P and increases cellular pro-apoptotic C16- and C18-ceramides. See FIGS. 16 and 17. LCL522 is not as effective as LCL521 in regulating cellular sphingolipids, behaving more like B13. See FIG. 16. Without being bound to any one theory, preliminary results suggest that LCL522 hydrolyzes relatively quickly to form B13, whereas LCL521 is slowly metabolized to LCL581, a mono-ester analog of B13, and to B13. These results suggest that the presently disclosed prodrug approach can increase the therapeutic index of ACDase inhibitors *in vivo*.

II. Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Throughout the specification and claims, a given chemical formula or name shall encompass all optical and stereoisomers, as well as racemic mixtures where such isomers and mixtures exist, unless otherwise specified.

Following long-standing patent law convention, the terms "a", "an", and "the" refer to "one or more" when used in this application, including the claims. Thus, the phrase "a compound" refers to one or more compounds.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

The term "ceramide" can refer to an amide-containing compound formed from sphingosine having a fatty acid attached at the sphingosine amino group. In some embodiments, the ceramide is a naturally-occurring molecule. Ceramides can be referred to as a "$C_n$-Cer", where n is the number of carbon atoms in the acyl group formed from the fatty acid. In some cases the ceramide can include one or more double bonds in the fatty acid acyl group (e.g., C24:1-Cer, which is the ceramide with a 24 carbon fatty acid chain and one double bond).

The term "ceramidase-related" can refer to reverse ceramidase activity and to the activities of ceramide/dhceramide synthases and acyl-transferases.

The term "about", as used herein when referring to a measurable value such as an amount of weight, time, dose, etc., is meant to encompass variations of in some embodiments ±20% or ±10%, in some embodiments ±5%, in some embodiments ±1%, and in some embodiments ±0.1% from the specified amount, as such variations are appropriate to perform the disclosed methods.

The term "free of" when referring to a condition means that the condition being referred to is absent or not occurring, or is substantially absent or substantially not occurring. Thus, "free of" can refer to embodiments, wherein a particular condition is absent or not occurring, as well as to embodiments wherein a particular condition is substantially absent or not occurring (e.g., occurs in less 20, 15, 10, 5, 4, 3, 2, or 1% of a particular population, such as a cell, organelle, or subject population).

The term "and/or" when used to describe two or more activities, conditions, or outcomes refers to situations wherein both of the listed conditions are included or wherein only one of the two listed conditions are included. Thus, when referring to a situation that is free of permanent lysosomal disruption and/or degradation of acid ceramidase, the situation can be free of permanent lysosomal disruption, free of the degradation of acid ceramidase, or free of both permanent lysosomal disruption and degradation of acid ceramidase.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentynyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

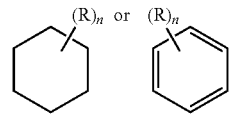

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

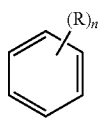

wherein n is an integer from 0 to 2 comprises compound groups including, but not limited to:

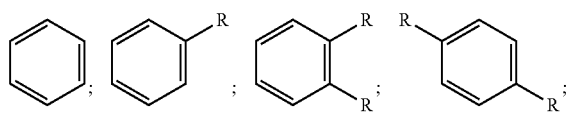

and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "heterocycle" refers to a non-aromatic or aromatic, monocyclic or multicyclic ring system of about 3 to about 14 atoms, wherein at least one of the atoms is a heteroatom (e.g., oxygen, nitrogen, or sulfur). The term "N-heterocycle" refers to a heterocycle wherein at least one of the heteroatoms is a nitrogen atom. Examples of N-heterocycles include, but are not limited to, azetidine, pyrrolidine, pyrrole, pyrroline, pyrazole, pyrazoline, pyrazolidine, piperidine, pyridine, piperazine, pyrazine, pyrimidine, pyridazine, morpholine, imidazole, benzimidazole, imidazoline, imidazolidine, indole, carbazole, quinoline, isoquinoline, oxazole, thiazole, isothiazole, and thiazine. In some embodiments, the term N-heterocycle refers to N-heterocycles other than pyridine.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

As used herein, the term "acyl" refers to an organic carboxylic acid group wherein the —OH of the carboxyl group has been replaced with another substituent. Thus, an "acyl" group can be represented by the structure RC(=O)— group, wherein R is an alkyl, substituted alkyl, aralkyl, aryl or substituted aryl group as defined herein. As such, the term "acyl" specifically includes arylacyl groups, such as an acetylfuran and a phenacyl group. Specific examples of acyl groups include acetyl and benzoyl.

"N-acyl" refers to a group having the structure —N—C(=O)—R, wherein R is as defined for acyl. These groups can also be referred to as amides. Modified N-acyl groups include compounds wherein the oxygen of the N-acyl has been replaced by S or NH, as well as to compounds wherein the carbonyl group (i.e., the —C(=O)—) is attached to a second heteroatom in addition to the nitrogen. For example, the carbonyl can be attached to a second nitrogen atom to form a urea linkage (i.e., —NH—C(=O)—NH—R).

The term "amino" refers to the —NH$_2$, the NHR, and the NR$_2$ groups, wherein R is alkyl, substituted alkyl, aryl, substituted aryl, or aralkyl, as well as to amino functionalities in N-heterocycles (e.g., morpholine, etc).

The term "ester" refers to a moiety comprising an —O—C(=O)—R group, wherein R can be alkyl, substituted alkyl, aralkyl, aryl, or substituted aryl. In some embodiments, the R group can include an amino substituent and the ester is an amino ester.

The terms "halo", "halide", or "halogen" as used herein refer to fluoro, chloro, bromo, and iodo groups.

The term "hydroxyl" refers to the —OH group.

The term "nitro" refers to the —NO$_2$ group.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

The term "cancer metastasis" refers to the spread of a primary tumor into another organ.

The term "apoptosis" refers to programmed cell death, which can be a genetically controlled response for cells to commit suicide. The symptoms of apoptosis are viability loss accompanied by cytotoxic boiling, chromatin condensation, and DNA fragmentation. See, e.g., Wyllie et al., *Int. Rev. Cytol.*, 68, 251-306 (1980). The apoptotic process has important roles in regulating the development of tissues, the sizes and shapes of organs, and the life span of cells.

III. Compounds of Formula (I)

III.A. ω-Aminoacyl Analogs of B13

In some embodiments, the presently disclosed subject matter provides a compound of Formula (Ia):

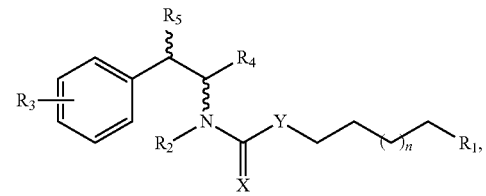

wherein:

n is an integer from 0 to 13;

$R_1$ is selected from the group comprising NH$_2$, NHR$_6$, NR$_6$R$_7$, and N-heterocycle;

$R_2$ is selected from the group comprising H and alkyl;

$R_3$ is selected from the group comprising H, OH, NO$_2$, NH$_2$ and NHR$_9$;

$R_4$ is selected from the group comprising H, CH$_3$, CH$_2$OH, and CH$_2$O—C(=O)—CH(R$_8$)NR$_6$R$_7$;

$R_5$ is selected from the group comprising H, OH, =O, and OC(=O)CH(R$_8$)NR$_6$R$_7$ each $R_6$, $R_7$, and $R_8$ is independently selected from the group comprising H, alkyl, aralkyl, and aryl;

$R_9$ is C(=O)—(CH$_2$)$_m$R$_{10}$, wherein m is an integer from 5 to 10;

$R_{10}$ is H, alkyl, cycloalkyl, or heterocycle;

X is selected from the group comprising O, NH, and S; and

Y is CH$_2$ or NH.

In some embodiments, the compound of Formula (Ia) is an amide or urea. Thus, in some embodiments, X is O. In some embodiments, the compound is an amide and X is O and Y is CH$_2$.

In some embodiments, $R_2$ is H or lower alkyl (i.e., C1-C6 alkyl), such as methyl, ethyl, n-propyl, isopropyl, n-butyl, sec-butyl, n-pentyl, or n-hexyl. In some embodiments, $R_2$ is H In some embodiments, the phenyl ring of Formula (Ia) is substituted by one or more nitro groups. Thus, in some embodiments, $R_3$ is $NO_2$. In some embodiments, $R_3$ is substituted meta or para to the substituted alkyl group comprising the nitrogen-containing group. In some embodiments, $R_3$ is para.

In some embodiments, one or both of $R_4$ and $R_5$ comprise and oxygen-containing substituent. In some embodiments, one or both of $R_4$ and $R_5$ are hydroxyl groups or comprise an ester. In some embodiments, $R_4$ is $CH_2OH$. In some embodiments, $R_5$ is OH.

The variable n can be 0, 1, 2, 3, 4, 5, 6, 7, 8, 9, 10, 11, 12, or 13. In some embodiments, n is an integer between 1 and 7. In some embodiments, n is 7. In some embodiments, n is 1.

The $R_1$ group can be any suitable amino group. The amino group can be unsubstituted (i.e., $NH_2$) or include one or more alkyl, aralkyl or aryl nitrogen substituents. In some embodiments, $R_1$ is an alkylamino group and has the structure $NHR_6$ wherein $R_6$ is alkyl. In some embodiments, $R_1$ is a dialkyl amino group and has the structure, $NR_6R_7$ wherein $R_6$ and $R_7$ are each alkyl. In some embodiments, $R_1$ is N-heterocycle. Suitable N-heterocycles include both aromatic and non-aromatic N-heterocycles. The N-heterocycles can include heteroatoms in addition to the nitrogen atom (e.g., O or S). N-heterocycles can also include more than one nitrogen atom. Suitable N-heterocycles include, but are not limited to, azetidine, pyrrolidine, pyrrole, pyrroline, pyrazole, pyrazoline, pyrazolidine, piperidine, pyridine, piperazine, pyrazine, pyrimidine, pyridazine, morpholine, imidazole, benzimidazole, imidazoline, imidazolidine, indole, carbazole, quinoline, isoquinoline, oxazole, thiazole, isothiazole, and thiazine. In some embodiments, the N-heterocycle is not pyridine. In some embodiments $R_1$ is imidazole or morpholine, e.g.,

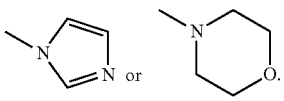

The stereochemistry of the carbon attached to the $R_5$ group and carbon attached to the N atom and the $R_4$ group can be independently R or S. In some embodiments, the stereochemistry at both of the carbons is R.

In some embodiments, the compound is one of the group including, but not limited to, (1R,2R)-2-[N-(12'-{1"-imidazol}-dodecanoyl)-amino]-1-(4"-nitrophenyl)-1,3-propandiol (LCL433); (1R,2R)-2-[N-(12'-{1"-morpholine}-dodecanoyl)-amino]-1-(4"-nitrophenyl)-1,3-propandiol (LCL449); (1R,2R)-2-[N-(12'-amino-dodecanoyl)-amino]-1-(4"-nitrophenyl)-1,3-propandiol (LCL463); (1R,2R)-2-[N-(12'-N,N-dimethylamino-dodecanoyl)-amino]-1-(4"-nitrophenyl)-1,3-propandiol (LCL464); (1R,2R)-2-[N-(6'-{N-octylamino}-hexanoyl)-amino]-1-(4"-nitrophenyl)-1,3-propandiol (LCL488); and (1R,2R)-2-[N-{12'-N-methylamino}-dodecanoyl)-amino]-1-(4"-nitrophenyl)-1,3-propandiol (LCL506). In some embodiments, the compound is (1R,2R)-2-[N-(12'-N,N-dimethylamino-dodecanoyl)-amino]-1-(4"-nitrophenyl)-1,3-propandiol (LCL464).

The ω-aminoacyl analogs of B13 can be synthesized by any suitable method, such as that described hereinbelow in Example 2 and as illustrated in FIG. 1. For example, a suitable 2-aminoethyl-substituted aromatic compound, such as 2-amino-1-(4-nitrophenyl)propane-1,3 diol (i.e., compound 1 in FIG. 1), can be reacted with an ω-halo-acyl halide (e.g., a ω-bromo-acyl chloride) to form an amide. Nucleophilic substitution of the halide at the end of the acy chain with an amine (i.e., ammonia, alkylamine, dialkylamine, or an N-heterocycle) results in the desired compound of Formula (Ia). The nucleophilic substitution reaction can be performed in a suitable organic solvent (e.g., an alcohol, such as methanol, ethanol, or propanol, or an ether, such as tetrahydrofuran (THF), in the presence of a base (e.g., NaOH, $NaHCO_3$, etc.) to neutralize any acid (e.g., HBr) formed during the reaction. Other suitable leaving groups can be used in place of the halide, including mesylates (i.e., $—O_3SCH$) and toxylates (i.e., $—O_3SC_6H_4CH_3$). Ureas of Formula (Ia) can be prepared by first transforming the amine starting material (e.g., compound 1) or a protected version thereof into an isocyanate (e.g., by reaction with phosgene) and then reacting the isocyanate with a suitable amine. As will be understood to those of skill in the art, the suitable amine can be a primary amine that includes an alkyl group with a second substitutent (i.e., in addition to the primary amino group) that is protected and/or can be transformed via further chemical transformations into a halogen or an amine group.

III.B. Prodrugs of B13

In representative embodiments, compounds disclosed herein are prodrugs, such as prodrugs of B13 or analogs thereof. A prodrug means a compound that, upon administration to a subject or sample, is capable of providing (directly or indirectly) another compound (i.e., a "parent compound") having a desired activity (e.g., inhibition of ACDase). In some, but not all, embodiments, the prodrug compound has less inhibitory activity than the parent compound. In some embodiments, the prodrug compound has no measurable inhibitory activity prior to transformation to the parent compound. In some embodiments, the prodrug itself has a desired activity.

Transformation of the prodrug to the parent compound can take place in the presence of particular enzymes (e.g., esterases) or at certain biological conditions (e.g., at a physiologially relevant pH). In some embodiments, the prodrug is intially transformed into another prodrug, which is then transformed (sometimes much more slowly) into the parent compound. Prodrugs can increase the bioavailability of the compounds of the presently disclosed subject matter when such compounds are administered to a subject (e.g., by allowing an orally administered compound to be more readily absorbed into the blood) and/or can enhance delivery of the parent compound to a biological compartment (e.g., a lysosome, the brain or lymphatic system, etc.) relative to a metabolite species, for example.

Accordingly, in some embodiments, the presently disclosed subject matter provides a compound of Formula (Ib):

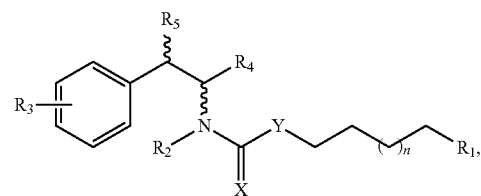

wherein:

n is an integer from 0 to 13;

$R_1$ is selected from the group comprising H, OH, SH, $NH_2$, Cl, Br, I, C(=O)OH, C(=O)$NH_2$, NH(C=NH)$NH_2$, $NHR_6$, $NR_6R_7$, $^+N(R_6)_3$ and N-heterocycle;

$R_2$ is selected from the group comprising H and alkyl;

$R_3$ is selected from the group comprising H, OH, $NO_2$, $NH_2$ and $NHR_9$;

$R_4$ is selected from the group comprising H, $CH_3$, $CH_2OH$, and $CH_2O-C(=O)-CH(R_8)NR_6R_7$;

$R_5$ is selected from the group comprising H, OH, =O, and $OC(=O)CH(R_8)NR_6R_7$ each $R_6$, $R_7$, and $R_8$ is independently selected from the group comprising H, alkyl, aralkyl, and aryl;

$R_9$ is $C(=O)-(CH_2)_mR_{10}$, wherein m is an integer from 5 to 10;

$R_{10}$ is H, alkyl, cycloalkyl, or heterocycle;

X is selected from the group comprising O, NH, and S;

Y is $CH_2$ or NH; and wherein at least one of $R_4$ and $R_5$ comprises an ester moiety.

In some embodiments, $R_4$ comprises an ester. For example, $R_4$ can have the formula: $-CH_2O-C(=O)-CH(R_8)NR_6R_7$. In some embodiments, $R_8$ is H and $R_6$ and $R_7$ are each alkyl.

In some embodiments, $R_5$ comprises an ester moiety. In some embodiments, $R_5$ is $-OC(=O)CH(R_8)NR_6R_7$. In some embodiments, $R_8$ is H, and $R_6$ and $R_7$ are each alkyl.

In some embodiments, both $R_5$ and $R_4$ comprise ester moieties. Thus, in some embodiments, $R_4$ is $CH_2O-C(=O)-CH(R_8)NR_6R_7$ and $R_5$ is $OC(=O)-CH(R_8)NR_6R_7$.

In some embodiments, n is 5 and $R_1$ is n-butyl.

In some embodiments, the compound of Formula (Ib) is an amide or urea. Thus, in some embodiments, X is O. In some embodiments, the compound is an amide and X is O and Y is $CH_2$.

In some embodiments, $R_2$ is H or lower alkyl (i.e., C1-C6 alkyl), such as methyl, ethyl, n-propyl, isopropyl, n-butyl, sec-butyl, n-pentyl, or n-hexyl. In some embodiments, $R_2$ is H In some embodiments, the phenyl ring of Formula (Ib) is substituted by one or more nitro groups. Thus, in some embodiments, $R_3$ is $NO_2$. In some embodiments, $R_3$ is substituted meta or para to the substituted alkyl group comprising the nitrogen-containing group. In some embodiments, $R_3$ is para.

The stereochemistry of the carbon attached to the $R_5$ group and carbon attached to the N atom and the $R_4$ group can be independently R or S. In some embodiments, the stereochemistry at both of the carbons is R.

In some embodiments, the compound of Formula (Ib) is selected from the group including, but not limited to:

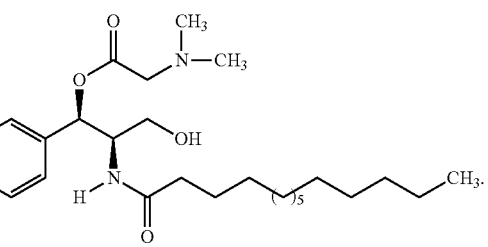

(LCL522)

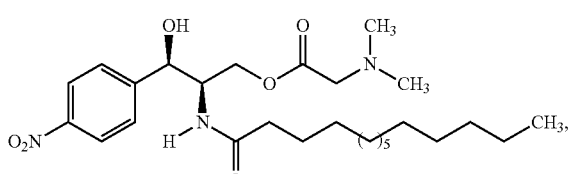

(LCL521)

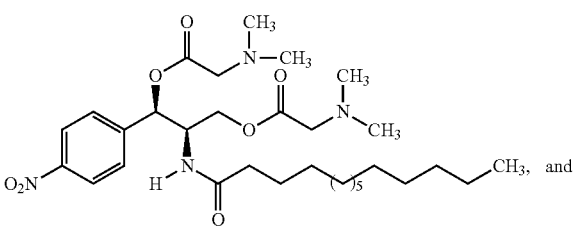

and

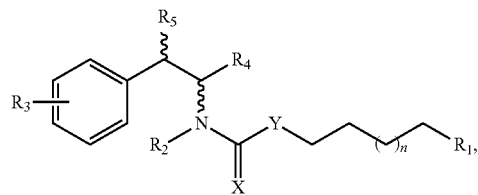

(LCL581)

The prodrugs can be prepared by the exhaustive or selective esterification of B13 or hydroxy-containing B13 analogs, for example, using reagents and or conditions known in peptide synthesis. In some embodiments, selective esterification involves the use of appropriate protecting group strategies to protect more reactive primary alcohols present when esterification of less reactive secondary alcohols is desired.

III.C. Pharmaceutically Acceptable Salts

In some embodiments, the presently disclosed compounds can be administered as pharmaceutically acceptable salts. Thus, in some embodiments, the presently disclosed subject matter provides pharmaceutically acceptable salts of the compounds of Formulas (Ia) and (Ib). Such pharmaceutically acceptable salts include the gluconate, lactate, acetate, tartarate, citrate, phosphate, maleate, borate, nitrate, sulfate, and hydrochloride salts. In some embodiments, the salt is a hydrochloride salt. The salts of the compounds described herein can be prepared, for example, by reacting a basic (e.g., amine-containing) compound with the desired acid in solution.

IV. Uses of Compounds of Formula (I)

In some embodiments, the presently disclosed subject matter provides a method of inhibiting ACDase or a ceramidase-related activity by contacting a sample with a compound of Formula (I):

wherein:

n is an integer from 0 to 13;

$R_1$ is selected from the group consisting of H, OH, SH, $NH_2$, Cl, Br, I, $C(=O)OH$, $C(=O)NH_2$, $NH(C=NH)NH_2$, $NHR_6$, $NR_6R_7$, $^+N(R_6)_3$ and N-heterocycle;

$R_2$ is selected from the group consisting of H and alkyl;

$R_3$ is selected from the group consisting of H, OH, $NO_2$, $NH_2$ and $NHR_9$;

$R_4$ is selected from the group consisting of H, $CH_3$, $CH_2OH$, and $CH_2O-C(=O)-CH(R_8)NR_6R_7$;

$R_5$ is selected from the group consisting of H, OH, =O, and $OC(=O)CH(R_8)NR_6R_7$ each $R_6$, $R_7$, and $R_8$ is independently selected from the group consisting of H, alkyl, aralkyl, and aryl;

$R_9$ is $C(=O)-(CH_2)_mR_{10}$, wherein m is an integer from 5 to 10;

$R_{10}$ is H, alkyl, cycloalkyl, or heterocycle;

X is selected from the group consisting of O, NH, and S;

Y is $CH_2$ or NH; and wherein at least one of $R_4$ and $R_5$ comprises an ester moiety or wherein $R_1$ is selected from the group consisting of $NH_2$, $NHR_6$, $NR_6R_7$, and N-heterocycle. Thus, the compounds of Formula (I) include the compounds of Formulas (Ia) and (Ib) as described hereinabove in Section III. In some embodiments, the inhibitory action of the compound of Formula (I) can be accomplished without or substantially without (i.e., with less than 20, 15, 10, 5, 4, 3, 2, or 1%) permanent lysosomal destabilization and/or proteolytic degradation of the acid ceramidase.

In some embodiments, the sample is an in vitro cell sample or an in vivo cell sample. Thus, the sample can include whole cells in culture media or lysed cells containing ACDase. The sample can also include cells present in a tissue, plasma, or organ sample or present in a subject. Thus, the presently disclosed methods can be used in scientific and/or medical research related to ACDase and ceramidase-related activity.

The presently disclosed subject matter also provides methods involving the use of the compounds of the presently disclosed subject matter for treatment, prophylaxis, management, or amelioration of one or more symptoms associated with various diseases and disorders. Accordingly, in some embodiments, the presently disclosed subject matter provides a method of treating or preventing a disease or disorder associated with undesirable ceramidase, ceramidase-related and/or sphinogsine kinase activity in a subject, wherein the method comprises administering to the subject an effective amount of a compound of Formula (I):

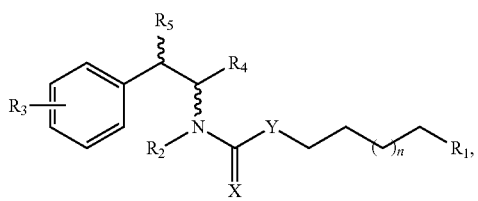

wherein:
n is an integer from 0 to 13;
$R_1$ is selected from the group comprising H, OH, SH, $NH_2$, Cl, Br, I, C(=O)OH, C(=O)$NH_2$, NH(C=NH)$NH_2$, $NHR_6$, $NR_6R_7$, $^+N(R_6)_3$ and N-heterocycle;
$R_2$ is selected from the group comprising H and alkyl;
$R_3$ is selected from the group comprising H, OH, $NO_2$, $NH_2$ and $NHR_9$;
$R_4$ is selected from the group comprising H, $CH_3$, $CH_2OH$, and $CH_2O$—C(=O)—CH($R_8$)$NR_6R_7$;
$R_5$ is selected from the group comprising H, OH, =O, and OC(=O)CH($R_8$)$NR_6R_7$
each $R_6$, $R_7$, and $R_8$ is independently selected from the group comprising H, alkyl, aralkyl, and aryl;
$R_9$ is C(=O)—$(CH_2)_mR_{10}$, wherein m is an integer from 5 to 10;
$R_{10}$ is H, alkyl, cycloalkyl, or heterocycle;
X is selected from the group comprising O, NH, and S;
Y is $CH_2$ or NH; and
wherein at least one of $R_4$ and $R_5$ comprises an ester moiety or wherein $R_1$ is selected from the group consisting of $NH_2$, $NHR_6$, $NR_6R_7$, and N-heterocycle. In some embodiments, administration of the compound of Formula (I) can be accomplished without or substantially without (i.e., with less than 20, 15, 10, 5, 4, 3, 2, or 1%) permanent lysosomal destabilization and/or proteolytic degradation of acid ceramidase.

As noted above, ceramide modulates a number of biochemical and cellular responses to stress, including apoptosis, cell-cycle arrest and cell senescence. For review, see Hannun et al., *Trends in Cell Biol.*, 10, 73-80 (2000); and Mathias et al., *Biochem. J.*, 335, 465-480 (1998). Several extracellular agents and stress stimuli, such as tumor necrosis factor α (TNF-α), chemotherapeutic agents, and heat are known to cause ceramide accumulation. One approach to cause accumulation of ceramide is accomplished by regulating the activities of enzymes such as ceramidase which is involved in the metabolism of ceramide. The changes in the ceramide concentration are sufficient to reproduce many of the biological effects of cytokines and stress inducers that are coupled to ceramide accumulation. The accumulation of ceramides also reproduces many of the features of cell senescence. In many cell types, ceramides cause cell differentiation, both morphologically and through the activation of biochemical programs of cell differentiation. Ceramide also induces apoptosis in most cancer cells, which can be accompanied by cell-cycle arrest. Thus, according to the presently disclosed subject matter, modulation of the levels of ceramide or sphingosine through the methods and compositions of the presently disclosed subject matter can bring about treatment and prevention of diseases that are related to stress response and apoptosis. Several exemplary diseases and disorders are disclosed below which can be treated or prevented by the methods of the presently disclosed subject matter.

Without being bound by any particular theory or theories, compounds of the presently disclosed subject matter can act as a modulator of one or more ceramidases (e.g., ACDase) or a ceramidase-related activity present in a cell or in an organelle of a cell. In some embodiments, the organelle is a positively charged organelle, such as but not limited to a lysosome. Regardless of the underlying mechanisms, the presently disclosed compounds can induce cell death.

In some embodiments, the presently disclosed subject matter provides a method of increasing the level of ceramide in a cell comprising contacting the cell with a compound that inhibits the ceramidase activity.

In some embodiments, the presently disclosed subject matter provides a method of inhibiting the formation of sphingosine in a cell comprising contacting the cell with a compound that inhibits the ceramidase activity such that the amount of sphingosine formed as a result of conversion from ceramide is reduced.

In some embodiments, the presently disclosed subject matter provides a method of increasing the intracellular levels of a ceramide in a subject comprising administering to the subject an effective amount of a compound that inhibits the ceramidase activity of the ceramidase protein in the subject's cells.

In some embodiments, the presently disclosed subject matter provides a method of inhibiting the intracellular formation of sphingosine in a subject comprising administering to said subject an effective amount of compound that inhibits the ceramidase activity of the ceramidase protein in the subject's cells.

In some embodiments, the composition that inhibits ceramidase function is administered to a subject therapeutically and/or prophylactically: (1) in diseases or disorders involving an increased (relative to normal or desired) level of ceramidase protein or function, for example, in subjects where ceramidase protein is biologically overactive or overexpressed; or (2) in diseases or disorders wherein in vitro (or in vivo) assays indicate the utility of ceramidase inhibitor administration. The increased level in ceramidase protein or function can be readily detected, e.g., by obtaining a tissue sample from a subject (e.g., from biopsy tissue) and assaying it in vitro for RNA or protein levels, structure and/or activity of the expressed ceramidase RNA or protein. Many methods standard in the art can be thus employed, including but not limited to ceramidase enzyme assays, immunoassays to detect and/or visualize ceramidase protein (e.g., Western blot, immunoprecipitation followed by sodium dodecyl sulfate polyacrylamide gel electrophoresis, immunocytochemistry, etc.) and/or hybridization assays to detect ceramidase expression by detecting and/or visualizing ceramidase mRNA (e.g., Northern assays, dot blots, in situ hybridization, etc.), etc.

According to the presently disclosed subject matter, disorders involving cell hyperproliferation and/or dysfunctional sphingolipid signal transduction are treated and/or prevented by administration of a composition that inhibits ceramidase function to a subject. These diseases and disorders include, but are not limited to, diseases and disorders related to cell proliferation, cell attachment, cell immigration, granulation tissue development, primary and metastatic neoplastic diseases, inflammation, cardiovascular disease, stroke, ischemia, and/or atherosclerosis. Diseases and disorders involving cell overproliferation that can be treated and/or prevented include, but are not limited to cancers, pre-malignant conditions (e.g., hyperplasia, metaplasia, dysplasia), benign tumors, hyperproliferative disorders, and benign dysproliferative disorders. Cancer is characterized primarily by an increase in the number of abnormal cells derived from a given normal tissue, invasion of adjacent tissues by these abnormal cells, and lymphatic or blood-borne dissemination of the abnormal cells to distant sites in the subject. Malignancies and related disorders, particularly metastatic cancer, which can be treated, prevented, managed, and/or ameliorated by administration of a composition of the presently disclosed subject matter that inhibits ceramidase function as discussed below (for a review of such disorders, see Fishman et al., *Medicine,* 2nd Ed., J.B. Lippincott Co., Philadelphia, 1985).

In some embodiments, disorders in which cell proliferation is deficient or is desired can be treated or prevented by administration of a composition of the presently disclosed subject matter that promotes ceramidase function to a subject.

The presently disclosed subject matter encompasses methods for treating and/or preventing diseases and disorders wherein the treatment or prevention would be improved by administration of the compounds of the presently disclosed subject matter.

In some embodiments, "treatment" or "treating" refers to an amelioration of disease or disorder, or at least one discernible symptom thereof. "Treatment" or "treating" also refers to an amelioration of at least one measurable physical parameter associated with a disease or disorder that is not necessarily discernible by the subject. "Treatment" or "treating" can also refer to inhibiting the progression of a disease or disorder either physically (e.g., stabilization of a discernible symptom), physiologically (e.g., stabilization of a physical parameter), or both. "Treatment" or "treating" also refers to delaying the onset of a disease or disorder.

In some embodiments, the methods and compositions of the presently disclosed subject matter are useful as a preventative measure against disease or disorder. As used herein, "prevention" or "preventing" refers to a reduction of the risk of acquiring a given disease or disorder.

In some embodiments, the compositions of the presently disclosed subject matter are used to treat cancer, cancer metastasis, atherosclerosis, stenosis, inflammation, asthma, and atopic dermatitis. In some embodiments, the presently disclosed subject matter provides a method of treating cancer comprising administering to a subject in need of treatment thereof an effective amount of a compound of Formula (I).

In some embodiments, the presently disclosed subject matter provides methods for treating or preventing diseases or disorders comprising administration of a compound of the presently disclosed subject matter in combination with other treatments.

Cancers and related disorders that can be treated and/or prevented by methods and compositions of the presently disclosed subject matter include, but are not limited to the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, non-secretory myeloma, osteosclerotic myeloma, plasma cell leukemia, solitary plasmacytoma and extramedullary plasmacytoma; Waldenstrom's acroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, non-glial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipidus; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; head and neck squamous cell cancers (HNSCCs), esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungaling (polypoid), ulcerating, superficial spreading, diffusely spreading, malignant lymphoma, liposarcoma, fibrosarcoma, and carcinosarcoma; colon cancers;

rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. For a review of such disorders, see Fishman et al., *Medicine*, 2$^{nd}$ Ed., J.B. Lippinocott Co., Philadelphia, 1985; and Murphy et al., *Informed Decisions: The Complete Book of Cancer Diagnosis, Treatment, and Recovery*, Viking Penguin, Penguin Books, U.S.A., Inc., New York, 1997).

In some embodiments, the methods and compositions of the presently disclosed subject matter are used for the treatment and/or prevention of breast cancer, prostate cancer, melanoma, alveolar cancer, or head and neck cancer.

The compositions of the presently disclosed subject matter that inhibit ceramidase activity can also be administered to treat pre-malignant conditions and/or to prevent progression of a pre-malignant condition to a neoplastic or malignant state. Such prophylactic or therapeutic use is indicated in conditions known or suspected of preceding progression to neoplasia or cancer, in particular, where non-neoplastic cell growth comprising hyperplasia, metaplasia, or most particularly, dysplasia has occurred. For review of such abnormal growth conditions, see Robbins and Angell, *Basic Pathology*, 2$^{nd}$ Ed., W.B. Saunders Co., Philadelphia, 1976, pages 68-79).

Alternatively or in addition to the presence of abnormal cell growth characterized as hyperplasia, metaplasia, or dysplasia, the presence of one or more characteristics of a transformed phenotype or of a malignant phenotype displayed in vivo or displayed in vitro by a cell sample from a subject can indicate the desirability of prophylactic and/or therapeutic administration of a composition that inhibits ceramidase function. Characteristics of a transformed phenotype can include morphology changes, looser substratum attachment, loss of contact inhibition, loss of anchorage dependence, protease release, increased sugar transport, decreased serum requirement, expression of fetal antigens, etc.

In some embodiments, leukoplakia, a benign-appearing hyperplastic or dysplastic lesion of the epithelium, or Bowen's disease, a carcinoma in situ, are pre-neoplastic lesions indicative of the desirability of prophylactic intervention.

In some embodiments, fibrocystic disease (cystic hyperplasia, mammary dysplasia, particularly adenosis (benign epithelial hyperplasia) is indicative of the desirability of prophylactic intervention. The gene of the human acid ceramidase of the presently disclosed subject matter is localized on chromosome 8 (8p22). Based on this location, acid ceramidase can be involved in diseases associated with this region, in addition to the disease and disorder discussed above, which include adenocarcinoma (thyroid), acute myeloid leukemia, and squamous cell cancer, especially that which is associated with the nasopharynx region.

In other embodiments, a subject which exhibits one or more of the following predisposing factors for malignancy is treated by administration of an effective amount of a compound of the presently disclosed subject matter: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, *Basic Pathology*, 2$^{nd}$ Ed., W.B. Saunders Co., Philadelphia, 1976, pages 112-113.

The presently disclosed subject matter also encompasses methods for treating and/or preventing a cancer or metastasis in a subject comprising in any order the steps of administering to the subject a compound of Formula (I). In some embodiments, the compositions and methods of the presently disclosed subject matter can be used to prevent, inhibit, and/or reduce the growth and/or metastasis of cancerous cells. The administration of compound inhibits or reduces the growth and/or metastasis of cancerous cells by in some embodiments at least 99%, in some embodiments at least 95%, in some embodiments at least 90%, in some embodiments at least 85%, in some embodiments at least 80%, in some embodiments at least 75%, in some embodiments at least 70%, in some embodiments at least 65%, in some embodiments at least 60%, in some embodiments at least 55%, in some embodiments at least 50%, in some embodiments at least 45%, in some embodiments at least 40%, in some embodiments at least 35%, in some embodiments at least 30%, in some embodiments at least 25%, in some embodiments at least 20%, in some embodiments at least 15%, in some embodiments at least 10%, and in some embodiments at least 5% relative to the growth or metastasis in absence of the administration of said compound.

The presently disclosed subject matter also encompasses methods of disease treatment and/or prevention that provide better therapeutic profiles than current single agent therapies or even current combination therapies. Encompassed by the presently disclosed subject matter are combination therapies that have additive potency or an additive therapeutic effect while reducing or avoiding unwanted or adverse effects.

Other cancer treatment that can be used in combination of the administration of the compounds of the presently disclosed subject matter include the use of one or more compositions which include, but are not limited to, chemoagents, immunotherapeutics, cancer vaccines, anti-angiogenic agents, cytokines, hormone therapies, gene therapies, biological therapies, and radiotherapies. While maintaining and/or enhancing efficacy of treatment, the methods of the presently disclosed subject matter can also increase subject compliance, improve therapy, and/or reduce unwanted or adverse effects.

In some embodiments, a compound of the presently disclosed subject matter is administered to a subject receiving a treatment modality for the treatment of cancer wherein the subject might experience unwanted or adverse effects to treatment with the treatment modality alone (e.g., the treatment modality might be toxic or harmful at its effective dose, administered alone). Given the presently disclosed subject matter, the compound can improve the therapeutic benefit of the treatment modality such that the dosage and/or frequency of administration of the treatment modality can be lowered when administered in conjunction with the compound. In some embodiments, a compound of the presently disclosed subject matter is administered to allow lower and/or less frequent doses of chemotherapy and/or radiation therapy.

In some embodiments, the methods of the presently disclosed subject matter encompass the administration of one or more angiogenesis inhibitors such as, but not limited to angiostatin (plasminogen fragment); anti-angiogenic antithrombin III; ANGIOZYME™; ABT-627; Bay 12-9566; Benefin; Bevacizumab; BMS-275291; cartilage-derived inhibitor (CDI); CAI; CD59 complement fragment; CEP-7055; Col 3; Combretastatin A-4; ENDOSTATIN™ (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kDa fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents (e.g., chemotherapeutic) that can be used in conjunction with the presently disclosed subject matter, including pharmaceutical compositions and dosage forms and kits of the presently disclosed subject matter, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin-2, or rIL-2), interferon alfa-2a; interferon α-2b; interferon α-n1; interferon α-n3; interferon β-I a; interferon γ-I b; iproplatin; irinotecan hydrochloride; lanreotide acetate; letrozole, leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinyispermine; bisnafide; bistratene A; bizelesin; brefiate; bropirimine; budotitane; buthionine sulfoximine; calcipotriol; calphostin C; camptothecin derivatives; canarypox IL-2; capecitabine; carboxamide amino triazole; carboxyamidotriazole; CaRest M3; CARN 700; cartilage derived inhibitor; carzelesin; casein kinase inhibitors (ICOS); castanospermine; cecropin B; cetrorelix; chlorins;

chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Representative additional anti-cancer drugs are 5-fluorouracil and leucovorin. These two agents are particularly useful when used in methods employing thalidomide and a topoisomerase inhibitor.

In some embodiments, the treatment of the presently disclosed subject matter further includes the administration of one or more immunotherapeutic agents, such as antibodies and immunomodulators, which include, but are not limited to, HERCEPTIN®, RITUXAN®, OVAREX™, PANOREX®, BEC2, IMC-C225, VITAXIN™, CAMPATH® I/H, Smart MI95, LYMPHOCIDE™, Smart I D10, and ONCOLYM™, rituximab, gemtuzumab, or trastuzumab.

In some embodiments, the treatment of the presently disclosed subject matter further includes administering one or more anti-angiogenic agents, which include, but are not limited to, angiostatin, thalidomide, kringle 5, endostatin, other Serpins, anti-thrombin, 29 kDa N-terminal and 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (see Maione et al., *Cancer Res.*, 51, 2077-2083, (1991)), a 14-amino acid peptide corresponding to a fragment of collagen I (see Tolsma et al., *J. Cell Biol.*, 122, 497-511 (1993)), a 19 amino acid peptide corresponding to a fragment of Thrombospondin I (see Tolsma et al., *J. Cell Biol.*, 122, 497-511 (1993)), a 20-amino acid peptide corresponding to a fragment of SPARC (see Sage et al., *J. Cell*

*Biochem.*, 57, 127-140 (1995)), or any fragments, family members, or derivatives thereof, including pharmaceutically acceptable salts thereof.

In some embodiments, the treatment method further comprises the use of radiation.

In some embodiments, the treatment method further comprises the administration of one or more cytokines, which include, but are not limited to, lymphokines, tumor necrosis factors, tumor necrosis factor-like cytokines, lymphotoxin-α, lymphotoxin-β, interferon-α, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40, or CD137 ligands, Fas/Fas ligand, 4-1BBL, endothelial monocyte activating protein or any fragments, family members, or derivatives thereof, including pharmaceutically acceptable salts thereof.

In some embodiments, the treatment method further comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antiestagens (e.g., mifepristone, onapristone), and anti-androgens (e.g., cyproterone acetate).

Other disorders of proliferation that can benefit from inhibition of ceramidase include cardiovascular diseases.

Vascular interventions, including angioplasty, stenting, atherectomy, and grafting for the treatment of cardiovascular diseases are often complicated by undesirable effects. One of the adverse reactions to vascular intervention include endothelial and smooth muscle cell proliferation which can lead to hyperplasia, or more specifically, restenosis which is the reclogging of the artery, occlusion of blood vessels, reperfusion injury, platelet aggregation, and calcification. In this model, an injurious stimulus induces expression of growth-stimulatory cytokines such as interleukin 1 and tumor necrosis factor. See Libby et al., *Circulation*, 86, III47-III52 (1992). There is evidence which shows that ceramide inhibit the growth of endothelia and smooth muscle cells of the coronary artery.

Various therapies have been attempted to treat or prevent stenosis or restenosis. However, there remains a great need for therapies directed to the prevention and treatment of cardiovascular diseases caused by hyperplasia of endothelia and smooth muscle cells. Since it has been shown that ceramide inhibit the growth of endothelia and smooth muscle cells of the coronary artery, it therefore can be desirable to raise the level of ceramide for the treatment and prevention of cardiovascular diseases. Recently, Kester and co-workers showed that ceramide used in angioplasty prevents restenosis. See Kester et al., *Circ. Res.*, 87, 282-288 (2000). Alternative, and more effectively, one aspect of the presently disclosed subject matter provides treatment and prevention of restenosis by adjusting the level of ceramide through administering a compound of the presently disclosed subject matter.

Accordingly, it therefore can be desirable to raise the level of ceramide for the treatment and prevention of cardiovascular diseases. This can be accomplished by adjusting the intracellular level of ceramide by using the compositions and methods of the presently disclosed subject matter. The outcome of a treatment is to at least produce in a treated subject a healthful benefit, which in the case of cardiovascular diseases, includes, but is not limited to a reduced risk of reclogging of arteries after a vascular intervention procedure and improved circulation.

In some embodiments, the presently disclosed subject matter provides a method for preventing, treating, managing, and/or ameliorating an autoimmune or inflammatory disorder or one or more symptoms thereof, said method comprising administering to a subject in need thereof a prophylactically and/or therapeutically effective amount of a compound of the presently disclosed subject matter and a prophylactically or therapeutically effective amount of one or more immunomodulatory agents.

Interleukin-1 is a major inducer of inflammation and TNF is an important regulator of the reaction. Both cytokines can activate ceramidase, and thus inhibiting the activity of ceramidase can result in an anti-inflammatory effect. This can involve the prevention of the formation of sphingosine and sphingosine phosphate which have pro-inflammatory effects. Also, inhibition of ceramidase can prevent the hyperproliferation of immune cells that are important for inflammation. There is evidence which suggests that an increase in ceramide and a decrease in sphingosine lead to a decrease in sphingosine phosphate. Preliminary data show that in mouse fibroblast cells, L929, TNF-α increases ceramide levels and leads to prostaglandin E2 (PGE2) release from these cells. The release of PGE2 is also shown to be inhibited by D-erythro-2-(N-myristolyamino)-1-phenyl-1-propanol), D-MAPP, which is an inhibitor of one of the ceramidase. This observation might be important for inhibiting inflammatory reactions that occur in conditions, such as but not limited to rheumatoid arthritis. Thus, it is possible to treat and/or prevent inflammation by regulating the level of cellular ceramide using the method of the presently disclosed subject matter. As discussed above, ceramide level can be increased by administering compounds of the presently disclosed subject matter that can inhibit mitochondrial ceramidase.

Examples of autoimmune disorders include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. Some autoimmune disorders are associated with an inflammatory condition. Thus, there is overlap between what is considered an autoimmune disorder and an inflammatory disorder. Therefore, some autoimmune disorders can also be characterized as inflammatory disorders.

The presently disclosed subject matter provides methods of preventing, treating, managing, and/or ameliorating an autoimmune or inflammatory disorder and/or one or more symptoms thereof, said methods comprising administering to a subject in need thereof a compound of the presently disclosed subject matter and one or more immunomodulatory agents. The immunomodulatory agents are administered to a subject with an autoimmune and/or inflammatory disorder whose mean absolute lymphocyte count is in some embodiments less than 500 cells/mm$^3$, in some embodiments less than 550 cells/mm$^3$, in some embodiments less than 600 cells/mm$^3$, in some embodiments less than 650 cells/mm$^3$, in some embodiments less than 700 cells/mm$^3$, in some embodiments less than 750 cells/mm$^3$, in some embodiments less than 800 cells/mm$^3$, in some embodiments less than 850 cells/mm$^3$ and in some embodiments less than 900 cells/mm$^3$. Thus, in some embodiments, prior to or subsequent to the administration of one or more dosages of one or more immunomodulatory agents to a subject with an autoimmune or inflammatory disorder, the absolute lymphocyte count of said subject is determined by techniques well-known to one of skill in the art, including, e.g., flow cytometry or trypan blue counts.

Examples of immunomodulatory agents include, but are not limited to, methotrexate, leflunomide, cyclophosphamide, cyclosporine A, and macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. Examples of T cell receptor modulators include, but are not limited to, anti-T cell receptor antibodies (e.g., anti-CD4 monoclonal antibodies, anti-CD3 monoclonal antibodies, anti-CD8 monoclonal antibodies, anti-CD40 ligand monoclonal antibodies, anti-CD2 monoclonal antibodies) and CTLA4-immunoglobulin. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF), anti-cytokine receptor antibodies (e.g., anti-IL-2 receptor antibodies, anti-IL-4 receptor antibodies, anti-IL-6 receptor antibodies, anti-IL-10 receptor antibodies, and anti-IL-12 receptor antibodies), anti-cytokine antibodies (e.g., anti-IFN receptor antibodies, anti-TNF-α antibodies, anti-IL-1β antibodies, anti-IL-6 antibodies, and anti-IL-12 antibodies).

Anti-inflammatory agents have exhibited success in treatment of inflammatory and autoimmune disorders and are now a common and a standard treatment for such disorders. Any anti-inflammatory agent well-known to one of skill in the art can be used in the compositions and methods of the presently disclosed subject matter. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

The presently disclosed subject matter also relates to the treatment of disorders involving deficient cell proliferation (growth) and/or in which cell proliferation is otherwise desired (e.g., degenerative disorders, growth deficiencies, lesions, physical trauma) by administering compounds that agonize, (promote) ceramidase function (e.g., ceramide-1-phosphate and sphingosine-1-phosphate). Other disorders that can benefit from activation of ceramidase are neurodegenerative disorders (e.g., Alzheimer's disease), and disorders of aging such as immune dysfunction.

As discussed above, like treatment of neoplastic conditions, successful treatment of cardiovascular diseases, inflammation, or the above-mentioned diseases can be brought about by techniques which serve to decrease ceramidase activity.

General techniques that can be employed for the determination of effective doses and administration of such compounds are known to the skilled artisan. Any technique which serves to selectively administer chemicals to a cell population of interest can be used, for example, by using a delivery complex. Such a delivery complex can comprise an appropriate chemical and a targeting agent. Such targeting agents can comprise, for example, sterols, lipids, viruses or target cell specific binding agents.

V. Pharmaceutical Preparation and Methods of Administration

The compounds described herein can be administered to a subject at therapeutically effective doses to treat or prevent diseases and disorder discussed above. A therapeutically effective dose refers to that amount of a compound sufficient to result in a healthful benefit in the treated subject. See the *Physicians' Desk Reference*® (53$^{rd}$ ed., 1999).

The term "subject" as used herein refers to a member of any invertebrate or vertebrate species. The methods of the presently disclosed subject matter are particularly useful for warm-blooded vertebrates. Thus, the presently disclosed subject matter concerns mammals and birds. More particularly provided is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the use of the disclosed methods and compositions on birds, including those kinds of birds that are endangered, kept in zoos or as pets, as well as fowl, and more particularly domesticated fowl, e.g., poultry, such as turkeys, chickens, ducks, geese, guinea fowl, and the like, as they are also of economic importance to humans.

Thus, the subject to which a compound of the presently disclosed subject matter is administered is in some embodiments an animal, including but not limited to mammal such as non-primate (e.g., cows, pigs, horses, chickens, cats, dogs, rats, etc.), or a primate (e.g., a monkey such as acynomolgous monkey or a human). In some embodiments, the subject is a human. The composition of the presently disclosed subject matter can be utilized for the prevention of a variety of cancers, e.g., in individuals who are predisposed as a result of familial history or in individuals with an enhanced risk to cancer due to environmental factors.

The methods and compositions of the presently disclosed subject matter can be used in subjects who are treatment naïve and/or in subjects who have previously received and/or are currently receiving treatment with other pharmaceutical agents or combinations, including but not limited to anti-cancer agents. Other subjects can include subjects that have metastasis or no metastasis.

The methods and compositions of the presently disclosed subject matter are useful not only in untreated subjects but are also useful in the treatment of subjects partially or completely un-responsive to other treatments. In some embodiments, the presently disclosed subject matter provides methods and compositions useful for the treatment of diseases or disorders in subjects that have been shown to be or might be refractory or non-responsive to therapies comprising the administration of other agents.

An absence or decreased level in ceramide level or function can be readily detected, e.g., by obtaining a subject tissue sample (e.g., from biopsy tissue) and assaying it in vitro for ceramide.

V.A. Effective Dose

Toxicity and therapeutic efficacy of compositions can be determined by standard pharmaceutical procedures in cell cultures or experimental animals (e.g., for determining the $LD_{50}$ (the dose lethal to 50% of the population) and the $ED_{50}$ (the dose therapeutically effective in 50% of the population)). The dose ratio between toxic and therapeutic effects is the therapeutic index and it can be expressed as the ratio $LD_{50}/ED_{50}$. In some embodiments, compounds that exhibit large therapeutic indices are employed. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies in some embodiments within a range of circulating concentrations that include the $ED_{50}$ with little or no toxicity. For example, the dosage can range from in some embodiments 10 nM to 100 µM and in some embodiments 1 to 10 µM or greater. The dosage can vary within this range depending upon the dosage form employed and the route of administration utilized. For any composition used in the methods of the presently disclosed subject matter, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Suitable daily doses for the treatment or prevention of a disorder described herein can be readily determined by those skilled in the art. A recommended dose of a composition of the presently disclosed subject matter is from about 0.1 mg to about 100 mg per day, given as a single once-a-day dose in the morning or as divided doses throughout the day. In some embodiments, a daily dose is from about 2 mg to about 25 mg per day and in some embodiments a daily dose is from about 5 mg to about 10 mg per day.

The anti-cancer activity of the methods and compositions used in accordance with the presently disclosed subject matter also can be determined by using various experimental animal models of such as cancer animal models such as scid mouse model or nude mice with human tumor grafts known in the art and described in Yamanaka et al. (*Microbiol. Immunol.*, 45, 507-514 (2001)).

In some embodiments, the methods and compositions of the presently disclosed subject matter are tested in vitro, and then in vivo, for the desired therapeutic or prophylactic activity, prior to use in a subject (e.g., a human). For example, in vitro assays which can be used to determine whether administration of a specific therapeutic protocol is indicated, include in vitro cell culture assays in which a subject tissue sample is grown in culture, and exposed to or otherwise administered a protocol, and the effect of such protocol upon the tissue sample is observed. A lower level of proliferation or survival of the contacted cells indicates that the composition is effective to treat the condition in the subject. Alternatively, instead of culturing cells from a subject, compositions can be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

Prior to testing in humans, compositions for use in the presently disclosed methods can be tested in suitable animal model systems, including but not limited to in rats, mice, chicken, cows, monkeys, rabbits, etc. The principle animal models for cancer known in the art and widely used include mice, as described in Hann et al. (*Curr. Opin. Cell Biol.*, 13, 778-784 (2001)), which is incorporated herein by reference in its entirety.

Further, any assays known to those skilled in the art can be used to evaluate the prophylactic and/or therapeutic utility of the methods and compositions disclosed herein for treatment, prophylaxis, management, and/or amelioration of one or more symptoms associated with a disease or disorder as described herein.

Efficacy in treating inflammatory disorders can be demonstrated by detecting the ability of the compounds of the presently disclosed subject matter or a composition of the presently disclosed subject matter to reduce or inhibit inflammation in an animal and/or to ameliorate or alleviate one or more symptoms associated with an inflammatory disorder. The treatment is considered therapeutic if there is, for example, a reduction is in inflammation and/or amelioration of one or more symptoms following administration of the compound or composition of the presently disclosed subject matter.

V.B. Formulations and Use

Various methods can be used to administer a compound of the presently disclosed subject matter. Methods of introduction include but are not limited to intradermal, intramuscular, intraperitoneal, intravenous, subcutaneous, intranasal, epidural, inhalation, insufflation (either through the mouth or the nose), oral, buccal, or rectal routes. The compositions can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. In addition, it can be desirable to introduce the pharmaceutical compositions of the presently disclosed subject matter into the central nervous system by any suitable route, including intraventricular and intrathecal injection; intraventricular injection can be facilitated by an intraventricular catheter, for example, attached to a reservoir, such as an Ommaya reservoir. Pulmonary administration can also be employed, e.g., by use of an inhaler or nebulizer and formulation with an aerosolizing agent.

In some embodiments, it is desirable to administer the compositions of the presently disclosed subject matter locally to the area in need of treatment. This can be achieved, for example, and not by way of limitation, by local infusion during surgery, by a catheter, by a suppository, or by an implant. The implant can be a porous, non-porous, or gelatinous material, including membranes, such as sialastic membranes, or fibers, by way of example and not limitation.

In some embodiments, the presently disclosed compounds can be delivered in a vesicle, in particular a liposome. See Langer, *Science*, 249, 1527-1533 (1990); and Treat et al., in *Liposomes in the Therapy of Infectious Disease and Cancer*, Lopez-Berestein and Fidler (eds.), Liss, New York, 1989, pp. 317-327 and 353-365.

In some embodiments, the presently disclosed compounds can be delivered in a controlled release system. In some embodiments, a pump is used. See Langer, *Science*, 249, 1527-1533 (1990); Sefton, *CRC Crit. Ref., Biomed. Eng.*, 14, 201 (1987); Buchwald et al., *Surgery*, 88, 507 (1980); and Saudek et al., *N. Engl. J. Med.*, 321, 574 (1989). In some embodiments, polymeric materials can be used. See Langer and Wise (eds.), Medical Applications of Controlled Release, CRC Press, Boca Raton, Fla., 1974; Smolen and Ball (eds.), Controlled Drug Bioavailability, Drug Product Design and Performance, Wiley, New York, 1984; Ranger and Peppas, J. Macromol. Sci. Rev. Macromol. Chem., 23, 61 (1983); see also Levy et al., *Science*, 228, 190 (1985); During et al., *Ann. Neurol.*, 25, 351 (1989); and Howard et al., *J. Neurosurg.*, 71, 105 (1989). In some embodiments, a controlled release system can be placed in proximity of the therapeutic target, thus requiring only a fraction of the systemic dose. See Goodson, in *Medical Applications of Controlled Release*, Langer and Wise (eds.), CRC Press, Boca Raton, Fla., 1974. Other controlled release systems are discussed in Langer (*Science*, 249, 1527-1533 (1990)).

Other methods of delivery of the therapeutics of the presently disclosed subject matter can be used for example, as described in U.S. Pat. No. 5,679,350, which is incorporated by reference in its entirety.

The presently disclosed subject matter also provides pharmaceutical compositions. Such compositions comprise a therapeutically effective amount of one or more compounds of Formula (I) of the presently disclosed subject matter and a pharmaceutically acceptable carrier. "Pharmaceutically acceptable" refers to those carriers, compositions, and/or dosage forms that are, within the scope of sound medical judgment, suitable for contact with the tissues of human beings and/or other animals without excessive toxicity, irritation, allergic response, or other problems or complications commensurate with a reasonable benefit/risk ratio. Thus, in some embodiments, the presently disclosed compounds can be provided in formulations comprising the compound and a carrier that is pharmaceutically acceptable for use in humans. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* (1990). Such compositions will contain in some embodiments a therapeutically effective amount of the ACDase inhibitor or related prodrug in purified form, together with a suitable amount of carrier so as to provide the form for proper administration to the subject. The formulation should suit the mode of administration.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The compounds of the presently disclosed subject matter can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amounts of the compounds of the presently disclosed subject matter which are effective in the treatment of a particular disorder or condition can depend on the nature of the disorder or condition and can be determined by standard clinical techniques. In addition, in vitro assays and animal models can optionally be employed to help identify optimal dosage ranges. The precise dose to be employed in the formulation can also depend on the route of administration and the seriousness of the disease or disorder, and should be determined according to the judgment of the practitioner and each subject's circumstances.

In some embodiments, the compounds of the presently disclosed subject matter are administered intramuscularly. Suitable dosage ranges for the intramuscular administration are generally in some embodiments about 10 µg to 1 mg per dose and in some embodiments about 10 µg to 100 µg per dose. In some embodiments, the composition is administered in two doses, where the second dose is administered 24 hours after the first dose. In some embodiments, a composition of the presently disclosed subject matter is administered in three doses, with one dose being administered on each of days 1, 4, and 7 of a 7-day regimen.

Suppositories generally contain active ingredient in the range of 0.5% to 10% by weight; oral formulations generally contain 10% to 95% active ingredient.

The presently disclosed subject matter also provides a pack or kit for therapeutic use comprising one or more containers filled with one or more of the ingredients of the pharmaceutical compositions of the presently disclosed subject matter. Optionally associated with such container(s) can be a notice in the form prescribed by a governmental agency regulating the manufacture, use, or sale of pharmaceuticals and/or diagnostic products, which notice reflects approval by the agency of manufacture, use, or sale for human administration.

Pharmaceutical compositions for use in accordance with the presently disclosed subject matter can be formulated in conventional manner using one or more physiologically acceptable carriers or excipients.

For oral administration, the pharmaceutical compositions can take the form of, for example, tablets or capsules prepared by conventional means with pharmaceutically acceptable excipients such as binding agents (e.g., pre-gelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional approaches with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate.

Preparations for oral administration can be suitably formulated to give controlled release of the active agent in the composition.

For buccal administration, the compositions can take the form of tablets or lozenges formulated in conventional manner.

For administration by inhalation, the compositions for use according to the presently disclosed subject matter can be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide, or other suitable gas). In the case of a pressurized aerosol, the dosage unit can be determined by providing a valve to deliver a metered amount. Capsules and cartridges of e.g., gelatin, for use in an inhaler or insufflator can be formulated containing a powder mix of the composition and a suitable powder base such as lactose or starch.

The compositions can be formulated for parenteral administration (i.e., intravenous or intramuscular) by injection via, for example, bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing, and/or dispersing agents. Alternatively, the active ingredient can be in powder form for constitution with a suitable vehicle, e.g., sterile pyrogen-free water, before use.

The compositions can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (for example subcutaneously or intramuscularly) or by intramuscular injection. Thus, for example, the compositions can be formulated with suitable polymeric or hydrophobic materials (for example, as an emulsion in an acceptable oil) or ion exchange resins, or as sparingly soluble derivatives, for example, as a sparingly soluble salt.

EXAMPLES

The following Examples provide illustrative embodiments. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods

Chemistry. Unless otherwise noted, all solvents and general reagents were purchased from Sigma-Aldrich (St. Louis, Mo., United States of America) and Fluka (Buchs, Switzerland). B13 and LCL204 were synthesized as previously described. See Szulc et al., *Bioorg. Med. Chem.*, 16, 1015-1031 (2008). Reaction progress was monitored by analytical normal and/or reverse phase thin layer chromatography (NP TLC or RP TLC) with detection using the PMA reagent (ammonium heptamolybdate tetrahydrate cerium sulfate, 5:2, g/g) in 125 mL of 10% $H_2SO_4$) and the Dragendorff reagent (Fluka) following heating of the TLC plates at 170° C. or by the UV (254 nm).

Cell Culture. MCF-7 cells (breast adenocarcinoma, pleural effusion) were purchased from American Type Culture Collection (ATCC; Rockville, Md., United States of America) and grown in RPMI 1640 media (Life Technologies, Inc., Carlsbad, Calif., United States of America) supplemented with 10% fetal calf serum (FCS; Summit Biotechnology, Colorado, United States of America) and maintained under standard incubator conditions (humidified atmosphere 95% air, 5% $CO_2$ 37° C.). Cells in the exponential growth phase were harvested from the cultures and used in the experiments.

Example 1

Preparation of ω-Br-Analogs LCL429 and LCL509

Syntheses of Class E analogs were performed as shown in FIG. 1 via their ω-Br-analogs LCL429 and LCL509, which were obtained from compound 1 (i.e., (1R,2R)-2-amino-1(4'-nitrophenyl)-1,3-propandiol) and corresponding bromoacyl-chlorides as previously described. See Szulc et al., *Bioorg. Med. Chem.*, 16, 1015-1031 (2008). Compound 1 is commercially available, e.g., from Sigma-Aldrich (St. Louis, Mo., United States of America).

(1R,2R)-2-[N-(12'-bromo-dodecanoyl)-amino]-1-(4"-nitrophenyl)-1,3-propandiol (LCL429). Prepared from 12-bromododecanoyl chloride and (1R,2R)-2-amino-1-(4'-nitrophenyl)-1,3-propandiol, 1. The crude product was purified by flash column chromatography ($CHCl_3$/MeOH, 10:1, v/v) to give a pure product in 78% yield as a white microcrystalline powder, mp 53.8-55.0° C.; TLC ($CHCl_3$/MeOH, 15:1, v/v), $R_f$=0.2; $^1$H-NMR (400 MHz, $CDCl_3$) δ 8.21 (d, 2H, J=8.4), 7.57 (d, 2H, J=8.4), 6.13 (d, 1H, J=8.0), 5.24 (S, 1H), 4.17 (H, 1H, J=4.0), 3.91 (S, 2H), 3.42 (t, 2H, J=7.2), 2.12 (m, 2H), 1.86 (Q, 2H, J=7.2), 1.46 (m, 4H), 1.10-1.30 (m, 12H).

(1R,2R)-2-[N-(6'-bromohexanoyl)-amino)-1-(4"-nitrophenyl)-1,3-propandiol (LCL509) Prepared from 6-bromohexanoyl chloride and (1R,2R)-2-amino-1(4'-nitrophenyl)-1,3-propandiol, 1. The crude product was purified by flash column chromatography ($CHCl_3$/MeOH=7:1) to give the pure product as white microcrystalline powder in 84% yield, mp 87.1-87.5° C. TLC ($CHCl_3$/MeOH, 7:1, v/v), $R_f$=0.17, $^1$H-NMR (400 MHz, $CDCl_3$) δ 8.17 (d, 2H, J=8.8), 7.54 (d, 2H, J=8.8), 6.31 (d, 1H, J=8.8), 5.20 (S, 1H), 4.16 (H, 1H, J=4.8, J=3.2), 3.80 (d, 2H, J=4.0), 3.35 (t, 2H, J=6.8), 2.12 (Q, 2H, J=7.2, 6.8), 1.77 (Q, 2H, J=7.2, 7.2), 1.48 (Q, 2H, J=7.6, 7.6), 1.29 (Q, 2H, J=7.6).

Example 2

Preparation of Class E Inhibitors

General procedure for the preparation of Class E analogs: The Class E inhibitors were prepared from LCL429 or LCL509 and corresponding amines: ammonia, methylamine, dimethylamine, imidazole, morpholine or octylamine and purified by flash column chromatography. See FIG. 1. Briefly, to a well-stirred solution of LCL 429 or LCL509 (0.156 mmol) in a mixture of 1.5N NaOH (4 mL) and THF (8 mL), the corresponding amine was added at room temperature (r.t.). The reaction mixture was kept r.t. or under reflux until reaction was completed as observed by thin-layer chromatography (TLC; elution with $CHCl_3$/MeOH, 10:1, v/v). The organic layer was separated, and the aqueous layer was extracted twice with THF (2×5 mL). The combined organic phases were dried over anhydrous $NaSO_4$ and evaporated under a reduced pressure to dryness to give a crude product. This material was purified through column chromatography from the suitable solvent systems to give a pure target compounds as a light yellow oil.

(1R,2R)-2-[N-(12'-{1"-imidazol}-dodecanoyl)-amino]-1-(4"-nitro-phenyl)-1,3-propandiol (LCL433). Prepared from LCL429 and imidazole in 33% yield as light yellow oil. TLC ($CHCl_3$/MeOH/concd. $NH_4OH$, 10:1:0.01, v/v/v), $R_f$=0.15; $^1$H-NMR (400 MHz, $CDCl_3$) δ 8.18 (d, 2H, J=8.4), 7.78 (s, 1H, Imidazol-H), 7.59 (d, 2H, J=8.4), 7.10 (s, 1H, Imidazol-H), 6.99 (s, 1H, Imidazol-H), 6.50 (d, 1H, J=10), 5.26 (d, 1H, J=3.2), 4.22 (m, 2H), 4.02 (t, 2H, J=6.8), 3.88 (d, 2H, J=4.4), 2.08 (t, 2H, J=7.6), 1.81 (q, 2H, J=6.8), 1.46 (q, 2H, J=7.6), 1.08-1.40 (m, 14H). Formula: $C_{24}H_{36}N_4O_5$, MS 461.3 [M+].

(1R,2R)-2-[N-(12'-{1"-morpholine}-dodecanoyl)-amino]-1-(4"-nitrophenyl)-1,3-propandiol (LCL449). Prepared from LCL429 and morpholine in 60% yield as a light yellow oil. TLC ($CHCl_3$/MeOH/concd. $NH_4OH$, 10:1:0.01, v/v/v). $R_f$=0.12, $^1$H-NMR ($CDCl_3$, 400 MHz) δ 8.20 (d, 2H, phenyl-H, J=8.4), 7.56 (d, 2H, phenyl-H, J=8.4), 6.21 (d, 1H, J=8.4), 5.22 (d, 1H, J=3.2), 4.18 (m, 1H), 3.85 (t, 2H, J=4.8), 3.72 (t, 4H, J=4.8), 2.46 (broad, 6H), 2.32 (t, 2H, J=8.0), 2.10 (dt, 2H, J=7.2, 4.0), 0.92-1.50 (m, 16H). Formula: $C_{25}H_{41}N_3O_6$, MS 480.3 [M+].

(1R,2R)-2-[N-(12'-amino-dodecanoyl)amino]-1-(4"-nitrophenyl)-1,3-propandiol (LCL463). Prepared from LCL429 and ammonia, in 40% yield as a white microcrystalline powder, mp 46-48° C. TLC ($CHCl_3$/MeOH/concd. $NH_4OH$, 1:1:0.01, v/v/v), $R_f$=0.12; $^1$H-NMR ($CD_3OD$, 400 MHz) δ 8.13 (d, 2H, phenyl-H, J=8.8), 7.61 (d, 2H, phenyl-H, J=8.8), 5.10 (d, 1H, J=2.8), 4.15 (m, 1H), 3.73 (dd, 1H, J=7.6, 7.6), 3.53 (dd, 1H, J=6.0, 6.0), 3.27 (m, 2H), 2.79 (t, 2H, J=7.2), 2.04 (dt, 2H, J=7.6, 2.8), 1.56 (m, 2H), 1.00-1.40 (m, 14H). Formula: $C_{21}H_{35}N_3O_5$, MS 410.03 [M+].

(1R,2R)-2-[N-(12'-N,N-dimethylamino-dodecanoyl)-amino]-1-(4"-nitrophenyl)-1,3-propandiol (LCL464). Prepared from LCL429 and 2 M dimethylamine in THF solution in 95% yield. TLC ($CHCl_3$/MeOH/$NH_4OH$, 10:1:0.01, v/v/v), $R_f$=0.12; $^1$H-NMR ($CDCl_3$, 400 MHz) δ 8.20 (d, 2H, phenyl-H, J=8.8), 7.58 (d, 2H, phenyl-H, J=8.8), 6.34 (d, 1H, J=8.4), 5.21 (d, 1H, J=3.2), 4.19 (H, 1H, J=4.0, 4.0), 3.86 (m, 2H), 2.40 (t, 2H, J=7.6), 2.31 (5, 6H), 2.12 (t, 2H, J=7.2), 1.20-1.50 (m, 18H). Formula: $C_{23}H_{39}N_3O_5$, MS 438.40 [M+].

(1R,2R)-2-[N-({12'-N-octylamino}-hexanoyl)-amino]-1-(4"-nitro-phenyl)-1,3-propandiol (LCL488). Prepared from LCL509 and octylamine in 32% yield as a light yellow oil. TLC ($CHCl_3$/MeOH/$NH_4OH$, 4:1:0.01, v/v/v), $R_f$=0.23; $^1$H-NMR ($CDCl_3$, 400 MHz) δ 8.12 (d, 2H, phenyl-H, J=8.4), 7.60 (d, 2H, phenyl-H, J=8.8), 7.32 (d, 1H, J=7.8), 5.17 (d, 1H, J=3.2), 3.79-3.68 (qq, 1H, J=4.0, 4.0), 2.84 (m, 4H), 2.15 (t, 2H, J=7.6), 2.31 (S, 6H), 2.12 (t, 2H, J=7.2), 1.20-1.80 (m, 20H), 0.87 (t, 3H, J=7.2). Formula: $C_{23}H_{39}N_3O_5$, MS 438.28 [M+].

(1R,2R)-2-[N-{12'-N-methyl-amino}-dodecanoyl)-amino]-1-(4"-nitrophenyl)-1,3-propandiol (LCL506). Prepared from LCL429 and 2M methylamine in THF solution, in 90% yield as light yellow oil. TLC ($CHCl_3$/MeOH/$NH_4OH$, 4:1:0.01, v/v/v), $R_f$=0.12; $^1$H-NMR ($CD_3OD$, 400 MHz) δ 8.18 (d, 2H, phenyl-H, J=8.8), 7.63 (d, 2H, phenyl-H, J=8.8), 5.17 (d, 1H, J=3.2), 4.19 (m, 1H), 3.76 (dd, 1H, J=7.6, 7.6), 3.62 (dd, 1H, J=5.6, 5.6), 2.91 (t, 2H, J=8.0), 2.65 (S, 3H), 2.31 (S, 6H), 2.09 (t, 2H, J=7.2), 1.68 (m, 2H), 1.00-1.42 (m, 16H). Formula: $C_{22}H_{37}N_3O_5$, MS 424.15 [M+].

Example 3

Preparation of Prodrugs

Figure 2:
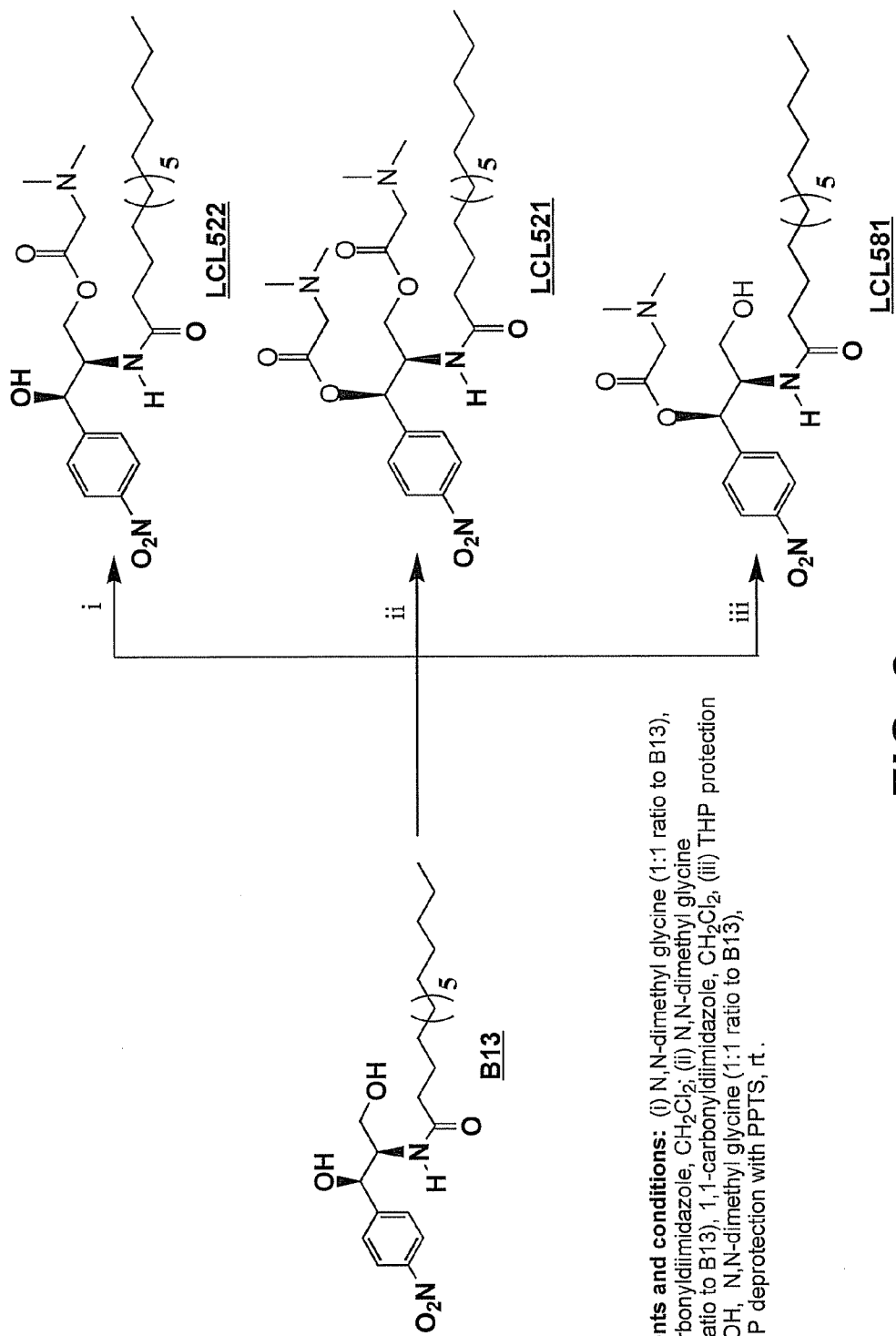
FIG. 2 is a schematic drawing showing the synthesis of Class E compounds that are prodrugs of (1R,2R)-2-N-(tetradecanoylamino)-1-(4'-nitrophenyl)-1,3-propandiol (B13).

As shown in FIG. 2, the presently disclosed prodrug compounds can be prepared from B13 (or a primary or secondary alcohol-containing analog thereof) and N,N-dimethyl glycine (or another suitable carboxylic acid). For example when B13 and N,N-dimethyl glycine are mixed under suitable conditions for esterification (e.g., with carbonyldiimidazole or dicyclohexylcarbodiimide (DCC) and N,N-dimethylaminopyridine (DMAP)) in a 1:1 ratio, a prodrug comprising a single ester (formed at the primary alcohol) can be prepared. When B13 and N,N-dimethyl glycine are mixed in the presence of a molar excess (e.g., greater than 2, 3, 4, 5, 6, 7, 8, 9, 10 or more) of the carboxylic acid, the diester can be formed (i.e., esters are formed at the primary and secondary alcohols). Using a suitable protection strategy for the primary alcohol of B13, mono-ester prodrugs wherein the secondary alcohol are esterified can be obtained. For example, the primary alcohol of B13 can be protected as a tetrahydropyranyl (THP) ether by reacting B13 with dihydropyran in the presence of an acid. Then the secondary alcohol of B13 can be esterified by reaction with N,N-dimethyl glycine. Finally, the THP ether can be removed treating the molecule with pyridimium p-toluenesulfonate (PPTS). For other suitable protecting groups, and methods of protecting and deprotecting alcohols see Greene and Wuts, *Protective Groups in Organic Synthesis*, $3^{rd}$ Ed., John Wiley and Sons, Inc., New York, 1999.

(1R,2R)-2-[N-tetradecanoyl)-amino]-1-(4"-nitrophenyl)-1,3-propandiol-1,3-O-bis-dimethylglycine hydrochloride (LCL521). N,N-dimethyl glycine (103 mg, 1 mmol) and 1,1'-carbonyldiimidazole (162 mg, 1 mmol) were mixed in 10 mL methylene chloride and stirred for 2 hour before B13 (42.3 mg, 0.1 mmol) was added. Reaction mixture was stirred at r.t. until no traces of starting materials were detected. Reaction progress was monitored by TLC (chloroform-methanol-conc. ammonium hydroxide, 10:1:0.025, v/v). Crude product was evaporated to dryness, residue was purified through column chromatography and eluted with chloroform:methanol:conc. ammonium hydroxide (15:1:0.025 (v/v) to give a pure product as a waxy solid. This material was dissolved in ethyl acetate at 4° C. and treated with HCl in ether solution. Reaction mixture was mixed during the time of HCl addition, kept at low temperature for an additional 30 min, evaporated to dryness and further dried under the high vacuum to provide a pure white solid target compound as hydrochloride. LCL521 was obtained in 60% yield. $^1$H NMR (400 MHz, $CD_3OD$) δ 8.238 (d, J=8.8 Hz, 2H), 7.669 (d, J=8.8 Hz, 2H), 6.243 (d, J=4.0 Hz, 1H), 4.75 (m, 1H), 4.581 (dd, J=5.2, 7.2 Hz, 1H), 4.423 (s, 2H), 4.198 (s, 2H), 4.189 (dd, J=5.2, 4.0 Hz), 2.968 (s, 12H), 2.175 (m, 2H), 1.421 (m, 2H), 1.0-1.2 (m, 20H), 0.886 (t, J=6.4 Hz); ESI-MS ($CH_3OH$, relative intensity, %) m/z 593.404 (M–2HCl, 60). Calcd for $[C_{31}H_{54}Cl_2N_4O_7]+$ m/z 665.69

(1R,2R)-2-[N-tetradecanoyl)-amino]-1-(4"-nitrophenyl)-1,3-propandiol-1-O-dimethylglycine hydrochloride (LCL522). N,N-dimethyl glycine (9.3 mg, 0.09 mmol) and 1,1'-carbonyldiimidazole (14.6 mg, 0.09 mmol) were mixed in 3 mL methylene chloride and stirred for 2 hours before B13 (42.3 mg, 0.1 mmol) was added. The reaction mixture was stirred at r.t. until no traces of starting materials were detected. Reaction progress was monitored by TLC (chloroform-methanol-conc. ammonium hydroxide, 10:1:0.025, v/v). Crude product was evaporated to dryness, residue was purified through column chromatography and eluted with chloroform:methanol:conc. ammonium hydroxide (15:1:0.025 (v/v) to give a pure product as a waxy solid. This material was dissolved in ethyl acetate at 4° C. and treated with HCl in ether solution. Reaction mixture was mixed during the time of HCl addition, kept at low temperature for an additional 30 min, evaporated to dryness and further dried under the high vacuum to provide a pure white solid target compound as hydrochloride. LCL522 was obtained in 45% yield. $^1$H NMR (400 MHz, $CD_3OD$) δ 8.180 (d, J=8.8 Hz, 2H), 7.640 (d, J=8.8 Hz, 2H), 5.067 (d, J=2.4 Hz, 1H), 4.620 (dd, J=5.2, 5.2 Hz, 1H), 4.504 (m, 1H), 4.288 (dd, J=8.4, 8.4 Hz, 1H), 4.124 (dd, J=17.2, 17.2 Hz, 2H), 2.961 (s, 6H), 2.068 (m, 2H), 1.358 (m, 2H), 1.1-1.3 (m, 20H), 0.887 (t, J=7.2 Hz, 3H); ESI-MS ($CH_3OH$, relative intensity, %) m/z 508.347 (M–HCl, 70). Calcd for $[C_{27}H_{46}ClN_3O_6]+$ m/z 544.12

Example 4

In Vitro and Cellular Effects of Class E Inhibitors

The Class E compounds were evaluated as inhibitors of ACDase in vitro and at the cellular level, including for their ability to regulate cellular levels of Cers and Sph, the substrates and product of the hydrolytic activity of ACDase. Also, effects of these compounds on ACDase degradation and on lysosomal stability were investigated.

The in vitro assay was carried out according to a previously described procedure (see Zeidan et al., *J. Biol. Chem.*, 281, 24695-24703 (2006)) using [$^3$H] $C_{16}$-Cer as a substrate and MCF-7 cell lysate as an enzymatic source. Briefly, cell lysate was prepared under acidic conditions (i.e., pH 4.5, 50 mM sodium acetate, 5 mM magnesium chloride, 1 mM EDTA and 0.5% Triton X-100), and protein level was determined using BCA protein assay kit (Pierce, Rockford, Ill., United States of America). ACDase activity was determined based on the amount of the released radioactive palmitic acid counted by LS 6500 multi-purpose scintillation counter (Beckman Coulter, Inc., Fullerton, Calif., United States of America). The results are presented as percentage of control.

Effects of the inhibitors on the cellular activity of ACDase were determined using cell lysate from the cultured cells previously treated with increasing concentrations of drugs. For this type of assay, the drugs are allowed to enter the cell for a specific time, then cell lysates were prepared by homogenization and assays performed as described above. Effects on endogenous Cers and Sph were determined using LC-MS/MS analysis as previously described. See Bielawska et al., *Bioorg. Med. Chem.*, 16, 1032-1045 (2008); and Bielawska et al., *Methods*, 39, 82-91 (2006). Final results were expressed as the level of the particular sphingolipid (SPL)/phospholipids (Pi) determined from the Bligh and Dyer lipid extract and expressed as SPLs/Pi (pmol/nmol).

Effects of Class E inhibitors on ACDase protein degradation were determined by Western blotting as previously described. See Bielawska et al., *Bioorg. Med. Chem.*, 16, 1032-1045 (2008); Liu et al., *Front. Biosci.*, 13, 2293-2298 (2008); and Holman et al., *Cancer Chemother. Pharmacol.*, 61, 231-242 (2008). Lysosomal stability and mitochondrial stability were determined by FACS analysis using LYSOTRACKER™ red (Molecular Probes, Eugene, Oreg., United States of America) or JC-1 mitochondrial dye (Molecular Probes, Eugene, Oreg., United States of America) as previously described. See Holman et al., *Cancer. Chemother. Pharmacol.*, 61, 231-242 (2008).

Figure 3:
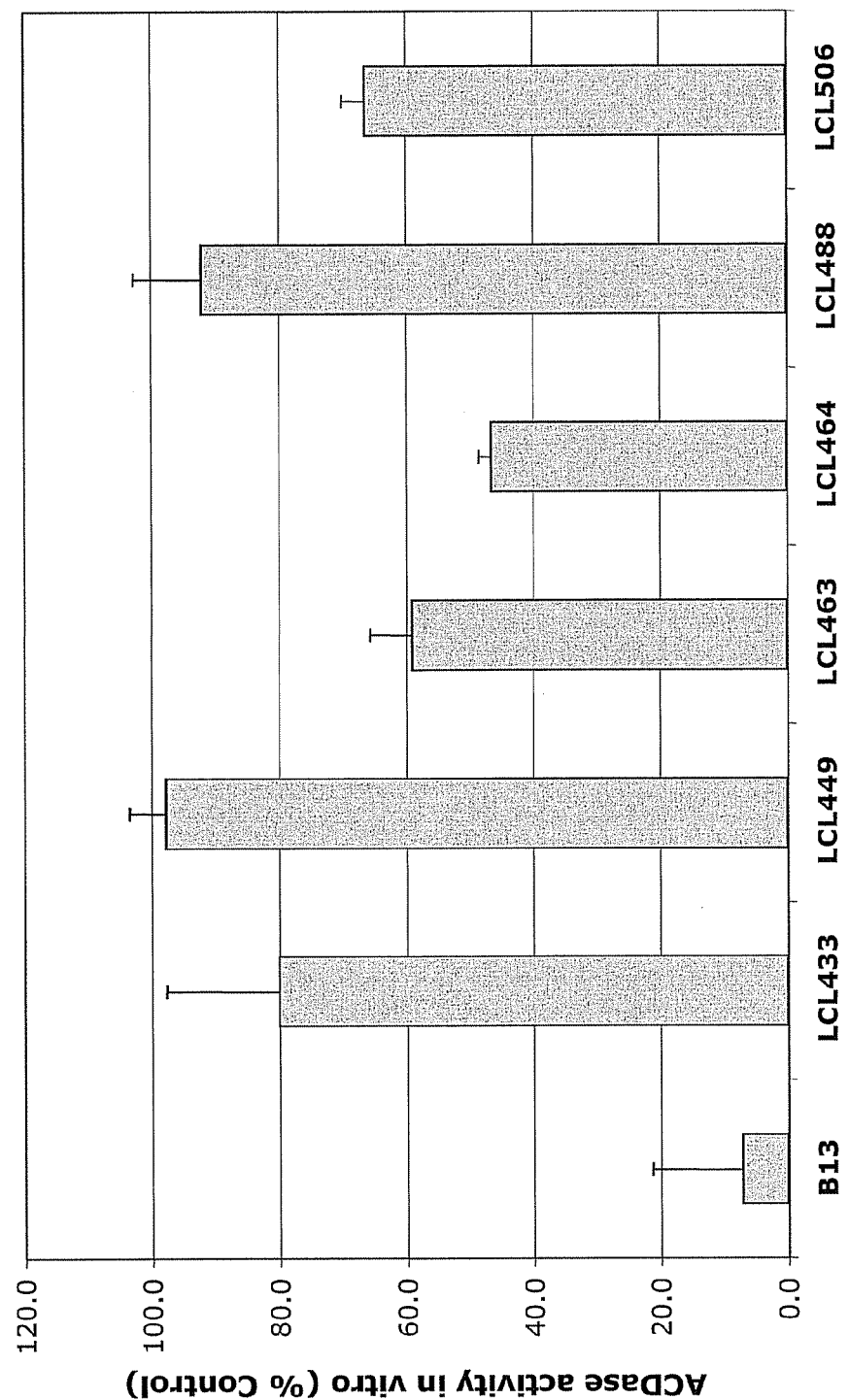
FIG. 3 is a bar graph showing the inhibitory effects of 50 μM Class E inhibitors (LCL433, LCL449, LCL463, LCL464, LCL488 or LCL506) on acid ceramidase (ACDase) in vitro (in MCF-7 cell lysate). ACDase activity was determined based on the release of radioactive palmitic acid from [$^3$H] C16-Cer and is expressed as a percentage of the radioactive palmitic acid released in a control (vehicle only) sample. Results for (1R,2R)-2-N-(tetradecanoylamino)-1-(4'-nitrophenyl)-1,3-propandiol (B13) are shown for comparison.

The inhibitory effects of the Class E compounds compared to the action of B13 are shown in FIG. 3. Results at 50 μM inhibitor concentration showed the highest inhibitory effect of unmodified B13 (~90% inhibition). Under identical conditions, most of the Class E compounds acted as potent inhibitors of ACDase, with LCL464 showing the highest effect, 55% of inhibition.

Figure 4:
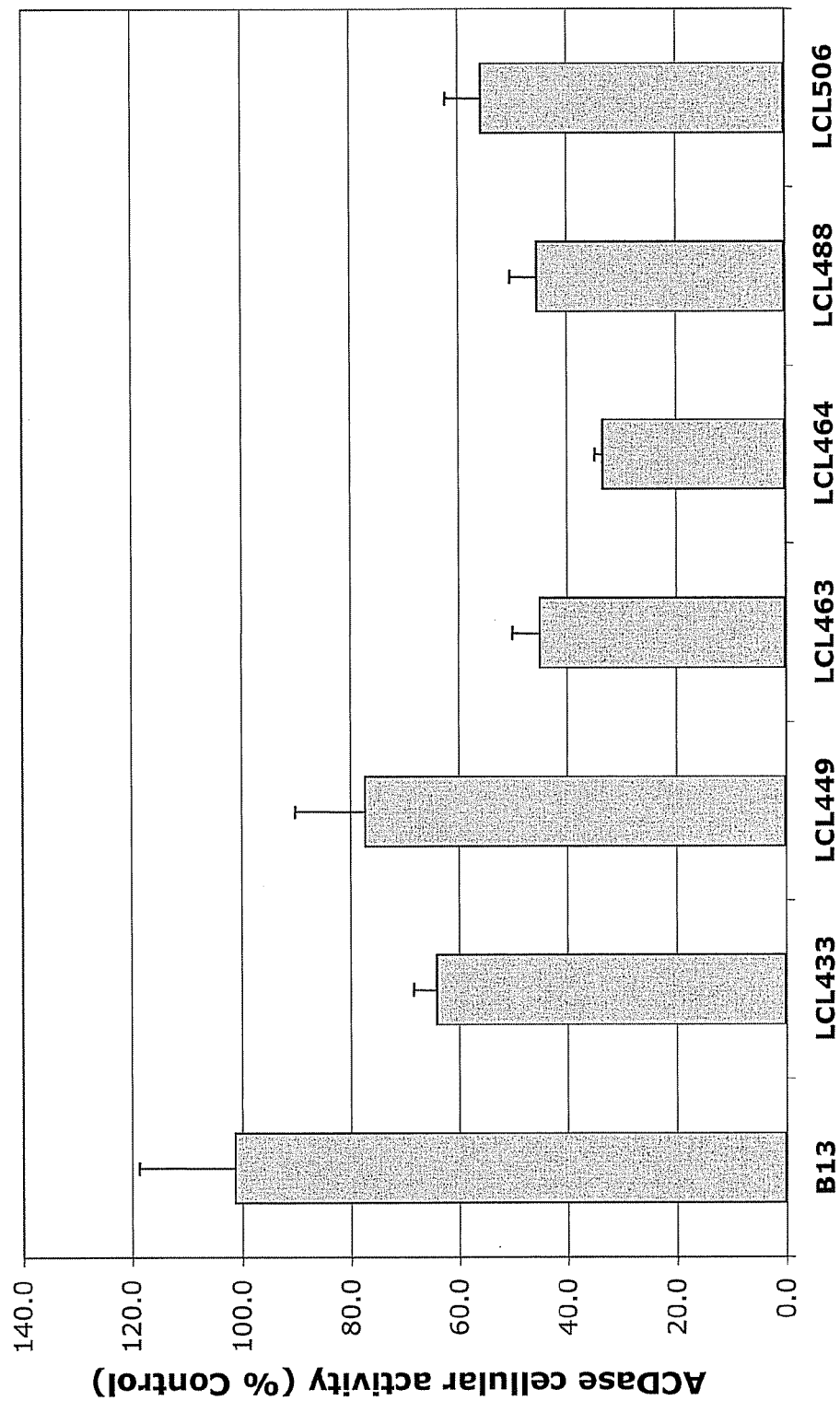
FIG. 4 is a bar graph showing the inhibitory effects of 10 μM Class E inhibitor (LCL433, LCL449, LCL463, LCL464, LCL488 or LCL506) on the cellular activity of acid ceramidase (ACDase). MCF-7 cells were incubated with the Class E inhibitors for 2 hours, homogenized, and the amount of released radioactive palmitic acid determined. Results are expressed as a percentage of the radioactive palmitic acid released in control cells (incubated with vehicle only). Results for (1R,2R)-2-N-(tetradecanoylamino)-1-(4'-nitrophenyl)-1,3-propandiol (B13) are shown for comparison.

As shown in FIG. 4, at the cellular level (2 h of treatment), all tested compounds showed higher potential ACDase inhibition compared to their extracellular in vitro data. The highest inhibition (65%) was detected for LCL464. A previously studied, non-Class E compound, LCL204, i.e., (1R,2R)-15 D-threo-2-N-tetradecylamino-1-(4'-nitrophenyl)-1,3-propandiol, caused about 35% inhibition. Interestingly, B13, the most potent inhibitor in vitro, did not show any ACDase inhibition at the cellular level. Based on both the in vitro and the cellular level results for ACDase inhibition, LCL464 appears to be the most potent inhibitor of ACDase of the Class E analogs tested.

Figure 5A:
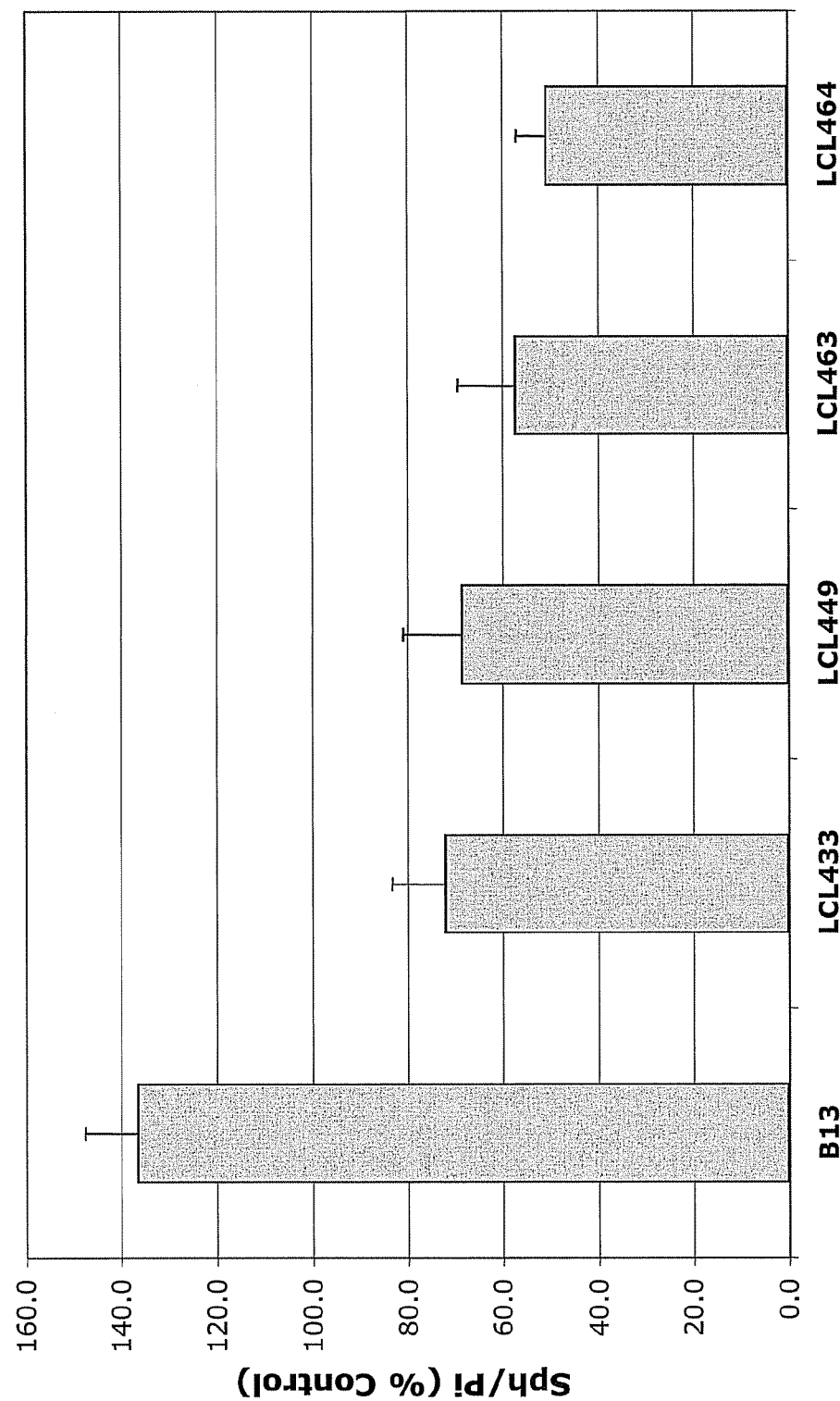
FIG. 5A is a bar graph showing the effects of the Class E inhibitors (LCL433, LCL449, LCL463, LCL464, LCL488 or LCL506; 10 μM) on the level of cellular sphingosine (Sph) after two hours of MCF-7 cell treatment with the compounds. Results for (1R,2R)-2-N-(tetradecanoylamino)-1-(4'-nitrophenyl)-1,3-propandiol (B13) are shown for comparison.
Figure 5B:
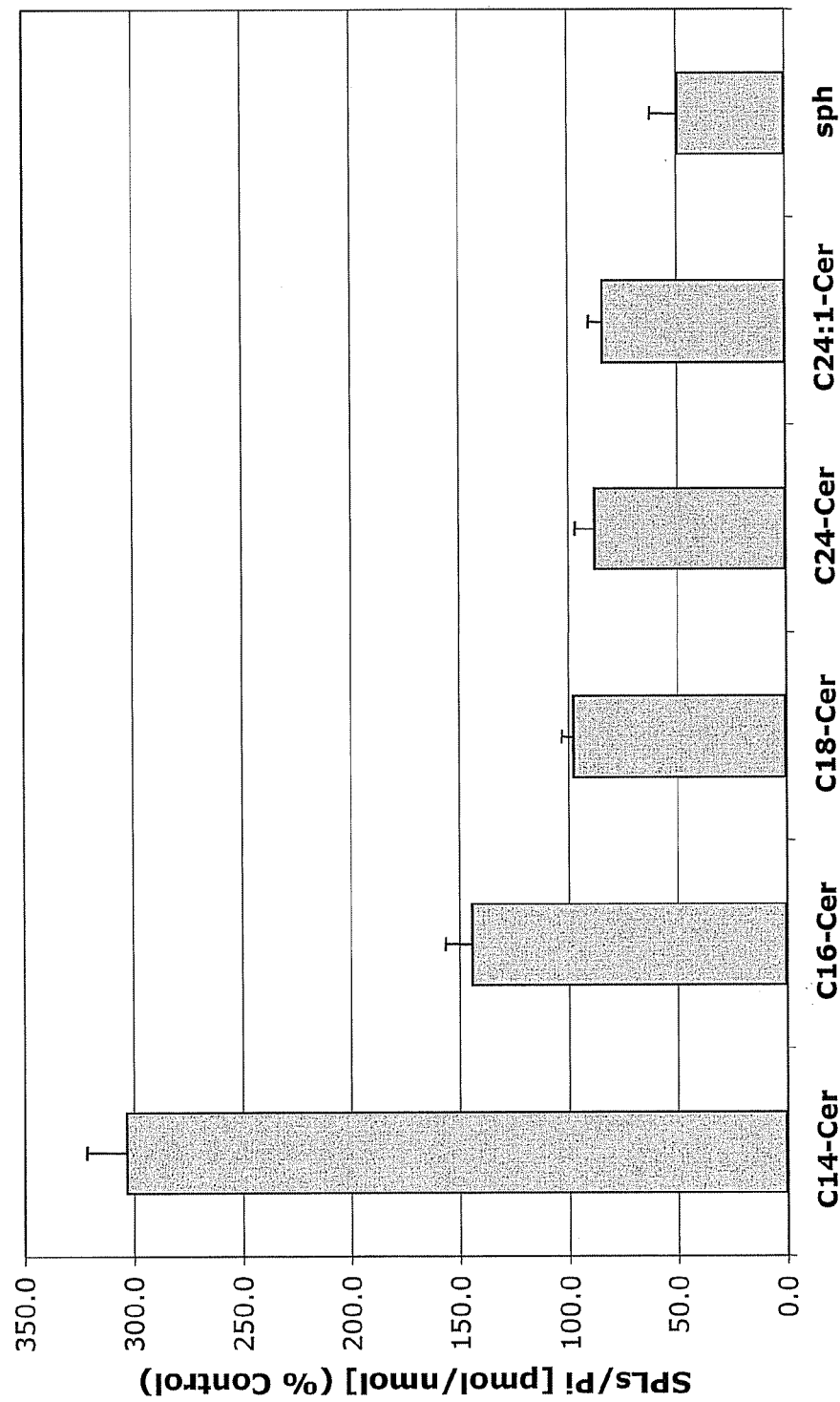
FIG. 5B is a bar graph showing the effect of 10 μM of LCL464 on the levels of cellular sphingolipids (SPLs), including ceramides (C14-Cer, C16-Cer, C18-Cer, C24-Cer, and C24:1-Cer) and sphingosine (Sph), after two hours of MCF-7 cell treatment. Results are expressed as a percentage of the amount of ceramides and sphingosine observed in control cells (treated with vehicle only).
Figure 5C:
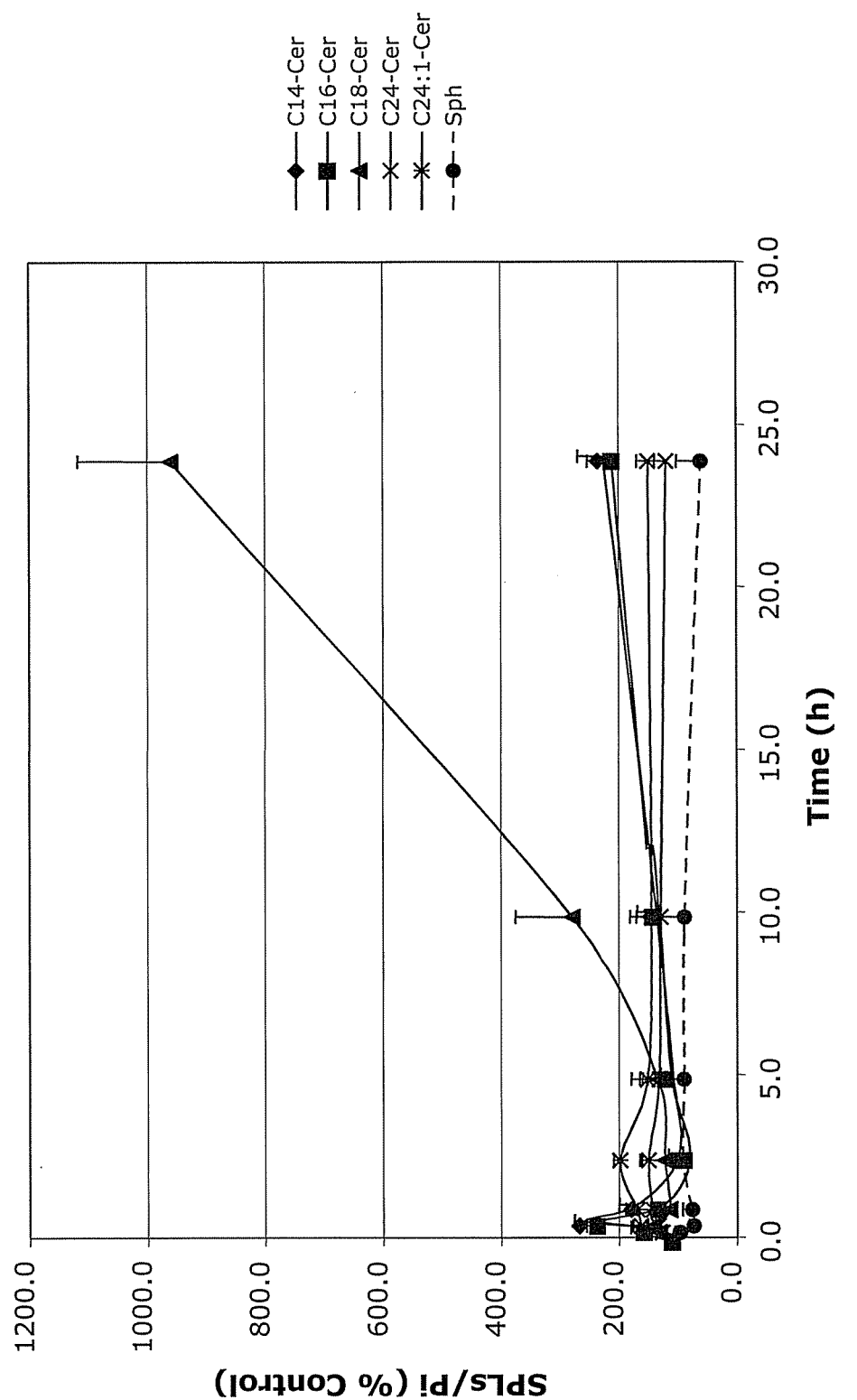
FIG. 5C is a graph showing the time dependence (0-24 hours) of the effects of 50 μM LCL464 on the levels of cellular ceramides (C14-Cer, darkly shaded diamonds; C16-Cer, darkly shaded squares; C18-Cer, darkly shaded triangles; C24-Cer, "x"s; C24:1-Cer, "*"s) and sphingosine (Sph, darkly shaded circles). Results are expressed as a percentage of the amount of ceramides and sphingosine observed in control cells (treated with vehicle only).
Figure 5D:
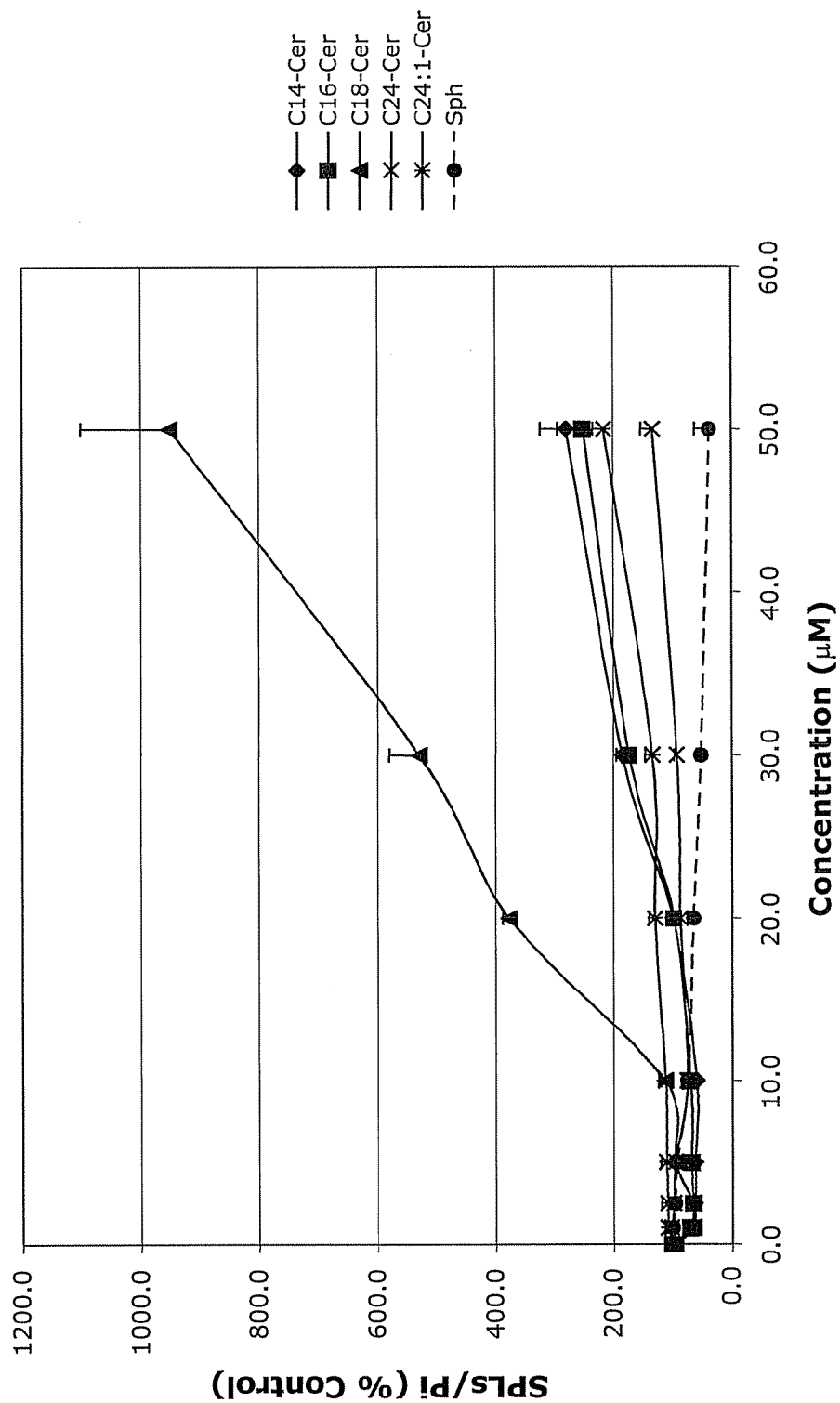
FIG. 5D is a graph showing the dose dependent effect (0-50 μM) of LCL 464 on the levels of cellular ceramides (C14-Cer, darkly shaded diamonds; C16-Cer, darkly shaded squares; C18-Cer, darkly shaded triangles; C24-Cer, "x"s; C24:1-Cer, "*"s) and sphingosine (Sph, darkly shaded circles) after 24 hours. Results are expressed as a percentage of the amount of ceramides and sphingosine observed in control cells (treated with vehicle only).

To connect the observed effects of the inhibitors on the cellular activity of ACDase to the cellular level of sphingolipids, the effects on levels of endogenous Cer species ($C_n$-Cer) and Sph were investigated further. The results showed that 10 μM concentrations of the Class E compounds after 2 h of treatment efficiently decreased (50%-70%) levels of cellular Sph. See FIG. 5A. The compounds did not effectively change the level of total Cer (98%-104%), however they did specifically increase levels of $C_{14}$-Cer to 233%-400% and of $C_{16}$-Cer up to 155%. See FIG. 5B. This characteristic early effect on $C_{14}$-Cer—Sph balance was also observed for 50 μM LCL464. See FIG. 5C. The effect on $C_{16}$-Cer was higher (~240%) as compared to the 10 μM treatment. LCL464 also caused a time dependent and very efficient elevation of $C_{18}$-Cer levels, reaching ~900% of control at 24 hours. This effect on $C_{18}$-Cer was observed for concentrations above 20 μM LCL464. See FIG. 5D. Interestingly, changes in Sph and $C_{18}$-Cer levels were correlated, however with large variations in SD (higher increase in $C_{18}$-Cer corresponded to a lower level of Sph and vice versa). Without being bound to any one theory, these results appear to indicate an additional activatory effect of LCL464 on ceramide synthase 1 (CerS1). Both observed activities, an early inhibition of ACDase specific to $C_{14}/C_{16}$-Cers followed by the activation of ceramidase synthase 1 (CerS1), can cause elevation of the pro-apoptotic $C_{14}$-, $C_{16}$- and $C_{18}$-Cers.

Figure 6:
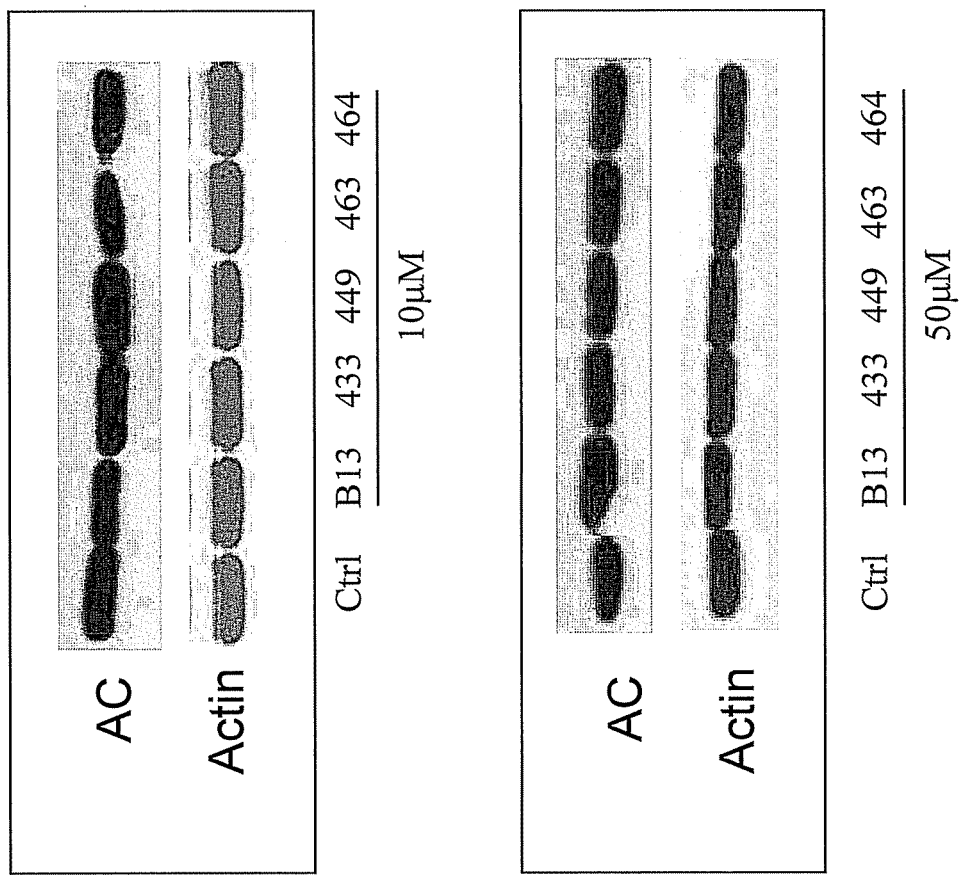
FIG. 6 is a set of micrographs of the Western blot analyses showing the effects of 10 μM (upper lane of top pair of blots) and 50 μM (upper lane of bottom pair of blots) Class E inhibitor (LCL433, LCL449, LCL463, or LCL464) on acid ceramidase (AC) stability as determined by staining for AC in cell lysates using anti-AC antibodies. Actin staining results are also shown (bottom lane of each pair of blots). Results for (1R,2R)-2-N-(tetradecanoylamino)-1-(4'-nitrophenyl)-1,3-propandiol (B13) are shown for comparison. The control lanes in each pair of blots represent the effects of adding vehicle only (no added Class E inhibitor).

The effects of the Class E inhibitors on ACDase expression were determined by Western blot. See FIG. 6. 10 μM concentrations of Class E compounds did not degrade ACDase, as shown for 5 hr treatments. This was in contrast to previously studied ACDase inhibitors, such as LCL204. See Bielawska et al., *Bioorg. Med. Chem.*, 16, 1032-1045 (2008). Furthermore, even when the concentration of the Class E compounds was increased up to 50 μM, they still did not show any effects on ACDase degradation.

Figure 7:
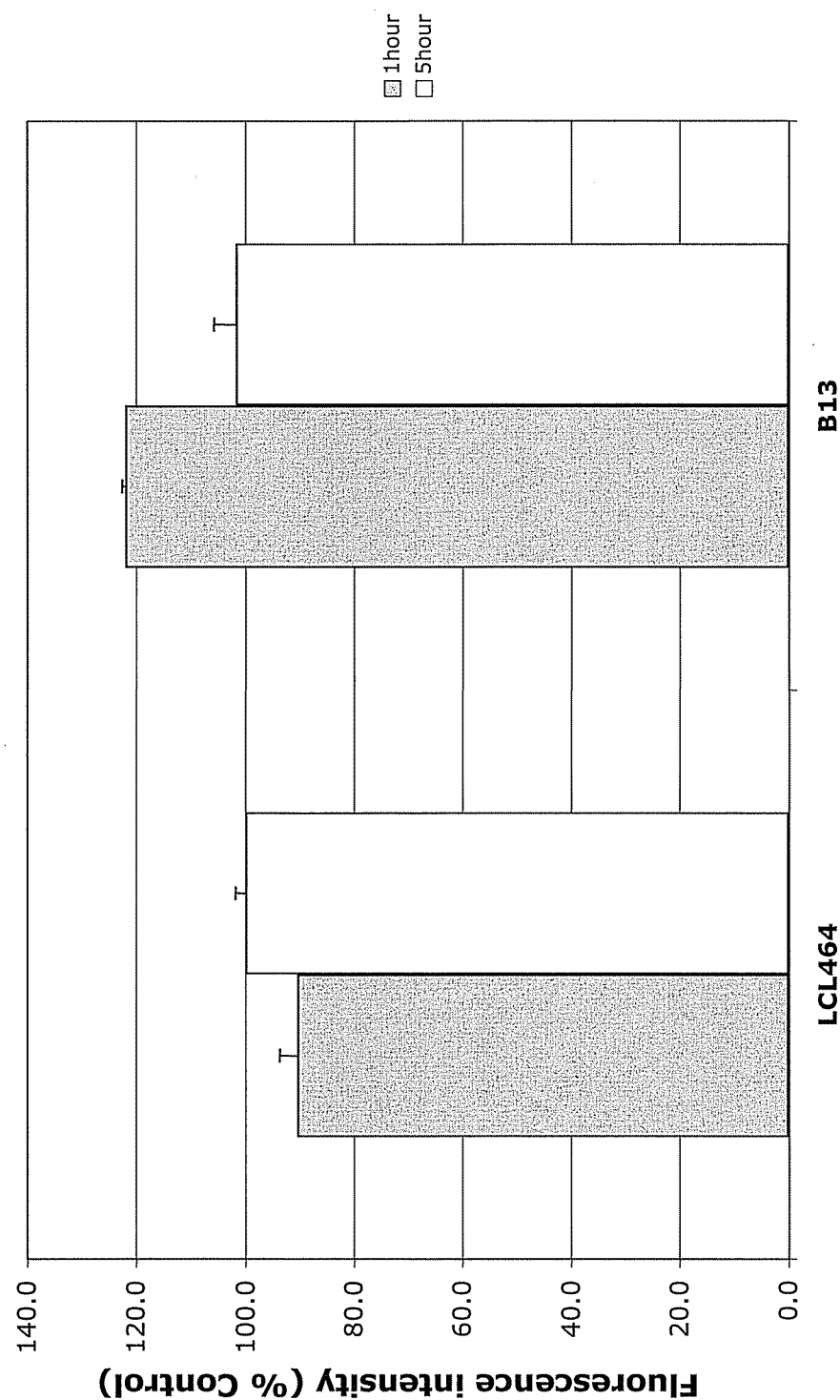
FIG. 7 is a bar graph showing the effects of 10 μM LCL464 or (1R,2R)-2-N-(tetradecanoylamino)-1-(4'-nitrophenyl)-1,3-propandiol (B13) on lysosomal stability after one hour (shaded bars) or five hours (open bars) of treatment. Lysosomal stability was measured using LYSOTRACKER™ Red dye (Molecular Probes, Eugene, Oreg., United States of America) fluorescence. Results are expressed as a percentage of the fluorescence observed in control cells treated with vehicle only.

As shown in FIG. 7, 10 μM LCL464 did not cause lysosomal dysfunction. This result is also observed for B13. Although, as noticed for the higher concentration, 30 μM LCL464 has potential to destabilize the lysosomes (40%/1 h), this dysfunction had recovered by the extended incubation time (61%/5 h, >100%/24 h). Permanent destabilization of the lysosomes was only observed for previously studied non-Class E inhibitors, like LCL204 (lowering lysosomal stability to ~90% as compared to the control). See Bielawska et al., *Bioorg. Med. Chem.*, 16, 1032-1045 (2008).

Example 5

In Vitro and Cellular Effects of Class E Prodrugs

Figure 13:
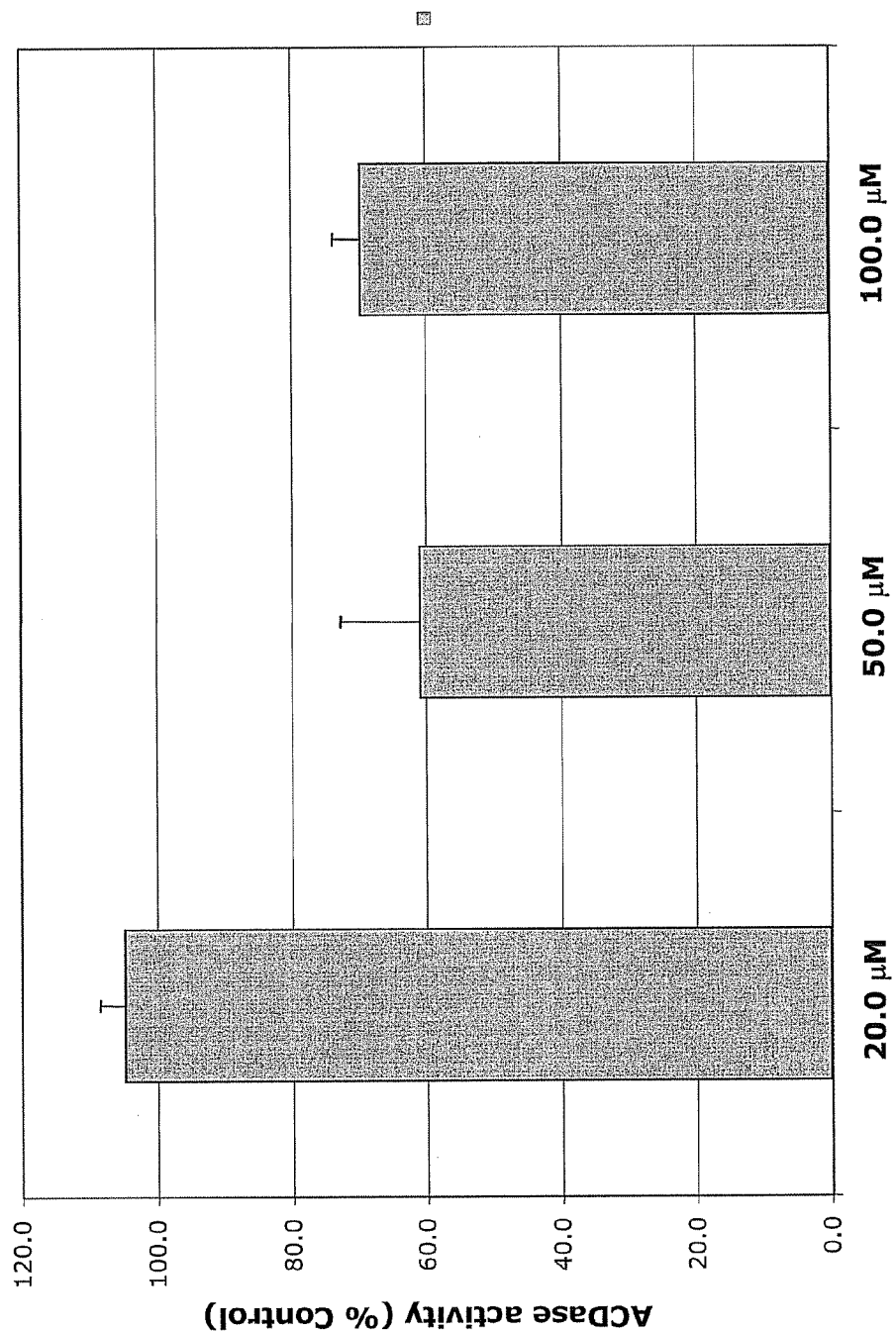
FIG. 13 is a bar graph showing the concentration dependent effect of Class E prodrug LCL521 on acid ceramidase (ACDase) activity in vitro (in MCF-7 cell lysate). ACDase activity was determined based on the release of radioactive palmitic acid from [$^3$H]C16-Cer and is expressed as a percentage of the palmitic acid released in a control (vehicle only) sample.

The Class E prodrugs were evaluated as inhibitors of ACDase in vitro and at the cellular level as described hereinabove in Example 4. As shown in FIG. 13, LCL521 inhibited acid ceramidase in vitro. At the cellular level, LCL521 appeared to cause a decrease in the cellular levels of the alpha-subunit of ACDase, somewhat similar to LCL204, while LCL522 and B13 did not. See FIGS. 14A and 14B. LCL521 also appears to be delivered to the lysosomes, while LCL522 was not. See FIG. 15. LCL521 decreased the cellular level of Sph and S1P and increased levels of pro-apoptotic C16- and C18-Cer, as well as total ceramide. See FIGS. 16 and 17. In contrast, LCL522 behaved similarly to B13 with regard to regulation of cellular sphingolipids. See FIG. 16.

Without being bound to any one theory, the data suggests that LCL522 breaks down under the various assay conditions to form B13, while LCL521 is slowly metabolized to the monoester LCL581 and B13.

Example 6

Effects of Class E Inhibitors in Cancer Cells

Class E compounds were administrated to cells capable of undergoing differentiation in amounts effective to induce differentiation of several cancer cell lines: MCF-7, PPC1, SCC14a, A549, and J3DR4. Cell viability assay was performed by the 3-(4,5-Dimethylthiazol-2-yl)-2,5-diphenyltetrazolium bromide (MTT) assay. Cells were seeded into 96-well plate overnight before treatment with increasing drug concentrations (0-100 μM) as previously described. See Hansen et al., *J. Immunol. Methods*, 119, 203-210 (1989). After treatment, plates were incubated for an additional period of time (24-72 h). Changes in cell numbers were determined and expressed as a percentage of the untreated controls.

Figure 8:
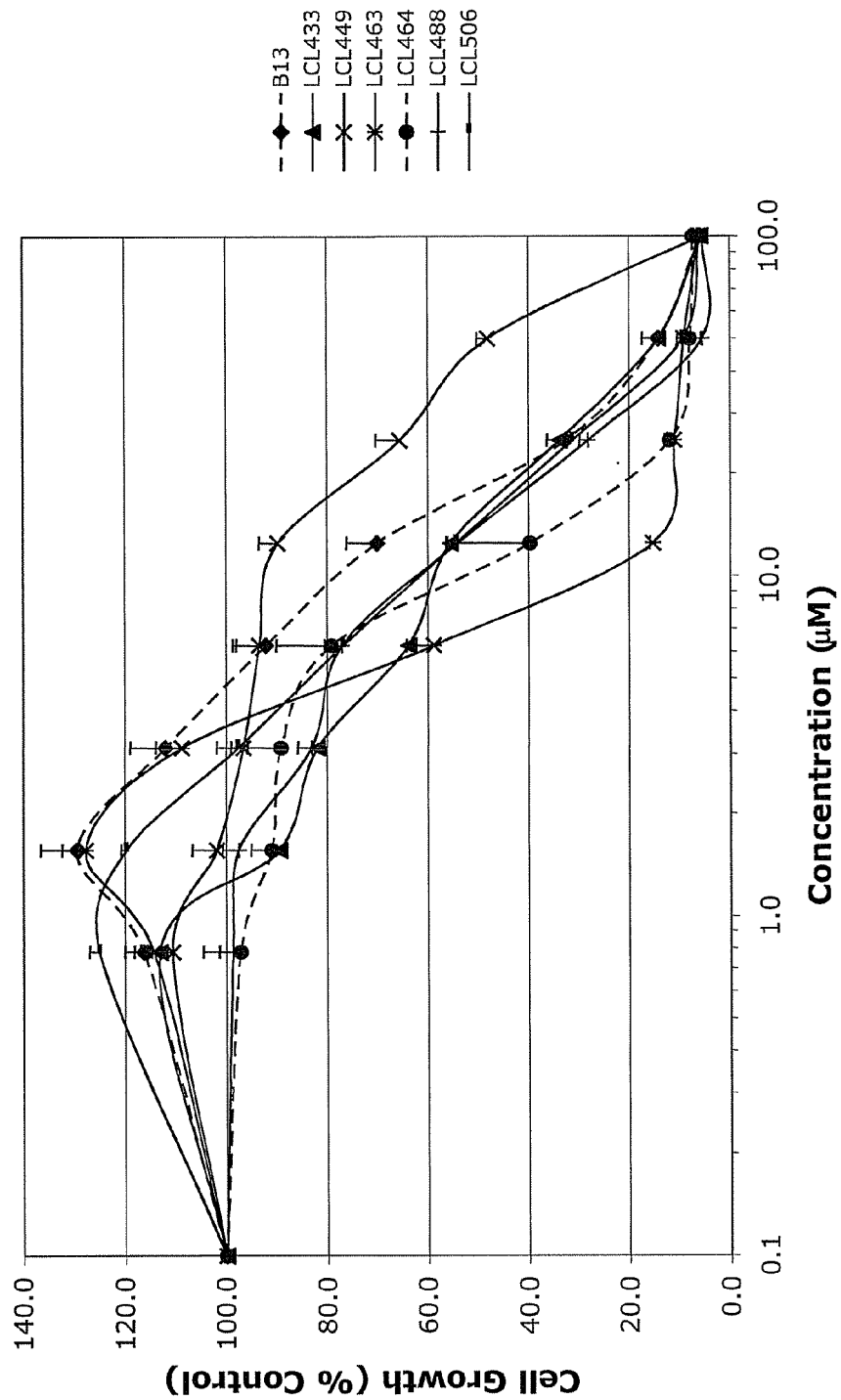
FIG. 8 is a graph showing the concentration dependent inhibitory effects of the Class E inhibitors (LCL 433, darkly shaded triangles; LCL449, "x"s; LCL463, "*"s; LCL464, darkly shaded circles; LCL488, single vertical dashes; or LCL506, horizontial dashes) on MCF-7 breast carcinoma cell growth. The concentration dependent inhibitory effects of (1R,2R)-2-N-(tetradecanoylamino)-1-(4'-nitrophenyl)-1,3-propandiol (B13; darkly shaded diamonds) are provided for comparison. Cell numbers were determined and are expressed as a percentage of cell numbers of control cells (treated with vehicle only).
Figure 9:
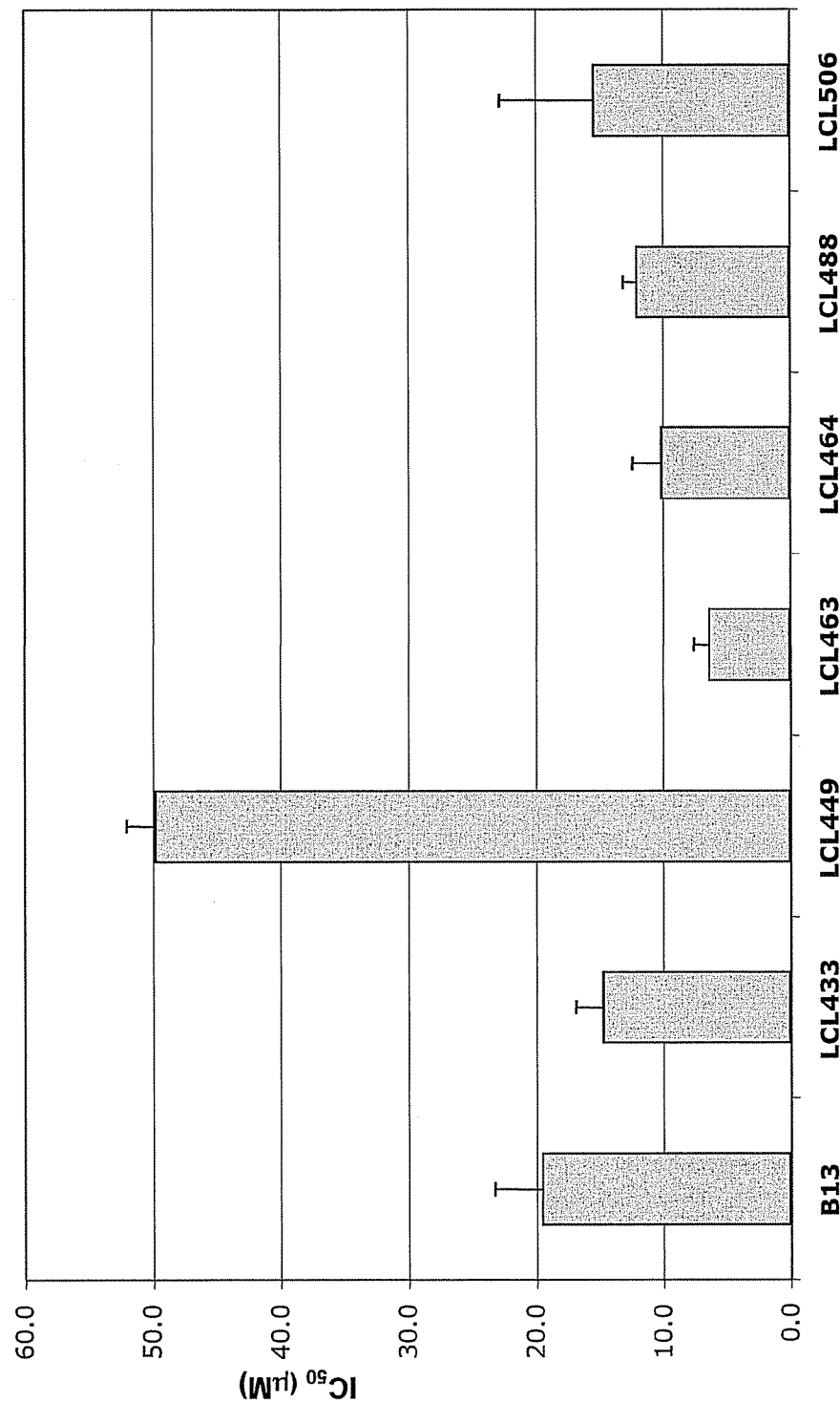
FIG. 9 is a bar graph showing the 50% inhibitory concentration ($IC_{50}$) profiles of the Class E inhibitor (LCL433, LCL449, LCL463, LCL464, LCL488, or LCL506) on MCF-7 breast carcinoma cell growth. For comparison, the $IC_{50}$ is also provided for (1R,2R)-2-N-(tetradecanoylamino)-1-(4'-nitrophenyl)-1,3-propandiol (B13).

The results indicate that the presently disclosed compounds significantly decrease the number of viable cancer cells at a low micromolar range. Concentration dependent inhibitory effects in MCF-7 breast carcinoma cells after 48 hours of treatment with Class E inhibitors are shown in FIG. 8. The $IC_{50}$ profile (50% of surviving cells as compared to the control) of the Class E compounds is shown in FIG. 9. Almost all Class E compounds, except for LCL449, showed increased inhibitory effects compared to those of B13. The most active analogs from Class E were LCL463, followed by LCL464. The $IC_{50}$ values of these analogs ranged from ~6.0-15.5 μM, except for LCL449 (49.9 μM). Results for B13 showed the $IC_{50}$ value of 20.0 μM.

Figure 10:
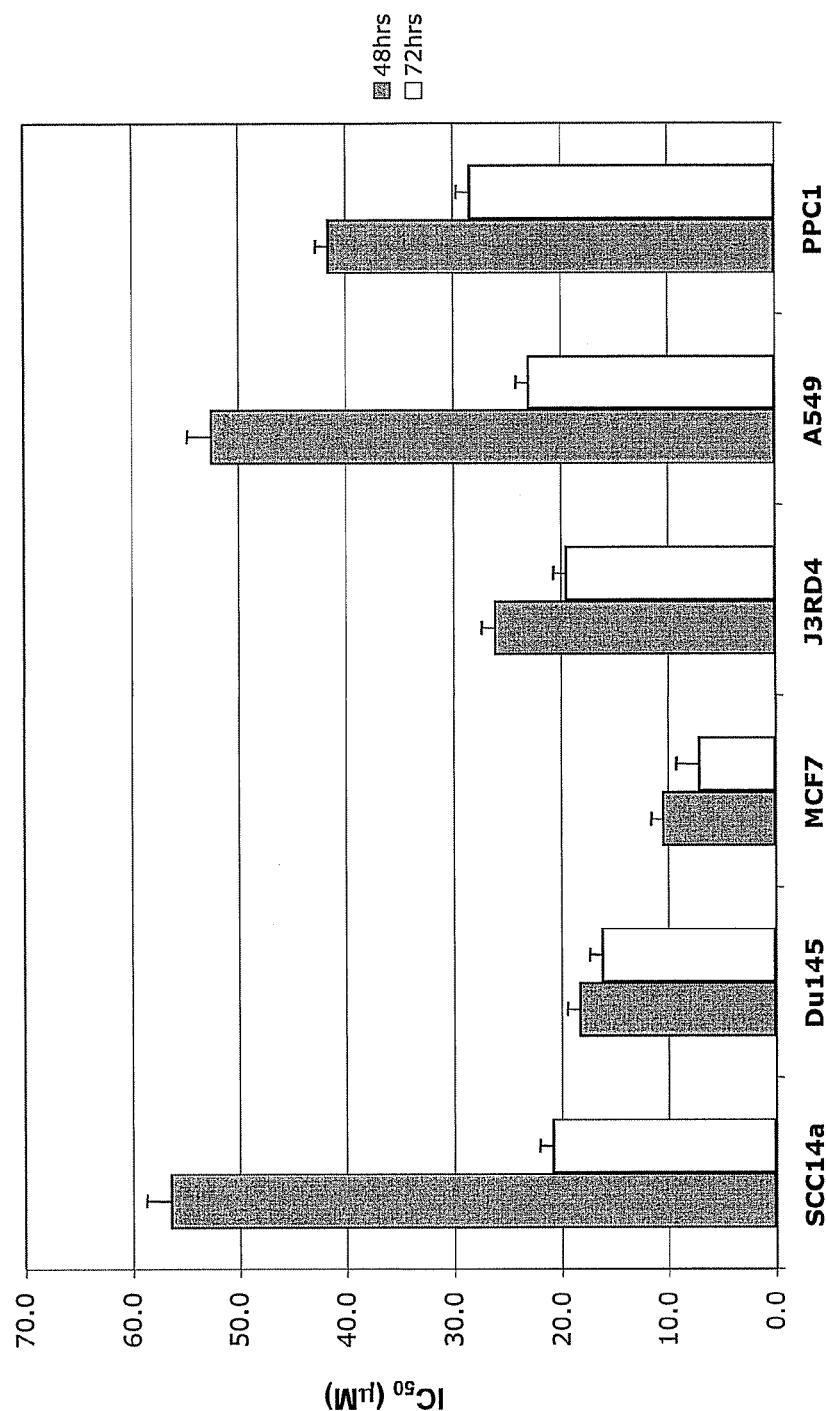
FIG. 10 is a bar graph showing the 50% inhibitory concentration ($IC_{50}$) of LCL 464 in human head and neck squamous cell carcinoma cells (SCC14a), human prostate carcinoma epithelial-like cells (Du145), human melanoma cells (J3DR4), human alveolar epithelia cells (A549), and in a second type of human prostate carcinoma cells (PPC1) in comparison to the effects in the MCF-7 breast carcinoma cells after either 48 hours (shaded bars) or 72 hours (open bars).

The anti-proliferate effect of LCL464 was also investigated in several additional types of tumor cell lines: SCC14a (human head and neck squamous cell carcinoma) Du145 (human prostate carcinoma, epithelial-like cell lines) J3DR4 (human melanoma), A549 (human alveolar epithelial cell), and PPC1 (human prostate carcinoma). FIG. 10 shows the inhibitory effects of LCL464 in the additional cancer cell lines as compared to its effect in the MCF-7 cells after 48 and 72 hour treatments. LCL464 showed the highest effect on growth of MCF-7 cells with the $IC_{50}$ values of 10.2 μM and 7.2 μM, respectively, for 48 and 72 hr treatments. Coincidentally, these effects corresponded to the levels of ACDase with the MCF-7 cells having the highest ACDase protein expression evaluated against the same amount of total protein (data not shown).

Figure 11:
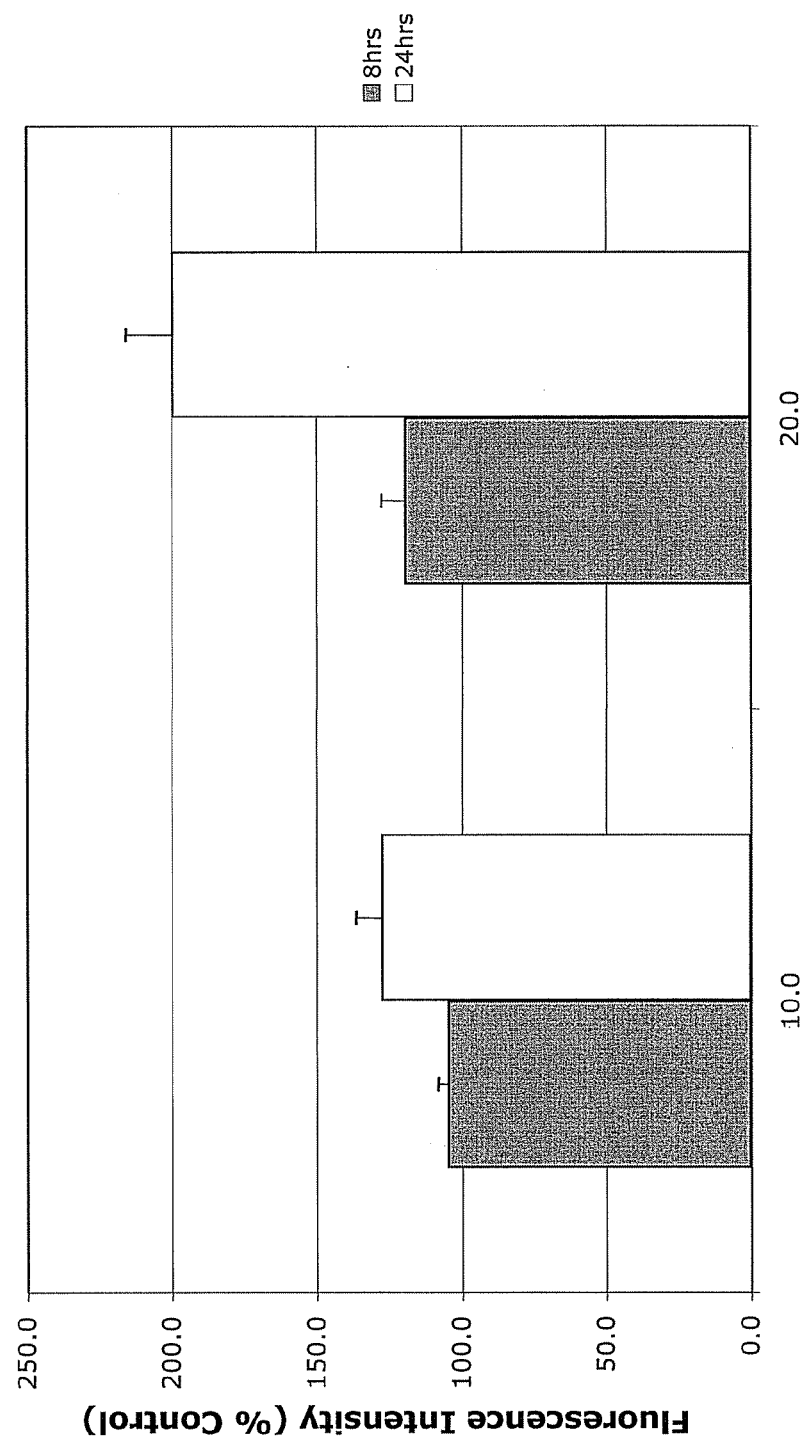
FIG. 11 is a bar graph showing the effect of LCL464 on Caspase 3/7 in MCF-7 cells at 10 and 20 μM concentrations after either 8 hours (shaded bars) or 24 hours (open bars). Results are expressed as a percentage of the Caspase 3/7 in control cells (treated with vehicle only).

The apoptotic effect of LCL464 was also investigated in MCF-7 cells via its effect on Caspase 3/7, a group of cysteine proteases that mediate execution. This can be activated by apoptotic signals from both death receptor and intracellular/mitochondrial pathways. Briefly, MCF-7 cells were seeded at a density of $5 \times 10^3/50$ μL/well overnight in 96 well plates. Then cells were treated with vehicle or diluted LCL464. After 8 and 24 hours incubation, Caspase 3/7 activities were measured using the Apo-ONE Homogeneous Caspase 3/7 Assay Kit according to the manufacturer's instructions (Promega, Madison, Wis., United States of America). LCL464 causes a dose dependent induction of apoptosis following 24 h incubation, causing increase of Caspase 3/7 activities to 140% and 200% for 10 μM and 20 μM, respectively. See FIG. 11.

Example 7

Effects of Class E Prodrugs in Cancer Cells

Class E prodrugs were administered to MCF-7 cells capable of undergoing differentiation in amounts effective to induce differentiation. Cell viability assay was performed by the MTT assay. Cells were seeded into 96-well plate overnight before treatment with increasing drug concentrations (0-100 μM) as previously described. See Hansen et al., *J. Immunol. Methods*, 119, 203-210 (1989). After treatment, plates were incubated for an additional period of time (24-72 h). Changes in cell numbers were determined and expressed as a percentage of the untreated controls. 50% inhibitory concentrations were determined by comparing cell number changes in prodrug treated samples to control samples.

Figure 12:
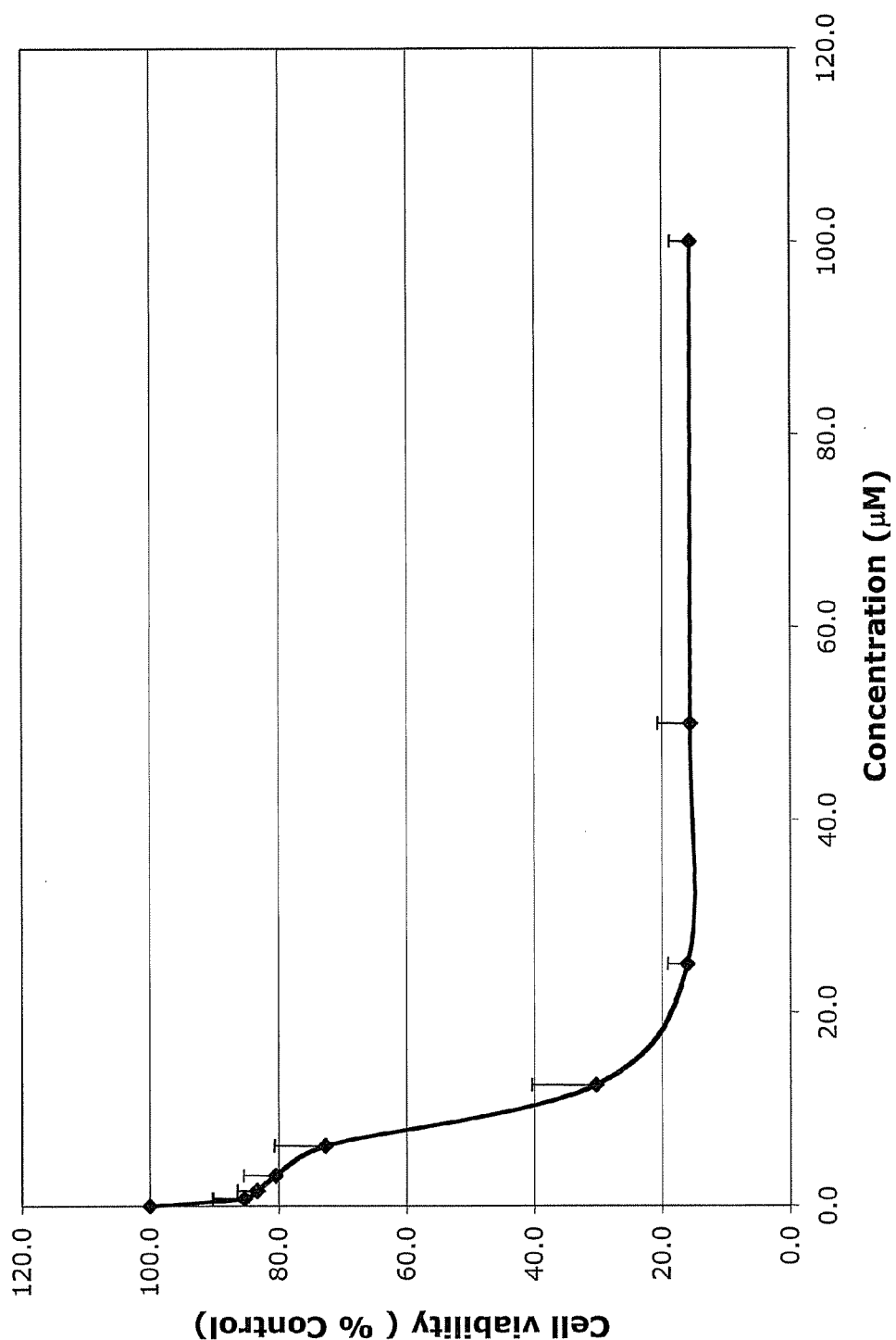
FIG. 12 is a graph showing the concentration dependent inhibitory effects of the Class E prodrug LCL521 on MCF-7 breast carcinoma cell growth.

Dose-dependent cell viability results for LCL521 are shown in FIG. 12. Table 1, below, shows the time dependent $IC_{50}$s (24, 48, or 72 hour) of LCL521 measured via the MTT cell viability assay in MCF-7 breast carcinoma cells. Also shown in Table 1 is the 24 hour $IC_{50}$ for LCL522. For comparison, the time dependent $IC_{50}$s for B13 are provided. Both LCL521 and LCL522 showed increased inhibitory effect on MCF-7 cells as compared to B13 after 24 hours. Thus, based on these preliminary results, it appears that the presently disclosed prodrug approach can increase the therapeutic index of ACDase inhittors. In particular, it appears that the prodrug approach of LCL522 results in increased B13 delivery and potency.

TABLE 1

| Time Dependent $IC_{50}$s of Class E Prodrugs. | | | |
|---|---|---|---|
| compound | $IC_{50/24\,h}$ (μM) | $IC_{50/48\,h}$ (μM) | $IC_{50/72\,h}$ (μM) |
| B13 | 60.8 | 25.8 | 23.9 |
| LCL521 | 8.9 | 8.67 | 7.45 |
| LCL522 | 6.5 | | |

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A compound of Formula (Ib):

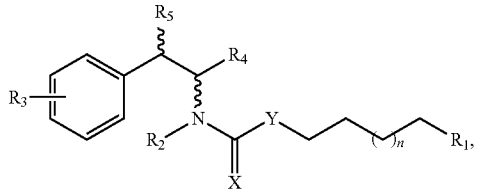

wherein:
n is an integer from 0 to 13;
$R_1$ is selected from the group consisting of H, n-butyl, OH, SH, $NH_2$, Cl, Br, I, C(=O)OH, C(=O)$NH_2$, NH(C=NH)$NH_2$, $NHR_6$, $NR_6R_7$, $^+N(R_6)_3$ and N-heterocycle;
$R_2$ is selected from the group consisting of H and alkyl;
$R_3$ is selected from the group consisting of H, OH, $NO_2$, $NH_2$ and $NHR_9$;
$R_4$ is selected from the group consisting of H, $CH_3$, $CH_2OH$, and $CH_2O$—C(=O)—CH($R_8$)$NR_6R_7$;
$R_5$ is selected from the group consisting of H, OH, =O, and OC(=O)CH($R_8$)$NR_6R_7$;
each $R_6$, $R_7$, and $R_8$ is independently selected from the group consisting of H, alkyl, aralkyl, and aryl;
$R_9$ is C(=O)—(CH$_2$)$_m$$R_{10}$, wherein m is an integer from 5 to 10;
$R_{10}$ is H, alkyl, cycloalkyl, or heterocycle;
X is selected from the group consisting of O, NH, and S;
Y is $CH_2$ or NH; and
wherein at least one of $R_4$ and $R_5$ comprises an ester moiety;

or a pharmaceutically acceptable salt thereof.

2. The compound of claim 1, wherein $R_4$ is $CH_2O$—C(=O)—CH($R_8$)$NR_6R_7$, $R_8$ is H, and $R_6$ and $R_7$ are each alkyl.

3. The compound of claim 1, wherein $R_5$ is OC(=O)CH($R_8$)$NR_6R_7$, $R_8$ is H, and $R_6$ and $R_7$ are each alkyl.

4. The compound of claim 1, wherein $R_4$ is $CH_2O$—C(=O)—CH($R_8$)$NR_6R_7$ and $R_5$ is OC(=O)—CH($R_8$)$NR_6R_7$.

5. The compound of claim 1, wherein n is 5 and $R_1$ is n-butyl.

6. The compound of claim 1, wherein $R_3$ is $NO_2$.

7. The compound of claim 1, wherein the compound is selected from:

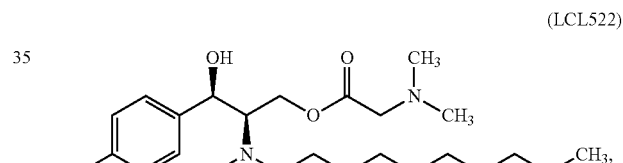
(LCL522)

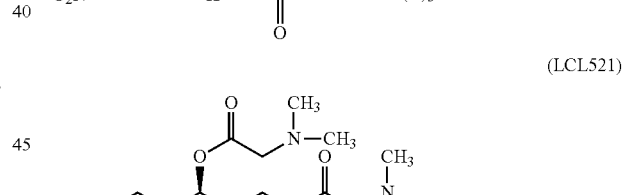
(LCL521)
and

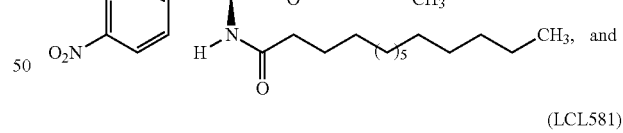

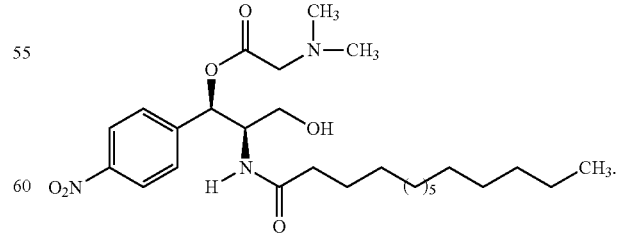
(LCL581)

8. A pharmaceutical composition comprising:
(a) a compound of claim 1; and
(b) a pharmaceutically acceptable carrier.

9. A compound of Formula (Ib):

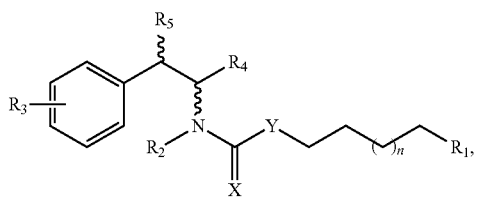

wherein:
n is an integer from 0 to 13;
$R_1$ is selected from the group consisting of H, n-butyl, OH, SH, $NH_2$, Cl, Br, I, C(=O)OH, C(=O)$NH_2$, NH(C=NH)$NH_2$, $NHR_6$, $NR_6R_7$, $^+N(R_6)_3$ and N-heterocycle;
$R_2$ is selected from the group consisting of H and alkyl;
$R_3$ is selected from the group consisting of H, OH, $NO_2$, $NH_2$ and $NHR_9$;
$R_4$ is selected from the group consisting of H, $CH_3$, $CH_2OH$, and $CH_2O$—C(=O)—CH($R_8$)$NR_6R_7$;
$R_5$ is selected from the group consisting of H, OH, =O, and OC(=O)CH($R_8$)$NR_6R_7$;
each $R_6$, $R_7$, and $R_8$ is independently selected from the group consisting of H, alkyl, aralkyl, and aryl;
$R_9$ is C(=O)—$(CH_2)_m R_{10}$, wherein m is an integer from 5 to 10;
$R_{10}$ is H, alkyl, cycloalkyl, or heterocycle;
X is selected from the group consisting of O, NH, and S;
Y is $CH_2$ or NH; and
wherein at least one of $R_4$ and $R_5$ comprises an ester moiety;
or a pharmaceutically acceptable salt or prodrug thereof.

* * * * *

UNITED STATES PATENT AND TRADEMARK OFFICE
CERTIFICATE OF CORRECTION

| | | |
|---|---|---|
| PATENT NO. | : 8,697,379 B2 | Page 1 of 1 |
| APPLICATION NO. | : 13/127888 | |
| DATED | : April 15, 2014 | |
| INVENTOR(S) | : Bielawska et al. | |

It is certified that error appears in the above-identified patent and that said Letters Patent is hereby corrected as shown below:

On title page, item (75) Inventors
replace "Liu Xiang"
with --Xiang Liu--.

Signed and Sealed this
Twenty-sixth Day of August, 2014

Michelle K. Lee
*Deputy Director of the United States Patent and Trademark Office*